United States Patent
Chang et al.

(10) Patent No.: US 11,242,533 B2
(45) Date of Patent: Feb. 8, 2022

(54) RNA-NANOSTRUCTURED DOUBLE ROBOTS AND METHODS OF USE THEREOF

(71) Applicant: ARIZONA BOARD OF REGENTS ON BEHALF OF ARIZONA STATE UNIVERSITY, Skysong—Suite 200, AZ (US)

(72) Inventors: Yung Chang, Tempe, AZ (US); Hao Yan, Chandler, AZ (US); Xiaodong Qi, Tempe, AZ (US); Fei Zhang, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/954,458

(22) PCT Filed: Jan. 10, 2019

(86) PCT No.: PCT/US2019/013118
§ 371 (c)(1),
(2) Date: Jun. 16, 2020

(87) PCT Pub. No.: WO2019/140140
PCT Pub. Date: Jul. 18, 2019

(65) Prior Publication Data
US 2020/0385734 A1  Dec. 10, 2020

Related U.S. Application Data

(60) Provisional application No. 62/615,806, filed on Jan. 10, 2018.

(51) Int. Cl.
| | | |
|---|---|---|
| C12N 15/117 | (2010.01) | |
| B82Y 5/00 | (2011.01) | |
| A61K 38/00 | (2006.01) | |
| A61K 39/00 | (2006.01) | |

(52) U.S. Cl.
CPC .... *C12N 15/117* (2013.01); *A61K 39/001176* (2018.08); *B82Y 5/00* (2013.01); *C12N 2310/16* (2013.01); *C12N 2310/17* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 6,773,885 B1 | 8/2004 | Walder et al. | |
| 8,440,811 B2 | 5/2013 | Chang et al. | |
| 8,552,167 B2 | 10/2013 | Chang et al. | |
| 9,884,114 B2 | 2/2018 | Chang et al. | |
| 10,550,145 B2 * | 2/2020 | Han | C12Y 301/11003 |
| 2005/0261246 A1 | 11/2005 | Chang et al. | |
| 2014/0031416 A1 | 1/2014 | Chang et al. | |
| 2015/0004193 A1 | 1/2015 | Chang et al. | |
| 2015/0017201 A1 | 1/2015 | Chang et al. | |
| 2018/0016569 A1 | 1/2018 | Fu et al. | |
| 2018/0044372 A1 | 2/2018 | Han et al. | |
| 2018/0125969 A1 | 5/2018 | Chang et al. | |

FOREIGN PATENT DOCUMENTS

| | | |
|---|---|---|
| WO | WO2010040091 A1 | 4/2010 |
| WO | WO2010060030 A1 | 5/2010 |
| WO | WO2011049750 A1 | 4/2011 |
| WO | WO2013119676 A1 | 8/2013 |
| WO | 2014170898 A1 | 10/2014 |
| WO | 2014170899 A1 | 10/2014 |
| WO | 2017189870 A1 | 11/2017 |
| WO | WO2019147308 A2 | 8/2019 |
| WO | WO2019147308 A9 | 8/2019 |
| WO | WO2019147309 A2 | 8/2019 |
| WO | WO2019147309 A9 | 8/2019 |

OTHER PUBLICATIONS

Douglas et al., Science, 2012, 335: 831-834.*
Biocca et al., Nano Life, 2015, 5: 1-9.*
Reyes-Reyes et al., Molecular Oncology, 2015, 9: 1392-1405.*
Li et al., Anal. Chem., 2015, 87: 3826-3833.*
Bitler et al., Clin. Cancer Res., 2009, 15: 100-109.*
Hartbottle et al., Human Gene Therapy, 2008, 9, Abstract.*
Biology Online Dictionary, 2021.*
International Search Report and Written Opinion in International Patent Application No. PCT/US19/13118, dated Apr. 29, 2019, in 16 pages.
Liu Xiaoting et al "A dual-targeting DNA tetrahedron nanocarrier for breast cancer cell imaging and drug delivery", Talanta, vol. 179, Nov. 20, 2017 (Nov. 20, 2017), pp. 356-363, XP085329867, ISSN: 0039-9140, DOI 10.1016/J.TALANTA.2017.11.034.
Fan Hong et al "DNA Origami: Scaffolds for Creating Higher Order Structures", Chemical Reviews, vol. 117, No. 20, Oct. 25, 2017 (Oct. 25, 2017), pp. 12584-12640, XP055474939, us ISSN: 0009-2665, DOI: 10.1021/acs.chemrev.6b00825.
Fan Hong et al. "3D Framework DNA Origami with Layered Crossovers", Angewandte Chemie, International Edition, vol. 55, No. 41, Sep. 15, 2016 (Sep. 15, 2016), pp. 12832-12835, XP055579891, ISSN: 1433-7851, DOI: 10.1002/anie.201607050.
Torring T et al "DNA origami: a quantum leap for self-assembly of complex structures", Chemical Society Reviews, vol. 40, No. 12, Dec. 1, 2011 (Dec. 1, 2011), pp. 5636-5646, XP002753787, ISSN: 0306-0012, DOI: 10.1039/C1CS15057J.

(Continued)

*Primary Examiner* — Ileana Popa
(74) *Attorney, Agent, or Firm* — Duane Morris LLP

(57) ABSTRACT

Described herein are immuno-stimulatory RNA nanostructures (which comprises a single-stranded RNA (ssRNA) molecule, wherein the ssRNA molecule forms at least one paranemic cohesion crossover), as well as compositions and methods of use thereof.

15 Claims, 25 Drawing Sheets
Specification includes a Sequence Listing.

(56) References Cited

OTHER PUBLICATIONS

Dongran Han et al "Single-stranded DNA and RNA origami", Science, vol. 358, No. 6369, Dec. 14, 2017 (Dec. 14, 2017), p. eaao2648, XP055579860, us ISSN: 0036-8075, DOI: 10.1126/science.aao2648.

Liu, Ying, et al. "Aptamer-based electrochemical biosensor for interferon gamma detection." Analytical Chemistry 82.19 (2010): 8131-8136.

Morita, Yoshihiro, et al. "Aptamer therapeutics in cancer: current and future." Cancers 10.3 (2018): 80, 22 pages.

Marin-Acevedo, Julian A., et al. "Next generation of immune checkpoint therapy in cancer: new developments and challenges." Journal of Hematology & Oncology 11.1 (2018): 39, 20 pages.

Kondo, Ayano, et al. "Extracellular acidic pH activates the sterol regulatory element-binding protein 2 to promote tumor progression." Cell Reports 18.9 (2017): 2228-2242.

PD-1 / PD-L1 Blockade Bioassay Protocol, Literature # TM468, Mar. 2016, 21 pages; Promega Corporation—2800 Woods Hollow Road—Madison, WI 53711-5399 USA; downloaded from https://www.promega.com/Resources/Protocols/Technical%20Manuals/101/PD1%20PDL1%20Blockade%20Bioassay%20Protocol/.

Mariani, Angelica, et al. "pH-Driven RNA strand separation under prebiotically plausible conditions." Biochemistry 57.45 (2018): 6382-6386.

U.S. Appl. No. 16/642,792, filed Feb. 27, 2020, Yan et al.

Alexopoulou, Lena, et al. "Recognition of double-stranded RNA and activation of NF-κB by Toll-like receptor 3." Nature 413.6857 (2001): 732-738.

Altschul, Stephen F., et al. "Basic local alignment search tool." Journal of Molecular Biology 215.3 (1990): 403-410.

Beaucage, S. L., and M. H. Caruthers. "Deoxynucleoside phosphoramidites—a new class of key intermediates for deoxypolynucleotide synthesis." Tetrahedron Letters 22.20 (1981): 1859-1862.

Chou, Ting-Chao, and Paul Talalay. "Quantitative analysis of dose-effect relationships: the combined effects of multiple drugs or enzyme inhibitors." Advances in Enzyme Regulation 22 (1984): 27-55.

Chou and Talalay, in "New Avenues in Developmental Cancer Chemotherapy," Academic Press, 1987, Chapter 2, 37-64.

Corpet, Florence. "Multiple sequence alignment with hierarchical clustering." Nucleic Acids Research 16.22 (1988): 10881-10890.

Froehler BC, Ng PG, Matteucci MD. Synthesis of DNA via deoxynucleoside H-phosphonate intermediates. Nucleic Acids Res. 1986; 14(13):5399-5407.

Gaffney, Barbara L., and Roger A. Jones. "Large-scale oligonucleotide synthesis by the H-phosphonate method." Tetrahedron Letters 29.22 (1988): 2619-2622.

Garegg, Per J., et al. "Nucleoside H-phosphonates. III. Chemical synthesis of oligodeoxyribonucleotides by the hydrogenphosphonate approach." Tetrahedron Letters 27.34 (1986): 4051-4054.

Garegg, Per J., et al. "Nucleoside H-phosphonates. IV. Automated solid phase synthesis of oligoribonucleotides by the hydrogenphosphonate approach." Tetrahedron Letters 27.34(1986): 4055-4058.

Higgins, Desmond G., and Paul M. Sharp. "Fast and sensitive multiple sequence alignments on a microcomputer." Bioinformatics 5.2 (1989): 151-153.

Huang, Xiaoqiu, et al. "Parallelization of a local similarity algorithm." Bioinformatics 8.2 (1992): 155-165.

Karlin, Samuel, and Stephen F. Altschul. "Methods for assessing the statistical significance of molecular sequence features by using general scoring schemes." Proceedings of the National Academy of Sciences 87.6 (1990): 2264-2268.

Karlin, Samuel, and Stephen F. Altschul. "Applications and statistics for multiple high-scoring segments in molecular sequences." Proceedings of the National Academy of Sciences 90.12 (1993): 5873-5877.

Lehár, Joseph, et al. "Chemical combination effects predict connectivity in biological systems." Molecular Systems Biology 3.1 (2007): 80, 14 pages.

Matsumoto, Misako, et al. "Defined TLR3-specific adjuvant that induces NK and CTL activation without significant cytokine production in vivo." Nature Communications 6.1 (2015): 1-12.

Myers, Eugene W., and Miller, Webb "Optimal alignments in linear space." Bioinformatics 4.1 (1988): 11-17.

Needleman, Saul B., and Christian D. Wunsch. "A general method applicable to the search for similarities in the amino acid sequence of two proteins." Journal of Molecular Biology 48.3 (1970): 443-453.

Pearson, William R., and David J. Lipman. "Improved tools for biological sequence comparison." Proceedings of the National Academy of Sciences 85.8 (1988): 2444-2448.

Pearson WR. Using the FASTA program to search protein and DNA sequence databases. Methods Mol Biol. 1994;24: Ch. 29, pp. 307-331.

Ribas, Antoni. "Adaptive immune resistance: how cancer protects from immune attack." Cancer Discovery 5.9 (2015): 915-919.

Shevtsov, Maxim, and Gabriele Multhoff. "Heat shock protein-peptide and HSP-based immunotherapies for the treatment of cancer." Frontiers in Immunology 7 (2016): 171, 7 pages.

Smith, Temple F., and Michael S. Waterman. "Comparison of biosequences." Advances in Applied Mathematics 2.4 (1981): 482-489.

Takeda, Yohei, et al. "A TLR3-specific adjuvant relieves innate resistance to PD-L1 blockade without cytokine toxicity in tumor vaccine immunotherapy." Cell Reports 19.9 (2017): 1874-1887.

Zhang, Xiaoping, et al. "Paranemic cohesion of topologically-closed DNA molecules." Journal of the American Chemical Society 124.44 (2002): 12940-12941.

Zhou, Yu, et al. "TLR3 activation efficiency by high or low molecular mass poly I: C." Innate Immunity 19.2 (2013): 184-192, first published online Oct. 3, 2012.

\* cited by examiner

IFN-alpha

IFN-beta

Antibody only

RNA origami + antibody

MuLE (Multiple Lentiviral Expression) Destination vector
[Addgene Plasmid #62176]

- Co-expresses iRFP under the control of a PGK promoter

- Tfr-OVA gene along with SV40 promoter replaces ccdb gene in the vector by gateway cloning

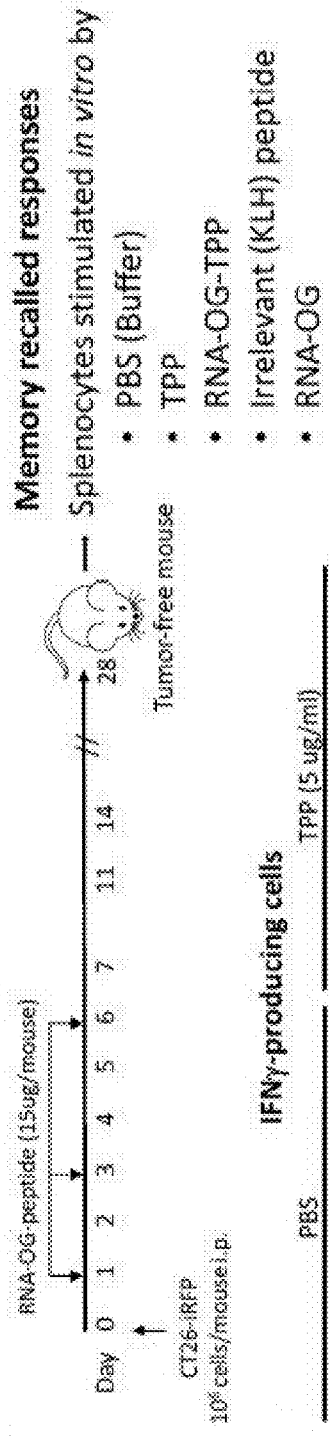
FIG. 19A
FIG. 19B
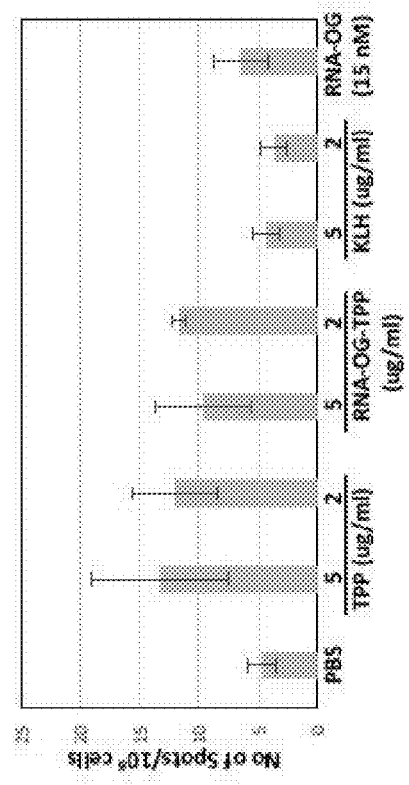
FIG. 19C

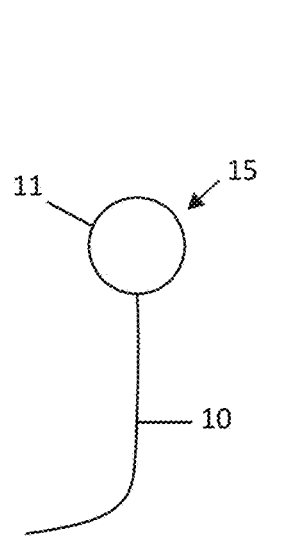
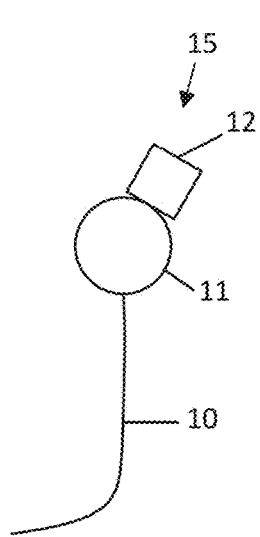
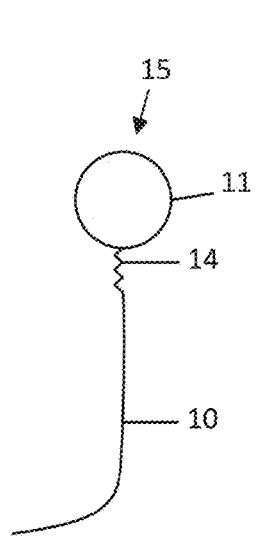
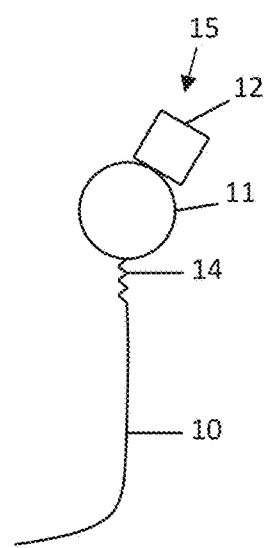
FIG. 24   FIG. 25   FIG. 26   FIG. 27
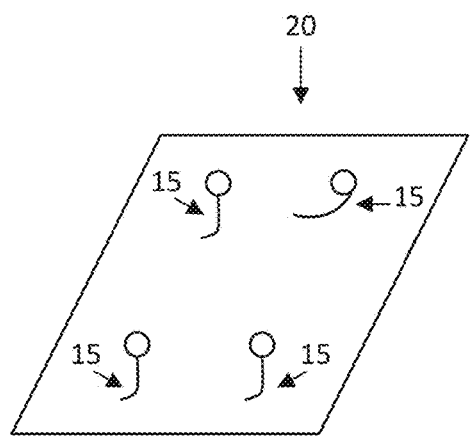
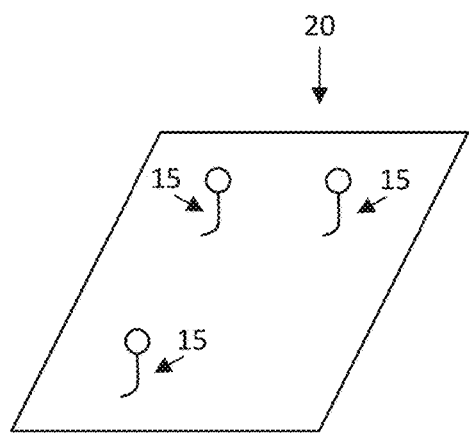
FIG. 28   FIG. 29
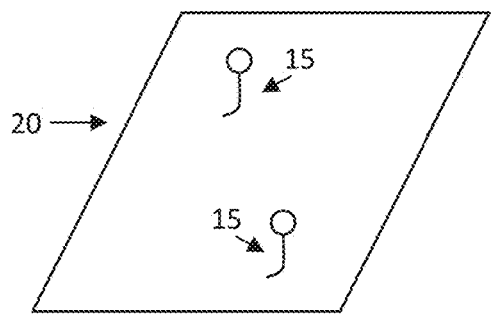
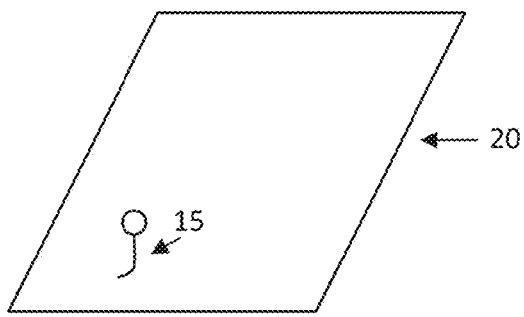
FIG. 30   FIG. 31

RNA-NANOSTRUCTURED DOUBLE ROBOTS AND METHODS OF USE THEREOF

RELATED APPLICATIONS

This application is a 35 U.S.C. 371 National Stage Entry of International Application No. PCT/US2019/013118, filed on Jan. 10, 2019, which claims the benefit of priority of U.S. Provisional Application No. 62/615,806, filed on Jan. 10, 2018, the entire disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 15, 2020, is named G8118-01002_SL.txt and is 48,138 bytes in size.

FIELD

The present invention relates to compositions and methods for treating patients with cancer using immuno-stimulatory RNA nanostructures. The invention also includes methods of creating immuno-stimulatory RNA nanostructures, and compositions comprising said nanostructures.

BACKGROUND

Single stranded RNA (ssRNA) and double stranded RNA (dsRNA) can be detected by pattern recognition receptors in mammalian cells and synthetic ssRNA and dsRNA have been explored as immuno-stimulating adjuvants (Alexopoulou, et al., 2001. Nature 413:732-738.). For example, polyinosinic:polycytidylic acid (polyIC), a synthetic analog of dsRNA, has been widely studied as an adjuvant in treating diseases such as upper respiratory tract infections and tumors, therefore, allowing it to be explored as an adjuvant in flu and cancer vaccines. However, susceptibility of dsRNA to nuclease digestion tends to be a concern especially when they are used in vivo.

TLR3-ligands have been used as adjuvants in cancer vaccination. PolyIC has been used in combination with tumor-specific antigens (TSAs) to induce T-cell dependent responses against tumor cells. PolyIC was mixed with TSAs such as a model antigen, ovalbumin (46 Kd) or with peptides enwrapped within lipid. PolyIC rendered cross-presentation of internalized antigens for an induction of CD8+ cytotoxic T cell activity.

Heat shock proteins (HSPs) with the molecular weights of approximately 70 and 90 kDa have the capacity to stimulate antitumor immune responses either as carriers for antigenic peptides. (Shevtsov M. and Multhoff G. Heat Shock Protein-Peptide and HSP-Based Immunotherapies for the Treatment of Cancer, 2016 Apr. 29; 7:171, Frontiers in Immunology, see FIG. 15.) Heat Shock Protein-70 (HSP70) and derived peptides (also referred to as TPP or TKD) function as chaperones. The chaperone peptides can act as tumor-specific antigens and as immunogens. Linking HSP70 to nanoparticlesllows for the capture of tumor cell lysates to present antigens to dendritic cells (DCs). HSP70 protein and derived peptides can pre-activate NK cells for direct killing of HSP-70+ tumor cells. Dose-dependent and saturable enhancement was found at 0.2-2.0 µg/ml for activation, and at >4 µg/ml no responses. HSP70 induced the proliferation of tumor cells, induced NK cell migration toward HSP70+ tumor cells, the lysis of HSP70+ tumor cells by binding to granzymes and inducing apoptosis of target cells, and increased CD94 expression that can associate with NKG2A and bind to HSP70 to engage with tumor cells. HSP70 also increase dDC maturation and cross-presentation, increased Th1 and CTL activity, and increased M1 activity.

HSP70/TKD moved to clinical trials (I & II), where one out of 12 patients with brain tumor showed CR, who showed increased Th1 and reduced Treg, and where 7 out of 12 patients with HCV-HCC showed complete remission (CR) or stable disease (SD) after receiving HSP70-mRNA transfected to DC.

Accordingly, safe and effective molecular-cargo delivery nano-scaffolds and methods are needed.

SUMMARY

This disclosure provides for RNA nanostructure robots and compositions comprising the same for the treatment of a disease or disorder. In some aspects, the disease or disorder is cancer.

In certain aspects, the present invention provides a RNA nanostructure (also referred to herein as "RNA origami" or "OG-RNA" or "RNA-OG") having the sequence of $(R_3)_n$-$NR_1$-L-$NR_2$-$(R_4)_m$—wherein:
  $NR_1$ represents a first nano-robot comprising a single stranded RNA (ssRNA) of about 1500 to 10,000 bases in length that self-assembles into a first scaffold;
  $NR_2$ represents a second nano-robot comprising a ssRNA, or a DNA cage, of about 1500 to 10,000 bases in length that self-assembles into a second scaffold;
  L is a linker which operably links $NR_1$ to $NR_2$;
  wherein $R_3$ and $R_4$ are independently selected from a pair of fastener strands, an aptamer, a cargo molecule, a capture strand, a targeting strand, or H;
  n is an integer from 0 to 20; and
  m is an integer from 0 to 20.

In some aspects, the ssRNA can comprise the sequence of: $(HD_1$-$LD_1$-$HD_2$-$LD_2)_x$
  wherein x is selected from 2 to 100, 2 to 500, 2 to 1000, 2 to 1500, 2 to 2000, 2 to 2500, 2 to 3000, or 2 to 3500, 2 to 4000, 2 to 4500, 2 to 5000, 2 to 5500, or 2 to 6000;
  wherein $HD_1$ and $HD_2$ are each an RNA helical domain;
  wherein $LD_1$ and $LD_2$ are each an RNA locking domain;
  and further wherein the ssRNA sequence, when folded, exhibits at least one paranemic cohesion crossover.

In certain aspects, the RNA nanostructure robot is an RNA nanostructure double robot or a double nanostructure comprising polynucleotides, where $NR_1$ and $NR_2$ are assembled separately and joined by a linker L. In a certain aspect, the RNA nanostructure is comprised of two or more motifs, wherein the first nano-robot comprises a first motif, and the second nano-robot comprises a second motif. In another aspect, the double nanostructure comprises an RNA nanorobot and a DNA cage. In these and certain aspects, the RNA nanorobot and DNA cage are linked via a linker L. In some aspects, the first and second motifs can be separately transcribed as two separate polynucleotide chains, which are then linked together through the linker L. In certain aspects, the linker L between $NR_1$ and $NR_2$ can be any group that can connect $NR_1$ and $NR_2$ to each other, as disclosed herein, provided that it does not interfere with the function of the $NR_1$ to $NR_2$, $R_3$ and/or $R_4$ moieties. In certain aspects, the linker L between $NR_1$ and $NR_2$ can be any group that can connect the $NR_1$ or $NR_2$ RNA nanostructure robots to each other, as disclosed herein, provided that it does not interfere with the function of the $NR_1$ to $NR_2$, $R_3$ and/or $R_4$ moieties, or the RNA nanostructure or DNA cage. In certain aspects, the linker L is selected from an oligonucleotide, a hybridization complex comprising two DNA or RNA sequences or portions thereof, a DNA-RNA hybridization complex, a polymer, a peptide, an alkyl chain, a polyethylene glycol (PEG) chain, a polypropylene glycol (PPG) chain, or combinations thereof. In some aspects, the linker L comprises RNA ribonucleotides. In some aspects, the oligonucleotide is comprised of DNA, RNA, modified DNA, modified RNA, or combinations thereof. In some aspects, the linker L comprises deoxyribonucleotides. In some aspects, the linker L is a hybridization complex comprising two separate DNA or RNA strands, wherein a first DNA or RNA strand is part of the first nanorobot ($NR_1$), and a second DNA or RNA strand is part of the second nanorobot ($NR_2$). In certain aspects, portions of the two separate DNA or RNA chains can be hybridized to each other to form a linker. In some aspects, the hybridization can be a direct hybridization between a portion of the first DNA or RNA chain which is complementary to a portion of the second DNA or RNA chain. In some aspects, the hybridization can be an indirect hybridization via a bridge oligonucleotide wherein a portion of the sequence of one terminus of the bridge oligonucleotide is complementary to a portion of the sequence of the first DNA or RNA chain, and a sequence of the other terminus of the bridge oligonucleotide is complementary to a portion of the sequence of the second DNA or RNA chain, wherein hybridization occurs between portions of each of the first and second DNA or RNA chains and the bridging oligonucleotide. In some aspects, when $NR_2$ is a DNA cage, the linker L can be an oligonucleotide connected to $NR_2$ which hybridizes with a polyribonucleotide sequence connected to $NR_1$. In other aspects, the two separate DNA or RNA chains can be joined by a chemical cross-link. The chemical cross-link can be a cross-link which covalently binds the two separate DNA or RNA chains to each other. The chemical cross-link can be achieved through the incorporation of Psoralen into one of the DNA or RNA chains, and upon photo-irradiation forms a chemical bond to the other DNA or RNA chain. In some aspects, the chemical cross-link can be a binfunctional compound which reacts to a modified DNA or RNA in each of the separate DNA or RNA strands.

In some aspects, $NR_2$ is a DNA nanocage. As used herein, the term "DNA nanocage" refers to comprises a three dimensional body comprising a plurality of structural members comprising DNA, wherein internal surfaces of the plurality of structural members form an inner cavity. The DNA can be M13 viral DNA. DNA nanocages can be those described in U.S. patent application Ser. No. 15/649,351, herein incorporated by reference in its entirety.

In certain aspects, the RNA nanostructure robot is a single chain, where the sequence $NR_1$-L-$NR_2$ is continuous. The $NR_1$-L-$NR_2$ sequence can be transcribed as a single chain (ssRNA) before functionalizing with $R_3$ and $R_4$. In some aspects, one or more of $R_3$ and/or $R_4$ is the same or different. In some aspects, when $R_3$ and $R_4$ are different, there are more than one species of $R_3$. In some aspects, when $R_3$ and $R_4$ are different, there are more than one species of $R_4$. In some aspects, there are from one to 20 different types of species. In some aspects, when there are more than one species of $R_3$, a first species of $R_3$ ("$R_{3a}$") can be an aptamer, and a second species of $R_3$ ("$R_{3b}$") is a peptide. In some aspects, when there are more than one species of $R_4$, a first species of $R_4$ ("$R_{4a}$") is an aptamer, and a second species of $R_4$ ("$R_{4b}$") is a peptide.

In certain aspects, the present invention provides for a RNA nanostructure as described herein where the first scaffold self-assembles into a rectangular shape.

In certain aspects, the present invention provides for a RNA nanostructure robot that further comprises a cargo molecule. In some aspects, $R_4$ is a cargo molecule and m is an integer from 1 to 20. The cargo molecule can be an aptamer, protein, or drug molecule. In some aspects, the protein is an antigen. In some aspects, the cargo molecule is operably linked to $NR_2$.

In some aspects, the present invention provides for a RNA nanostructure robot that further comprises one or more fastener strands of DNA, wherein the one or more molecular fasteners are capable of fastening the first or second scaffold into an origami structure. In some aspects, $R_3$ is a pair of fastener strands which comprise DNA, and the pair of fasteners strands are capable of fastening the first or second scaffold into an origami structure, and n is an integer from 1 to 20. Each of the fastener strands of DNA can comprise a first and a second strand of DNA. The first and second strand of DNA can be selected from a sequence pair of the following oligonucleotides:

```
5'-FITC-labeled F50 and 3'-BHQ1-labeled Comp 15;
FITC-F50-48 and Comp15-48-Q;
FITC-F50-73 and Comp15-73-Q;
FITC-F50-97 and Comp15-97-Q;
FITC-F50-120 and Comp15-120-Q;
FITC-F50-144 and, Comp15-144-Q; or
FITC-F50-169 and Comp15-169-Q;
wherein the aforementioned oligonucleotides
have the following sequences:
5'-FITC-labeled F50:
                                   (SEQ ID NO: 10)
5'-FITC-GGTGGTGGTGGTTGTGGTGGTGGTGGTCTAAAGTTTTGTCGT

GAATTGCG-3';

3'-BHQ1-labeled Comp15:
                                   (SEQ ID NO: 11)
5'-GTAAAGCTTTTTTTTTTTACAACCACCACCACC-3';

FITC-F50-48:
                                   (SEQ ID NO: 12)
5'-FITC-GGTGGTGGTGGTTGTGGTGGTGGTGGTCTAAAGTTTTGTCGT

GAATTGCG-3';

Comp15-48-Q:
                                   (SEQ ID NO: 13)
5'-GTAAAGCTTTTTTTTTTTACAACCACCACCACC-BHQ1-3';

FITC-F50-73
                                   (SEQ ID NO: 14)
5'-FITC-GGTGGTGGTGGTTGTGGTGGTGGTGGTAGAGCTTGACGGGGA

AATCAAAA-3';

Comp15-73-Q:
                                   (SEQ ID NO: 15)
5'-TGTAGCATTTTTTTTTTTACAACCACCACCACC-BHQ1-3';

FITC-F50-97:
                                   (SEQ ID NO: 16)
5'-FITC-GGTGGTGGTGGTTGTGGTGGTGGTGGCGAGAAAGGAAGGGAA

CAAACTAT-3';

Comp15-97-Q:
                                   (SEQ ID NO: 17)
5'-TGAGTTTCTTTTTTTTTTTACAACCACCACCACC-BHQ1-3';
```

-continued

FITC-F50-120:
(SEQ ID NO: 18)
5'-FITC-GGTGGTGGTGGTTGTGGTGGTGGTGGATAGGAACCCATGTAC

AAACAGTT-3';

Comp15-120-Q:
(SEQ ID NO: 19)
5'-CAAGCCCATTTTTTTTTTTACAACCACCACCACC-BHQ1-3';

FITC-F50-144:
(SEQ ID NO: 20)
5'-FITC-GGTGGTGGTGGTTGTGGTGGTGGTGGCACCACCCTCATTTTC

CTATTATT-3';;

Comp15-144-Q:
(SEQ ID NO: 21)
5'-CCGCCAGCTTTTTTTTTTACAACCACCACCACC-BHQ1'-3';

FITC-F50-169:
(SEQ ID NO: 22)
5'-FITC-GGTGGTGGTGGTTGTGGTGGTGGTGGCTACATTTTGACGCTC

ACCTGAAA-3';

Comp15-169-Q:
(SEQ ID NO: 23)
5'-CCCTCAGTTTTTTTTTTTACAACCACCACCACC-BHQ1-3'.

F50 and Comp15;
F50-48 and Comp15-48;
F50-73 and Comp15-73;
F50-97 and Comp15-97;
F50-120 and Comp15-120;
F50-144 and, Comp15-144; or
F50-169 and Comp15-169;
wherein the aforementioned oligonucleotides
have the following sequences:
F50:
(SEQ ID NO: 24)
5'-GGTGGTGGTGGTTGTGGTGGTGGTGGTCTAAAGTTTTGTCGTGAATT

GCG-3';

Comp15:
(SEQ ID NO: 25)
5'-GTAAAGCTTTTTTTTTTTACAACCACCACCACC-3';

F50-48:
(SEQ ID NO: 26)
5'-GGTGGTGGTGGTTGTGGTGGTGGTGGTCTAAAGTTTTGTCGTGAATT

GCG-3';

Comp15-48:
(SEQ ID NO: 27)
5'-GTAAAGCTTTTTTTTTTACAACCACCACCACC-3';

F50-73
(SEQ ID NO: 28)
5'-GGTGGTGGTGGTTGTGGTGGTGGTGGTAGAGCTTGACGGGGAAATCA

AAA-3';

Comp15-73:
(SEQ ID NO: 29)
5'-TGTAGCATTTTTTTTTTTACAACCACCACCACC-3';

F50-97:
(SEQ ID NO: 30)
5'-GGTGGTGGTGGTTGTGGTGGTGGTGGCGAGAAAGGAAGGGAACAAAC

TAT-3';

Comp15-97:
(SEQ ID NO: 31)
5'-TGAGTTTCTTTTTTTTTTTACAACCACCACCACC-3';

F50-120:
(SEQ ID NO: 32)
5'-GGTGGTGGTGGTTGTGGTGGTGGTGGATAGGAACCCATGTACAAACA

GTT-3';

Comp15-120:
(SEQ ID NO: 33)
5'-CAAGCCCATTTTTTTTTTTACAACCACCACCACC-3';

F50-144:
(SEQ ID NO: 34)
5'-GGTGGTGGTGGTTGTGGTGGTGGTGGCACCACCCTCATTTTCCTATT

ATT-3';;

Comp15-144:
(SEQ ID NO: 35)
5'-CCGCCAGCTTTTTTTTTTACAACCACCACCACC-3';

F50-169:
(SEQ ID NO: 36)
5'-GGTGGTGGTGGTTGTGGTGGTGGTGGCTACATTTTGACGCTCACCTG

AAA-3';

Comp15-169:
(SEQ ID NO: 37)
5'-CCCTCAGTTTTTTTTTTTACAACCACCACCACC-3'.

In some aspects, this invention provides for a RNA nanostructure robot, wherein the second strand of fastener DNA comprises a sequence which is partially complementary to the sequence of the first strand.

In some aspects, the moiety $R_4$ is an aptamer that specifically binds a target molecule and comprises domain which comprises a sequence which is partially complementary to the sequence of the second strand, and m is an integer from 1 to 20.

In some aspects, one or more of the $R_3$ and/or $R_4$ moieties is an RNA targeting strand, wherein each targeting strand is operably linked to a targeting moiety and to $NR_1$ or $NR_2$. The targeting moiety can be a moiety which binds to a target. In some aspects, the targeting moiety is selected from: an aptamer that specifically binds a target molecule. In some aspects, the targeting moiety is an antibody. In some aspects the target molecule is a peptide, a protein, an antibody, a glycan, a DNA or RNA sequence, or combinations thereof. In some aspects, targeting moiety is an antibody or fragment thereof, nanobody, receptor or binding domain thereof, aptamer, scFv, fusion protein, or bispecific antibody. In some aspects, the one or more of the $R_3$ and/or $R_4$ moieties is an aptamer specific for nucleolin. In some aspects, the one or more of the $R_3$ and/or $R_4$ moieties is an aptamer or antibody specific to a target selected from: interferon (including or excluding interferon-a/b, and interferon-gamma), a checkpoint inhibitor protein, EGFR, hTNFα, Vaccinia virus, ICAM-1, PDGF-B, VEGF, Nucleolin, Periostin, Vimentin, CEA, AGE, NF-κB, OPN, HGC-27, PSMA, E-selectin, 4-1 BB, OX40, CD28, PSMA/4-1BB, PD-1, PD-L1, IL10R, IL4Ra, CD44/EpCAM, TIM3, CTLA-4, CXCL12, Tenascin-C, Axl, HGC-27, hnRNP Ai, CD16a/c-Met, or VEGF/4-1BB. In some aspects, the aptamer that is specific for nucleolin is an F50 AS1411 aptamer having the sequence: 5'-GGTGGTGGTGGTTGTGGTGGTGGTGG-3' (SEQ ID NO: 38). In some aspects, the targeting strand comprises a domain comprising a polynucleotide sequence for attaching to $NR_1$ or $NR_2$. In some aspects, when the nucleolin-specific aptamer is presented to nucleolin on a tumor cell surface, the aptamer will competitively bind to the surface-bound nucleolin. In some aspects, when the RNA nanostructure scaffold is in the form of a tube comprising a fastener strand wherein the fastener strand is a nucleolin-specific aptamer, when the aptamer competitively binds to the tumor cell surface-bound nucleolin, the fastener strand will release from one or all of the RNA nanostructure scaffolds wherein the scaffold will change shape from a tube to an open rectangular sheet.

In some aspects, this invention provides for a RNA nanostructure robot, wherein the first or second scaffold is configured to have a rectangular sheet having four corners and is shaped into a tube-shape. In some aspects, the dimension of the rectangular sheet can be about 90 nm×about 60 nm×about 2 nm. In some aspects, one or more targeting strands are positioned at one or more corners of the rectangular sheet. In some aspects, the tube-shaped origami structure has a diameter of about 19 nm.

In some aspects, one or more of the $R_3$ and/or $R_4$ moieties is a capture strand. In some aspects, the capture strand can bind to a poly(A) region in $NR_1$ or $NR_2$. In some aspects, the capture strands can be operably linked to a therapeutic agent. In some aspects, the capture strand comprises an RNA loop. In some aspects, the capture strand comprises poly(U). In some aspects, the stand comprises a sequence comprising an amino-modified ribonucleoside.

In some aspects, this invention provides for a RNA nanostructure robot, wherein the ssRNA sequence comprises a modified ribonucleic acid. The ribonucleic acid can comprise an alkyl amine functional group. In some aspects, the amino-modified ribonucleoside is incorporated into the ssRNA sequence by the addition of 5-Aminoallyluridine-5'-Triphosphate during a transcription step of forming the ssRNA sequence.

In some aspects, one or more of the $R_3$ and/or $R_4$ moieties is an agent. In some aspects, the agent is a therapeutic agent. In some aspects, the therapeutic agent is a protein. The protein can be selected from thrombin, prothrombin, or mixtures thereof. In some aspects, the thrombin is conjugated to the amino-modified ribonucleotide by means of a sulfosuccinimidyl-4-(N-maleimidomethyl) (sulfo-SMCC) cyclohexane-1-carboxylate (sulfo-SMCC) as a bifunctional crosslinker. The maleimide group on the sulfo-SMCC can react to a cysteine on a non-reduced or reduced form of the thrombin molecule, and the sulfosuccinimidyl group on the sulfo-SMCC can react to the amino-modified ribonucleoside.

In some aspects, $NR_1$ or $NR_2$ further comprises a complex comprising an RNA nanostructure and at least one therapeutic agent operably linked to the RNA nanostructure.

In some aspects, the RNA nanostructure comprises one single-stranded RNA (ssRNA) molecule which forms at least one paranemic cohesion crossover.

In some aspects, this invention provides for a RNA nanostructure robot, wherein the RNA nanostructure is immuno-stimulatory.

In some aspects, $NR_1$ and/or $NR_2$ comprises a nucleic acid sequence having at least about 90% sequence identity to SEQ ID NO:1 or SEQ ID NO: 9. In some aspects, $NR_1$ and/or $NR_2$ comprises a nucleic acid sequence having at least about 95% sequence identity to SEQ ID NO:1 or SEQ ID NO: 9. In some aspects, $NR_1$ and/or $NR_2$ comprises SEQ ID NO:1 or SEQ ID NO: 9. In some aspects, $NR_1$ and/or $NR_2$ consists of SEQ ID NO: 1 or SEQ ID NO: 9.

In some aspects, one or more of $R_3$ and/or $R_4$ is a peptide. In some aspects, the peptide comprises a positively-charged moiety. In some aspects, the positively-charged moiety is an amino acid. In some aspects, the positively-charged moiety comprises about 10 positively-charged amino acids. The the positively-charged moiety can be a peptide comprising 10 lysine residues.

In some aspects, one or more of the $R_3$ and/or $R_4$ moieties is a protein. In some aspects, the protein is selected from: tumor targeting peptide (TTP), a human cancer peptide, or calreticulin protein. In some aspects, the protein is calreticulin protein to RNA-origami to engage interactions between tumor cells and macrophages or dendritic cells for enhanced antigen presentation and stimulation of antigen-specific T cells. In some aspects, the protein is Human cancer peptide NY-ESO-1 or Muc1. In some aspects, the TTP is CTKD-K10 having the sequence:

(SEQ ID NO: 3)
CTKDNNLLGRFELSGGGSKKKKKKKKKK.

In some aspects, this invention provides for a pharmaceutical composition comprising a RNA nanostructure robot described herein and a pharmaceutically acceptable carrier. In some aspects, the pharmaceutical composition further comprises at least one therapeutic agent.

In some aspects, this invention provides for a method of treating cancer in a subject, comprising administering to the subject a therapeutically effective amount of the composition described herein. In some aspects, the cancer is breast cancer, ovarian cancer, melanoma or lung cancer.

In some aspects, this invention provides for a method of inhibiting tumor growth in a subject, comprising administering to the subject a therapeutically effective amount of a composition described herein.

In some aspects, this invention provides for the use of the RNA nanostructure robot as described herein or a composition as described herein for the manufacture of a medicament for inducing a tumor necrosis response in a subject.

In some aspects, this invention provides for the use of the RNA nanostructure robot as described as described herein or a composition as described herein for inducing a tumor necrosis response.

In some aspects, this invention provides for the use of the RNA nanostructure robot as described as described herein or a composition as described herein for the manufacture of a medicament for treating a disease or disorder in a subject.

In some aspects, this invention provides for the use of the RNA nanostructure robot as described as described herein or a composition as described herein for the prophylactic or therapeutic treatment a disease or disorder.

As described herein, in certain aspects, the present invention provides an RNA nanostructure robot (also referred to herein as "RNA origami" or "OG-RNA" or "RNA-OG") which comprises:

a first nano-robot comprising a single stranded RNA (ssRNA) of about 1500 to 10,000 bases in length that self-assembles into a first scaffold; a second nano-robot comprising a ssRNA of about 1500 to 10,000 bases in length that self-assembles into a second scaffold; and a linker, wherein the linker operably links the first nano-robot to the second nano-robot.

In certain aspects, the present invention provides a pharmaceutical composition comprising the RNA nanostructure robot as described herein and a pharmaceutically acceptable carrier.

In certain aspects, the present invention provides a method of treating a disease or disorder in a subject, comprising administering to the subject a therapeutically effective amount of the RNA nanostructure robot or a composition as described herein.

In certain aspects, the present invention provides a method of inhibiting tumor growth in a subject, comprising administering to the subject a therapeutically effective amount of the RNA nanostructure robot or composition as described herein.

In certain aspects, the present invention provides a use of the RNA nanostructure robot or composition as described herein for the manufacture of a medicament for inducing a tumor necrosis response in a subject.

In certain aspects, the present invention provides a use of the RNA nanostructure robot or composition as described herein for inducing a tumor necrosis response.

In certain aspects, the present invention provides a use of the RNA nanostructure robot or composition as described herein for the manufacture of a medicament for treating a disease or disorder in a subject.

In certain aspects, the present invention provides a use of the RNA nanostructure robot or composition as described herein for the prophylactic or therapeutic treatment of a disease or disorder.

In certain aspects, the present invention provides a kit comprising the RNA nanostructure robot or composition as described herein and instructions for administering the RNA nanostructure robot/composition to a subject to induce an immune response or to treat a disease or disorder.

The invention also provides processes disclosed herein that are useful for preparing an RNA nanostructure described herein.

BRIEF DESCRIPTION OF THE FIGURES

FIG. 19A-FIG. 19C: FIG. 19A shows memory recalled responses. Splenocytes stimulated in vitro by PBS (Buffer), TPP, RNA-OG-TPP, Irrelevant (KLH) peptide, or RNA-OG; FIG. 19B shows representative ELISPOT readout, where each spot represents an IFNg-producing immune cell that was activated by different stimuli; and FIG. 19C shows quantification of ELISPOTS. Tumor-free mouse developed TPP-specific immunity as revealed by ELISPOT assay, in which TTP-stimulated splenocytes produced IFNg after the splenocyte cultured with TPP, but not irrelevant peptides.

FIG. 24 depicts a therapeutic agent-RNA conjugate capture strand having a ssRNA attachment strand and a therapeutic agent payload.

FIG. 25 depicts a therapeutic agent-RNA conjugate capture strand having a ssRNA attachment strand and a therapeutic agentpayload, where the therapeutic agentpayload is operably linked to an imaging agent.

FIG. 26 depicts a therapeutic agent-RNA conjugate capture strand having a ssRNA attachment strand that is a pH-sensitive linker.

FIG. 27 depicts a drug-RNA conjugate capture strand having a ssRNA attachment strand that is linked to a therapeutic agentpayload by means of a linker, where the therapeutic agentpayload is operably linked to an imaging agent.

FIG. 28 depicts an unfastened rectangular RNA origami structure having four therapeutic agent-RNA conjugates operably linked to the origami structure. The therapeutic agent-RNA conjugates can be attached to either the "top" or the "bottom" (or both) of the origami structure, such that when the origami structure is rolled into a tube, the drug-RNA conjugates can be designed to be either on the inside or outside of the tube.

FIG. 29 depicts an unfastened rectangular RNA origami structure having three drug-RNA conjugates operably linked to the origami structure. The drug-RNA conjugates can be attached to either the "top" or the "bottom" (or both) of the origami structure, such that when the origami structure is rolled into a tube, the drug-RNA conjugates can be designed to be either on the inside or outside of the tube.

FIG. 30 depicts an unfastened rectangular RNA origami structure having two drug-RNA conjugates operably linked to the origami structure. The drug-RNA conjugates can be attached to either the "top" or the "bottom" (or both) of the origami structure, such that when the origami structure is rolled into a tube, the drug-RNA conjugates can be designed to be either on the inside or outside of the tube.

FIG. 31 depicts an unfastened rectangular RNA origami structure having one drug-RNA conjugate operably linked to the origami structure. The drug-RNA conjugate can be attached to either the "top" or the "bottom" of the origami structure, such that when the origami structure is rolled into a tube, the drug-RNA conjugate can be designed to be either on the inside or outside of the tube.

DETAILED DESCRIPTION

Figure 1:
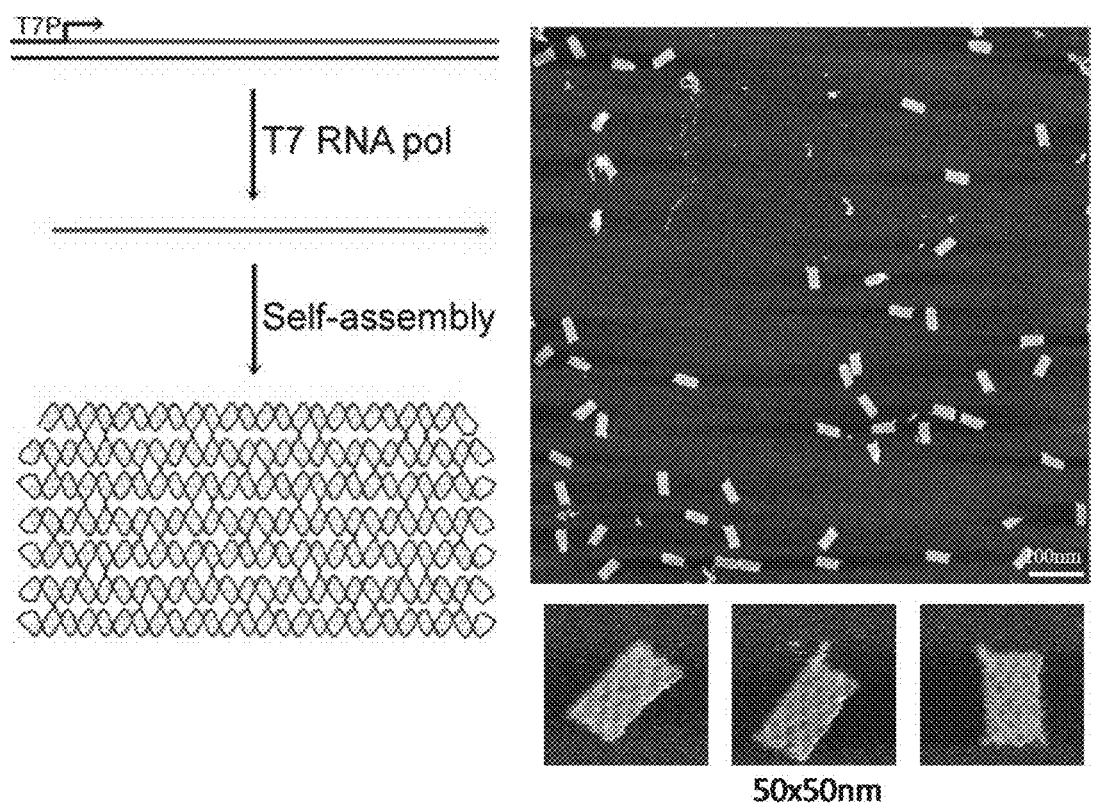
FIG. 1. RNA origami schematics (left panel) and AFM images (right panel). A plasmid containing a ssRNA origami gene was linearized and the ssRNA was in vitro transcribed using T7 RNA polymerase. The purified RNA molecule was self-assembled into the ssRNA rectangle origami nanostructure through paranemic cohesion crossover.

Double-stranded RNA (dsRNA) is a by-product of viral infection. It is a natural ligand of Toll-like receptor 3 (TLR3) and a potent stimulator for activating innate and adaptive immunity. PolyIC is a synthetic dsRNA analogue and has been widely explored for anti-cancer immunotherapy.

PolyIC, however, is associated with high toxicity, primarily due to excessive production of cytokines, which subsequently leads to cytokinemia. The adjuvant activity of RNA-origami was tested in cancer immunotherapy and it was found that repeat injections (e.g., 2, 3, 4, 5, 6, 7, or 8 injections, depending on the tumor load and intrinsic tumor immunogenicity) of RNA-origami at 16 µg/dose significantly delayed tumor growth. In certain embodiments, the dosage is less than about 5 mg/kg, less than about 4 mg/kg, less than about 3 mg/kg, less than about 2 mg/kg, less than about 1 mg/kg, or less than about 0.8 mg/kg. In addition, when the cytokine profiles were analyzed, it was found that the cytokines produced by the mice treated with RNA-origami had higher levels of particular cytokines and chemokines required for the generation of effective anti-tumor immunity, but lower levels of cytokines involved in systemic cytokine storm. Thus, RNA-origami can be used as effective and safe adjuvants. Further, it was demonstrated that the present RNA-origami exhibit potent anti-tumor activity, but without apparent toxicity.

TLR3 ligands have multiple modes of action in cancer therapy. They can be used as inducers of apoptosis/neprotosis in cancer cells. They are strong activators for the production of type-I interferon in a wide range of cell types, including host immune cells and cancer cells, via two major pathways: TLR3 (endo-lysosome) and MDA/RIG (present in cytoplasm). TLR3 ligands exhibit synergistic effects in combination with chemotherapeutics, apoptosis enhancers, other TLR ligands, tumor antigens, and checkpoint inhibitors (e.g., anti-PD1, CTLA4 or PD-L1). The same ligands are used for both murine models and for humans.

TLR3 ligands include PolyIC, Poly A:U and ARNAX. There are three types of PolyIC: (1) standard Poly-IC, which is rapidly inactivated by serum; (2) Poly-IC/poly-lysine (polyICLC, Hiltonol, Oncovir), which has been studied in 12 clinical trials for many malignant tumors; and (3) Poly (I:C12U) (Ampligen), which has been studied in clinical trials for OVC and peritoneal tumors. PolyIC has been tested in humans since the late 1970s as anti-cancer adjuvants. PolyIC, however, was found to be quickly inactivated by serum. Although its complex with poly-lysine greatly enhances its half-life in circulation and efficacy, complexed polyIC causes intolerable adversity, due to excessive production of cytokines. It is believed that polyIC activates both TLR3 and MDA5/RIG signaling pathways. The latter has been linked to systemic toxicity. Instead, polyIC has been explored as a part of cancer vaccines by mixing with tumor-specific antigens, which were delivered locally.

In addition, double-stranded poly A:U was tested in early 1980s in clinical studies. Due to its low efficacy (possibly labile) and poor cellular uptake, the efforts were discontinued. Recently, the interest on poly A:U investigation has been renewed because it was found that poly A:U only activates TLR3, but not the MDA/RIG signaling pathways, therefore causing low toxicity.

A third line of study involves ARNAX, which is phosphorothioate ODN-guided dsRNA (sODN-dsRNA) that resembles PolyA:U. It exhibits ODN-mediated cellular uptake. (Matsumoto, M. et al. 2015. Nature Communications. 6:6280) RNA-origami is advantageous over other TLR3 ligands for many reasons. For example, they are scalable in terms of quantity for production with relatively low cost. They have well-defined structure and uniformity for reproducibility. The particulate size and intrinsic RNA nanoparticle robot structure as described herein is superior for better internalization by immune cells without additional packaging to promote phagocytosis, like the processes involved in polyIC, dsRNA or the synthetic oligo-DNA-RNA hybrid (i.e., ARNAX). ARNAX activates endosomal toll-like receptor 3 (TLR3), but not cytoplasmic MDA5/RIG-I. The TLR3-TICAM-1-IRF3-IFN-β signaling axis is indispensable in dendritic cells (DCs) for ARNAX-mediated cytotoxic T lymphocyte (CTL) induction. (B) ARNAX therapy enhances antitumor responses in conjunction with PD-1/PD-L1 blockade. Tumors are self-originating and essentially lack an adjuvant. In the absence of adjuvant, DCs remain immature state (immature DC) and fail to induce tumor-associated antigen (TAA)-specific CTLs. ARNAX activates TLR3 in DCs to induce maturation and cross-priming of TAA-specific CTLs in lymphoid tissues. They are highly stable so as to be feasible for in vivo applications. The RNA nanoparticle robots as described herein have better safety as they may selectively activate a pathway (TLR3) that is required for an induction of adaptive cellular immunity (anti-cancer or anti-viral), but not MDA5/RIG pathway, and therefore are less likely to induce a cytokine storm. The RNA nanoparticle robots as described herein have well-defined structure and uniformity for reproducibility, unlike heterogenous population of polyIC (low vs high molecular weight) with different functional activities. Thus, the RNA nanoparticle robots as described herein have surprising stability, uptake, homogeneity, selectivity and low toxicity.

RNA Nanostructure Complexes

In some embodiments, this disclosure includes a RNA nanostructure robot (also referred to herein as "RNA origami" or "OG-RNA" or "RNA-OG") having the sequence of $(R_3)_n$-$NR_1$-L-$NR_2$-$(R_4)_m$, wherein:

$NR_1$ represents a first nano-robot comprising a single stranded RNA (ssRNA) of about 1500 to 10,000 bases in length that self-assembles into a first scaffold;

$NR_2$ represents a second nano-robot comprising a ssRNA of about 1500 to 10,000 bases in length that self-assembles into a second scaffold;

L is a linker which operably links $NR_1$ to $NR_2$;

wherein $R_3$ and $R_4$ are independently selected from a pair of fastener strands, an aptamer, a cargo molecule, a capture strand, a targeting strand, or H;

n is an integer from 0 to 50; and m is an integer from 0 to 50.

In certain embodiments, n is selected from 0, 1, 2, 3, 4, 5, 6, 7, 8, 9, 10, 11, 12, 13, 14, 15, 16, 17, 18, 19, and 20. In certain embodiments, m is selected from 0, 1, 2, 3, 4, 5, 6, 7, 8, 9, 10, 11, 12, 13, 14, 15, 16, 17, 18, 19, and 20. When n or m is 0, the $R_3$ or $R_4$ moiety is not present. When n is 2 or greater, there can be multiple separate $R_3$ moieties simultaneously present (e.g., one $R_3$ is an aptamer, another $R_3$ is a cargo molecular, another $R_3$ is a capture strand, etc.). When m is 2 or greater, there can be multiple separate $R_4$ moieties simultaneously present (e.g., one $R_4$ is an aptamer, another $R_4$ is a cargo molecular, another $R_4$ is a capture strand, etc.).

In certain embodiments, the linker is an oligonucleotide. The oligonucleotide can be comprised of DNA, RNA, modified DNA, modified RNA, or combinations thereof.

In certain embodiments, the present invention provides a complex comprising an RNA nanostructure and at least one diagnostic and/or therapeutic agent operably linked to the RNA nanostructure.

In certain embodiments, the RNA nanostructure comprises one single-stranded RNA (ssRNA) molecule, wherein the ssRNA molecule forms at least one paranemic cohesion crossover, and wherein the RNA nanostructure has immunostimulatory properties.

In certain embodiments, the RNA nanostructure comprises one single-stranded RNA (ssRNA) molecule, wherein the ssRNA molecule comprises a plurality of regions of double helices, wherein at least two of the plurality of regions of double helices form a paranemic cohesion crossover, and wherein the RNA nanostructure has immunostimulatory properties.

As used herein, the term "RNA nanostructure" refers to a nanoscale structure made of RNA, wherein the RNA acts both as a structural and function element. RNA nanostructures can also serve as a scaffold for the formation of other structures. RNA nanostructures may be prepared by methods using one or more nucleic acid oligonucleotides. For example, such nanostructures may be assembled based on the concept of base-pairing. While no specific sequence is required, the sequences of each oligonucleotide must be partially complementary to certain other oligonucleotides to enable hybridization of all strands or sequences within a single oligonucleotide to enable hybridization and assembly of the nanostructure. For example, in certain embodiments, the RNA nanostructure is an RNA rectangle origami nanostructure, self-assembled from one single-stranded RNA molecule through paranemic cohesion crossover.

As used herein, the term "nanorobot" or "RNA nanostructure robot" or "DNA nanostructure cage" refers to a RNA or DNA nanostructure which exhibits at least one function, which can be active and/or passive. The function can include or exclude delivery of a moiety $R_3$ or $R_4$. In some embodiments one or more of the $R_3$ and/or $R_4$ moieties is an agent. Active RNA nanostructure functions can include cage opening, wherein a folded RNA nanostructure opens in the presence of a stimulus. In some embodiments, the stimulus is the presence of a high localized concentration of a competitive binding partner to an aptamer or antibody present at the periphery of the RNA nanostructure sheet. Passive DNA and/or RNA nanostructure functions can include carrying and/or delivery of agents, either covalently or non-covalently. Passive nanostructure functions may also include release of a carried agent upon a stimulus. Covalently carrying agents can occur through the cross-linking of an amino-modified ribonucleotide with a peptide or protein through a bifunctional compound. The bifunctional compound can be sulfo-SMCC.

Non-covalently carrying agents can occur by hybridization of an agent comprising an oligonucleotide sequence which is partially complementary to the RNA nanostructure sequence. In some embodiments, delivery of agents can comprise encapsulation of an agent within a DNA cage.

In certain embodiments, the RNA nanostructure can be formed without the use of "staple strands." It was surprisingly found that in some embodiments, the RNA nanostructure can self-assemble with no added stable strands. In some embodiments, the DNA nanocage comprises staple strands. As used herein, "staple strands" are short single-stranded oligonucleotides of about 20 to about 40 nucleotides in length, such as 20, 21, 22, 23, 24, 25, 26, 27, 28, 29, 30, 31, 32, 33, 34, 35, 36, 37, 38, 39, or 40 nucleotides in length, wherein one end of the staple strand hybridizes with a region of the scaffold strand, and the second end of the staple strand hybridizes with another region of the scaffold strand, thereby "stapling" the two regions of the scaffold strand. In certain embodiments, the dimension of an RNA nanostructure sheet formed without the use of staple strands is about 90 nm×about 60 nm×2 nm.

In certain embodiments, one of more of $R_3$ and/or $R_4$ is an agents which may be operably linked to the RNA nanostructure, such as diagnostic agents or therapeutic agents. In certain embodiments, at least one diagnostic agent is operably linked to the RNA nanostructure. In certain embodiments, at least one therapeutic agent is operably linked to the RNA nanostructure. In certain embodiments, at least one diagnostic agent and at least one therapeutic agent are operably linked to the RNA nanostructure.

As used herein, the term "paranemic cohesion crossover" refers to a four-stranded nucleic acid complex containing a central dyad axis that relates two flanking parallel double helices" (Zhang et al. J. Am Chem. Soc. 2002). The strands are held together exclusively by Watson-Crick base pairing. The key feature of the structure is that the two adjacent parallel nucleic acid double helices form crossovers at every point possible. Hence, reciprocal crossover points flank the central dyad axis at every major or minor groove separation. In other words, paranemic cohesion crossover refers to Watson-Crick base pairing interactions between two parallel double helices comprising a central dyad axis.

The assembly of such RNA nanostructures may be based on base-pairing principles or other non-canonical binding interactions. For example, while no specific RNA sequence is required, regions of complementary within a single RNA molecule or between multiple RNA molecules may be used for assembly. Persons of ordinary skill in the art will readily understand and appreciate that the optimal sequence for any given RNA nanostructure will depend on the desired or intended shape, size, nucleic acid content, and intended use of such RNA structure. In certain embodiments, wherein the nanostructure comprises more than one ssRNA molecule (e.g. two or more oligonucleotides/polynucleotides), each ssRNA molecule may have a region that is complementary to a region on another ssRNA molecule to enable hybridization of the strands and assembly of the nanostructure. In certain other embodiments, wherein the nanostructure consists of a single ssRNA molecule (i.e., a single unimolecular RNA oligonucleotide/polynucleotide), regions within the molecule may be complementary to certain other regions within the molecule to enable hybridization and assembly of the nanostructure. RNA nanostructures produced in accordance with the present disclosure are typically nanometer-scale structures (e.g., having length scale of 1 to 1000 nanometers), although, in some instances, the term "nanostructure" herein may refer to micrometer-scale structures (e.g., assembled from more than one nanometer-scale or micrometer-scale structure). In some embodiments, a RNA nanostructure described herein has a length scale of 1 to 1000 nm, 1 to 900 nm, 1 to 800 nm, 1 to 700 nm, 1 to 600 nm, 1 to 500 nm, 1 to 400 nm, 1 to 300 nm, 1 to 200 nm, 1 to 100 nm or 1 to 50 nm. In some embodiments, a RNA nanostructure described herein has a length scale of greater than 1000 nm. In some embodiments, a RNA nanostructure described herein has a length scale of 1 micrometer to 2 micrometers.

In certain embodiments, the RNA nanostructure comprises, consists essentially of, or consists of multiple ssRNA molecules (e.g., more than one oligonucleotide/polynucleotide strands, such as two or more ssRNA molecules). In certain embodiments, the RNA nanostructure comprises two or more ssRNA molecules, which are capable of self-assembling (or configured to self-assemble) into a nanostructure. In certain embodiments, the RNA nanostructure is assembled from two or more ssRNA molecules through paranemic cohesion crossovers. Thus, in certain embodiments, the RNA nanostructure comprises two or more ssRNA molecules, wherein the ssRNA molecules self-assemble to form at least one paranemic cohesion crossover.

In certain embodiments, the RNA nanostructure comprises, consists essentially of, or consists of a single ssRNA molecule (i.e., one unimolecular oligonucleotide/polynucleotide strand). In certain embodiments, the RNA nanostructure is assembled using one ssRNA molecule (e.g., in certain embodiments one and only one, exactly one, or greater than zero and less than two).

In certain embodiments, the RNA nanostructure is comprised of one ssRNA molecule, which is capable of self-assembling into a nanostructure. In certain embodiments, the RNA nanostructure consists of one ssRNA molecule, which is capable of self-assembling into a nanostructure. In certain embodiments, the RNA nanostructure is assembled from one ssRNA molecule through paranemic cohesion crossovers. Thus, in certain embodiments, the RNA nanostructure comprises one single-stranded RNA (ssRNA) molecule, wherein the ssRNA molecule forms at least one paranemic cohesion crossover.

The length of each RNA strand is variable and depends on, for example, the type of nanostructure to be formed. In certain embodiments, the RNA nanostructure is comprised of multiple oligonucleotide strands. In certain embodiments, the RNA nanostructure is comprised of a single (i.e., unimolecular) oligonucleotide strand. In certain embodiments, the oligonucleotide or RNA strand is about 15 nucleotides in length to about 150,000 nucleotides in length, about 15 to about 7500 nucleotides in length, about 3000 to about 7000 nucleotides in length, about 5000 to about 7000 nucleotides in length, about 5500 to about 6500 nucleotides in length, about 15 to about 5000 nucleotides in length, about 15 to about 4000 nucleotides in length, about 15 to about 3000 nucleotides in length, about 250 to about 3000 nucleotides in length, about 500 to about 3000 nucleotides in length, about 1000 to about 3000 nucleotides in length, about 1500 to about 2500 nucleotides in length, or between any of the aforementioned nucleotide lengths. In certain embodiments, the at least one ssRNA molecule (i.e., oligonucleotide or RNA strand) is about 10 nucleotides in length to about 200,000 nucleotides in length, the at least one ssRNA molecule (i.e., oligonucleotide or RNA strand) is about 10 nucleotides in length to about 100,000 nucleotides in length, the at least one ssRNA molecule (i.e., oligonucleotide or RNA strand) is about 10 nucleotides in length to about 90,000 nucleotides in length, about 10 to about 80,000 nucleotides in length, about 10 to about 70,000 nucleotides in length, about 10 to about 60,000 nucleotides in length, about 10 to about 50,000 nucleotides in length, about 10 to about 40,000 nucleotides in length, about 10 to about 30,000 nucleotides in length, about 10 to about 25,000 nucleotides in length, or about 10 to about 20,000 nucleotides in length. In certain embodiments, the ssRNA molecule (i.e., oligonucleotide or RNA strand) is about 15 nucleotides in length to about 20,000 nucleotides in length, the ssRNA molecule (i.e., oligonucleotide or RNA strand) is about 15 nucleotides in length to about 10,000 nucleotides in length, about 15 to about 7500 nucleotides in length, about 3000 to about 7000 nucleotides in length, about 5000 to about 7000 nucleotides in length, about 1500 to about 6500 nucleotides in length, about 1000 to about 7000 nucleotides in length, about 5500 to about 6500 nucleotides in length, about 15 to about 5000 nucleotides in length, about 15 to about 4000 nucleotides in length, about 15 to about 3000 nucleotides in length, about 250 to about 3000 nucleotides in length, about 500 to about 3000 nucleotides in length, about 1000 to about 3000 nucleotides in length, or about 1500 to about 2500 nucleotides in length. In certain embodiments, the ssRNA molecule (i.e., oligonucleotide or RNA strand) is about 100, about 200, about 300, about 400, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, about 5100, about 5 5200, about 5300, about 5400, about 5500, about 5600, about 5700, about 5800, about 5900, about 6000, about 6100, about 6200, about 6300, about 6400, about 6500, about 6600, about 6700, about 6800, about 6900, about 7000, about 7100, about 7200, about 7300, about 7400, about 7500, about 7600, about 7700, about 7800, about 7900, about 8000, about 8100, about 8200, about 8300, about 8400, about 8500, about 8600, about 8700, about 8800, about 8900, about 9000, about 9100, about 9200, about 9300, about 9400, about 9500, about 9600, about 9700, about 9800, about 9900, about 10000, about 10100, about 10200, about 10300, about 10400, about 10500, about 10600, about 10700, about 10800, about 10900, about 11000, about 11000, about 11100, about 11200, about 11300, about 11400, about 11500, about 11600, about 11700, about 11800, about 11900, about 12000, about 12100, about 12200, about 12300, about 12400, about 12500, about 12600, about 12700, about 12800, about 12900 nucleotides in length, about 13000 nucleotides in length, about 14000 nucleotides in length, about 15000 nucleotides in length, about 16000 nucleotides in length, about 17000 nucleotides in length, about 18000 nucleotides in length, about 19000 nucleotides in length, about 20000 nucleotides in length, about 25000 nucleotides in length, about 30000 nucleotides in length, about 35000 nucleotides in length, about 40000 nucleotides in length, about 45000 nucleotides in length, about 50000 nucleotides in length, about 75000 nucleotides in length, about 100000 nucleotides in length, about 125000 nucleotides in length, about 150000 nucleotides in length, about 175000 nucleotides in length or about 200000 nucleotides in length.

In some embodiments, the RNA is synthesized de novo using chemical or biological methods. The RNA can be chemically synthesized in a step-wise manner. In some embodiments, the RNA can be synthesized using the cyanoethyl phosphoramidite method (Beaucage, S. L., and Caruthers, M. H., Tet. Let. 22:1859, 1981); nucleoside H-phosphonate method (Garegg et al., Tet. Let. 27:4051-4054, 1986; Froehler et al., Nucl. Acid. Res. 14:5399-5407, 1986; Garegg et al., Tet. Let. 27:4055-4058, 1986, Gaffney et al., Tet. Let. 29:2619-2622, 1988). These chemistries can be performed by a variety of automated oligonucleotide synthesizers available in the market, including the use of an in vitro transcription method. In some embodiments, the RNA is synthesized de novo by transcription.

In some embodiments, the ssRNA can comprise the sequence of:

$(HD_1\text{-}LD_1\text{-}HD_2\text{-}LD_2)_x$ wherein x is selected from 2 to 100, 2 to 500, 2 to 1000, 2 to 1500, 2 to 2000, 2 to 2500, 2 to 3000, or 2 to 3500, 2 to 4000, 2 to 4500, 2 to 5000, 2 to 5500, or 2 to 6000;

wherein $HD_1$ and $HD_2$ are each an RNA helical domain;

wherein $LD_1$ and $LD_2$ are each an RNA locking domain;

and further wherein the ssRNA sequence, when folded, exhibits at least one paranemic cohesion crossover. As discussed herein, the term "helical domain" is used interchangeably with the term "a region of a double helix". Additionally, the term "locking domain" is used interchangeably with the term "paranemic cohesion crossover". In certain embodiments, HD$_1$ and HD$_2$ independently comprise from about 5 to about 50 ribonucleotides. In certain embodiments, LD$_1$ and LD$_2$ independently comprise from about 5 to about 50 ribonucleotides.

In certain embodiments, the RNA nanostructure is assembled using a single stranded RNA molecule. In certain embodiments, the RNA nanostructure comprises both single stranded and double stranded regions. In certain embodiments, the ssRNA molecule comprises at least two parallel double helices. In certain embodiments, the ssRNA molecules comprises 2, 3, 4, 5, 6, 7, 8, 9, 10, 11, 12, 13, 14, 15, 16, 17, 18, 19, or 20 parallel double helices. In certain embodiments, in the self-assembled RNA nanostructure design, a majority (~95%) is double-stranded region, and only a small portion (~5%) represents single-stranded RNA.

In certain embodiments, the RNA nanostructure is comprised of one ssRNA molecule, which is capable of self-assembling into a nanostructure. In certain embodiments, the RNA nanostructure is assembled from one ssRNA molecule through paranemic cohesion crossovers. Thus, in certain embodiments, the RNA nanostructure comprises one single-stranded RNA (ssRNA) molecule, wherein the ssRNA molecule forms at least one paranemic cohesion crossover. In certain embodiments, the RNA nanostructures has at least one paranemic cohesion crossover. In certain embodiments, the RNA nanostructures has at least one to about 200 paranemic cohesion crossovers. In certain embodiments, the RNA nanostructures has at least 12 to about 100 paranemic cohesion crossovers. In certain embodiments, the RNA nanostructures has at least 20 to about 80 paranemic cohesion crossovers. In certain embodiments, the RNA nanostructures has at least 40 to about 60 paranemic cohesion crossovers. An RNA (e.g., a ssRNA molecule) may be designed to assemble into a double-stranded chain, resembling a large hairpin structure. That hairpin structure then assembles to form a structure containing paired double helices (or regions thereof) and paranemic cohesion crossovers. In certain embodiments, the RNA nanostructure comprises between about 1 to about 200 paranemic cohesion crossovers.

A "layer" of an RNA nanostructure, as used herein, refers to a planar arrangement of a portion of the RNA chain. In certain embodiments, an RNA nanostructure comprises 2 or more layers. In some embodiments, an RNA nanostructure may contain 2, 3, 4, 5, 6, 7, 8, 9, 10, or more layers, depending on the desired shape of the nanostructure. In certain embodiments, the paranemic cohesion crossovers direct the RNA chain to further assemble into the final structure. The paranemic cohesion crossovers within the bottom layer are designed to (or configured or sequence-coded to) base pair with their corresponding paranemic cohesion crossovers within the top layer, but without traversing through each other. In some embodiments, a nanostructure comprises a first layer comprising a plurality of double helices and a plurality of paranemic cohesion crossovers, wherein at least two regions of double helices of the first layer are separated from each other by a paranemic cohesion crossover, and a second layer comprising a plurality of double helices and a plurality of paranemic cohesion crossovers, wherein at least two regions of double helices of the second layer are separated from each other by a paranemic cohesion crossover, wherein a paranemic cohesion crossover of the first layer is hybridized to a paranemic cohesion crossover of the second layer.

In certain embodiments, the shape of the RNA nanostructure can include or exclude a polyhedron, a tube, a spheroid, or an elliptoid. In certain embodiments, the polyhedron can include or exclude a rectangle, diamond, tetrahedron, or triangle. In certain embodiments, the shape of the RNA nanostructure is, for example, a rectangle, a diamond, a tetrahedron, a triangle, or any other user-defined geometric shape. Persons of ordinary skill in the art will, after having studied the teachings herein, appreciate and understand that these teachings are not limited to any specific RNA nanostructure shape, but rather can be applied to generate any desired shape by programming (or generating) the RNA molecule with the requisite sequence that will cause the molecule to self-assemble through pairing interactions into the desired shape. In certain embodiments, the shape of the RNA nanostructure is a rectangle. In certain embodiments, the RNA nanostructure is an RNA rectangle nanostructure, self-assembled from one single-stranded RNA molecule through paranemic cohesion crossover. In some embodiments, the rectangle RNA nanostructure comprises at least one loop region (e.g., 13 loops regions). In certain embodiments, the loop regions comprise or consist of a sequence selected from the group consisting of UUUC (SEQ ID NO: 4), GGGAGGG (SEQ ID NO: 5), CCCUCCC (SEQ ID NO: 6), AAAGAAA (SEQ ID NO: 7), and UUUCUUU (SEQ ID NO: 8). In certain embodiments, at least 25% of the loop regions may comprise or consist of UUUC (SEQ ID NO: 4), of GGGAGGG, (SEQ ID NO: 5), of CCCUCCC (SEQ ID NO: 6), of AAAGAAA (SEQ ID NO: 7) or of UUUCUUU (SEQ ID NO: 8). In certain embodiments, at least 50% of the loop regions may comprise or consist of UUUC (SEQ ID NO: 4), of GGGAGGG (SEQ ID NO: 5), of CCCUCCC (SEQ ID NO: 6), of AAAGAAA (SEQ ID NO: 7) or of UUUCUUU (SEQ ID NO: 8). In certain embodiments, at least 75% of the loop regions may comprise or consist of UUUC (SEQ ID NO: 4), of GGGAGGG (SEQ ID NO: 5), of CCCUCCC (SEQ ID NO: 6), of AAAGAAA (SEQ ID NO: 7) or of UUUCUUU (SEQ ID NO: 8). In certain embodiments, all of the loop regions may comprise or consist of UUUC (SEQ ID NO: 4), of GGGAGGG (SEQ ID NO: 5), of CCCUCCC (SEQ ID NO: 6), of AAAGAAA (SEQ ID NO: 7) or of UUUCUUU (SEQ ID NO: 8).

In certain embodiments, the RNA nanostructure is a rectangle origami nanostructure. For example, in certain embodiments, the single stranded RNA molecule is SEQ ID NO:1, as described in Example 1. As described in the Examples, this nanostructure may be surprisingly used as an immune-adjuvant to boost an immune response, including inducing anti-tumor immunity. Advantageously, this adjuvant may be easily scaled up by biochemical production.

Accordingly, certain embodiments of the invention provide an RNA nanostructure comprising a nucleic acid sequence having at least about 60% sequence identity to SEQ ID NO:1. In certain embodiments, the RNA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1. In certain embodiments, the RNA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1. In certain embodiments, the RNA nanostructure comprises SEQ ID NO:1. In certain embodiments, the RNA nanostructure consists of SEQ ID NO:1.

In certain embodiments, the RNA nanostructure comprises one or more modified nucleic acids. The modified nucleic acids can be a modified ribonucleotide or ribonucleoside. In some embodiments, the modified ribonucleoside can be selected from the RNA-incorporated from, in part, 5-Aminoallyluridine-5'-Triphosphate (Trilink, N-1062), or Biotin-16-Aminoallyluridine-5'-Triphosphate (Trilink, N-5005).

In some embodiments, one or more of $R_3$ and/or $R_4$ can be a tumor-specific antigen. In certain embodiments, the tumor-specific antigen is TKD. It is understood that the tumor-specific antigens may be modified to enhance complex formation, to modulate RNA nanostructure: tumor specific antigen ratios and to operably link one or more agents. In certain embodiments, the tumor-specific antigen is TKD modified to add a C at the N-terminus. In certain embodiments, the tumor-specific antigen is TKD modified to add from 1 to 15 lysine residues at the C-terminus. In certain embodiments, the tumor-specific antigen is TKD modified to add 10 lysine residues at the C-terminus. In certain embodiments, the tumor-specific antigen is TKD modified to add a C at the N-terminus and from 1 to 15 lysine at the C-terminus. In certain embodiments, the tumor-specific antigen is TKD modified to add a C at the N-terminus and 10 lysine at the C-terminus.

In certain embodiments, one or more of $R_3$ and/or $R_4$ can be an agent. In some embodiments, one or more agents (e.g., 1 to 50, 2 to 50, 2 to 20, or any number of agents between the aforementioned numbers of agents) can be operably linked to the RNA nanostructure. In some embodiments, the agent can be selected from a diagnostic agents or therapeutic agents. In certain embodiments, at least one diagnostic agent is operably linked to the RNA nanostructure. In certain embodiments, at least one diagnostic agent is operably linked to the tumor-specific antigen. In certain embodiments, at least one therapeutic agent is operably linked to the RNA nanostructure. In certain embodiments, at least one therapeutic agent is operably linked to the tumor-specific antigen. In certain embodiments, at least one diagnostic agent and at least one therapeutic agent are operably linked to the RNA nanostructure. In certain embodiments, at least one diagnostic agent and at least one therapeutic agent are operably linked to the tumor-specific antigen.

Diagnostic agents include imaging agents, e.g., fluorophores, radioisotopes, and colorimetric indicators.

As used herein, the term "therapeutic agent" includes agents that provide a therapeutically desirable effect when administered to subject. The agent may be of natural or synthetic origin. For example, it may be a nucleic acid, a polypeptide, a protein, a peptide, a radioisotope, saccharide or polysaccharide or an organic compound, such as a small molecule. The term "small molecule" includes organic molecules having a molecular weight of less than about, e.g., 1000 daltons. In one embodiment a small molecule can have a molecular weight of less than about 800 daltons. In another embodiment a small molecule can have a molecular weight of less than about 500 daltons.

In certain embodiments, the therapeutic agent is an immuno-stimulatory agent, a radioisotope, a chemotherapeutic drug (e.g., doxorubicin) or an immuno-therapy agent, such as antibody or an antibody fragment. In certain embodiments, the therapeutic agent is a vaccine, such as a cancer vaccine. In certain embodiments, the therapeutic agent is a tumor targeting agent, such as a monoclonal tumor-specific antibody or an aptamer. In certain embodiments, the therapeutic agent is an antibody or fragment thereof. The antibody or fragment thereof can be selected from a monoclonal antibody, a polyclonal antibody, an ScFv, or a nanobody. In some embodiments, the antibody is an anti-PD1 antibody as described herein. In certain embodiments, the therapeutic agent is an antigen (e.g., a tumor associated antigen or a tumor specific antigen). In certain embodiments, the therapeutic agent is one or more tumor antigen peptide(s).

In some embodiments, the therapeutic agent is a chemotherapeutic agent. As used herein, the term "chemotherapeutic agent" refers to a biological (large molecule) or chemical (small molecule) compound useful in the treatment of cancer, regardless of mechanism of action. Classes of chemotherapeutic agents include, but are not limited to alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted conventional chemotherapy.

In certain embodiments, the therapeutic agent is a vasoconstrictor. In certain embodiments, the vasoconstrictor is selected from thrombin, prothrombin, rhThrombin, fragments thereof, and combinations thereof. In certain embodiments, the therapeutic agent is thrombin. In some embodiments, the thrombin can be human thrombin, bovine thrombin, or murine thrombin. In some embodiments, the thrombin can be thrombin alpha.

RNA Nanostructure Double-Robots

Folding nucleic acids into well-defined and compacted nanostructures, i.e., in nanometer scale (such as RNA origami described above), has been shown to improve their nuclease resistance and lower the toxicity. Thus, RNA origami with defined structure are used as a new adjuvant platform. Nucleic acid nanostructures are excellent nanoscaffolds for molecular-cargo delivery, such as for aptamers, proteins, and drug molecules. When conjugated with targeting compounds and molecular switches, the RNA origami co-delivers functional cargos to the desired locations with a triggered and delayed release.

The design of RNA nanostructure robots as described herein combines multiple functional devices into a single molecular robot for cancer immunotherapy. Moreover, RNA-based nanostructure double-robots can be produced in a large quantity at a low cost.

In some embodiments, RNA nanostructure double-robots were designed from single stranded RNA molecules ("ssRNA") (as described above), in which a tumor-targeting molecule, e.g., nucleolin-binding aptamer, is attached to the double-robot to allow this robot device targeted to the tumor microenvironment. In addition, the double-robot contains two functional modules, "$NR_1$" (RNA nanorobot-1) and "$NR_2$" (RNA nanorobot-2), which are linked by one or more linker L. In some aspects, the linker L is tubable. In some aspects, the tunable properties of the linker L are pH-responsiveness, where the linker is responsive to the relatively low pH in the tumor microenvironment. As defined herein, "low pH" is a pH below about 7, such as below about 6, below about 5, below about 4, below about 3 or below about 2. One module, $NR_1$, function as both immune-adjuvant and RNA nanostructure scaffold for antigen specific delivery and induction of antigen-specific immunity. In some embodiments, the other module, $NR_2$, deliver a first species of $R_4$, which is a functional cargo molecule. In some embodiments, the functional cargo molecule is a checkpoint inhibitor antagonist. In some embodiments, the checkpoint inhibitor antagonistarein a form of antibodies, aptamers, or drugs. The opening of this module is controlled by a second species of $R_4$, which can be an aptamer that is specifically binding to Interferon gamma (IFN-gamma) that is usually produced by activated T cells. However, local accumulation of IFN-gamma negatively regulates T cell function by upregulating PD1 expression on these activated T cells (Ribas, A. 2015. Adaptive Immune Resistance: How cancer protects from immune Attack. Cancer Discovery. 5: 914-919). Thus, the delayed release of anti-PD1 antibodies or aptamers from the RNA-nanocage robot in response to IFN-gamma effectively counteracts the checkpoint action without compromising the generation of tumor-specific immunity.

An RNA nanostructure robot was constructed with multiple functions using single-stranded RNA origami technology. In the first RNA nanorobot, $NR_1$, the RNA origami was loaded with tumor specific peptide antigens and was taken up by antigen presenting cells (APCs) upon intraperitoneal injection. This elicits strong anti-tumor immunity and eventually kills cancer cells. Certain embodiments provide a method of inducing an immune response in a subject (e.g., a mammal, such as a human), comprising administering to the subject an effective amount of an RNA nanostructure robot, complex or composition as described herein. Certain embodiments provide a method of enhancing/increasing pro-inflammatory cytokines in a subject (e.g., a mammal, such as a human), comprising administering to the subject a therapeutically effective amount of an RNA nanostructure robot, complex or composition as described herein. Certain embodiments provide a method of activating immune cells by specific triggering of TLR3 signaling pathway in a subject (e.g., a mammal, such as a human), comprising administering to the subject a therapeutically effective amount of an RNA nanostructure robot, complex or composition as described herein. In some embodiments, the second RNA nanobobot, $NR_2$, comprises an RNA origami cage loaded with checkpoint inhibitors and locked by IFN-gamma aptamers. The RNA origami cage contains nucleolin aptamers that direct the specific delivery to tumor site. Upon IFN-gamma release from T-cells, the RNA origami cage unlocks and releases the checkpoint inhibitors (either anti-PD1 antibodies or aptamers) to mitigate immunosuppression in the tumor microenvironment. The single-stranded RNA origami structures are designed to delivers aptamers, antibodies and drugs into tumor environment with a triggered and delayed release.

The immune system plays an important role in the development of a cancer cell from a normal cell. Thus, in some embodiments, the invention features a method comprising a RNA nanostructure comprising an agent that targets one or more immune system checkpoints. Immune system checkpoints are inhibitory signaling pathways modulated by checkpoint proteins that turn off immune system effectors cells, for example, T cells. Some embodiments of the invention can include, checkpoint inhibitor antagonists (also referred to as "immune-checkpoint inhibitors antagonists"), which target the checkpoint proteins. The target checkpoint proteins include, but are not limited to, indoleamine (2, 3)-dioxygenase (IDO); programmed cytotoxic T-lymphocyte antigen 4 (CTLA-4), programmed death-1 (PD-1); programmed death-ligand 1 (PD-L1); PD-L2; lymphocyte activation gene 3 (LAG3); and B7 homolog 3 (B7-H3).

In some embodiments, the checkpoint inhibitor antagonists bind to ligands or proteins that are found on any of the family of T cell regulators, such as CD28/CTLA-4. Targets of checkpoint inhibitor antagonists include, but are not limited to, receptors or co-receptors (e.g., CTLA-4; CD8) expressed on immune system effector or regulator cells (e.g., T cells); proteins expressed on the surface of antigen-presenting cells (i.e., expressed on the surface of activated T cells, including PD-1, PD-2, PD-L1 and PD-L2); metabolic enzymes or metabolic enzymes that are expressed by both tumor and tumor-infiltrating cells (e.g., indoleamine (IDO), including isoforms, such as IDO1 and IDO2); proteins that belong to the immunoglobulin superfamily (e.g., lymphocyte-activation gene 3, also referred to as LAG3); proteins that belong to the B7 superfamily (e.g., B7-H3 or homologs thereof;). B7 proteins are found on both activated antigen presenting cells and T cells.

Checkpoint inhibitor antagonists useful in the present invention include but are not limited to: Ipilimumab (Yervoy), Tremelimumab (formerly ticilimumab), Pidilizumab (CT-011), Nivolumab (BMS-936558), Lambrolizumab (MK-3475), MPDL3280A, BMS-936559, AMP-224, IMP321 (ImmuFact), MGA271, Indoximod, INCB024360, IMP321 (Immuntep®), BMS-986016, LAG525, MBG453, CA-170, JNJ-61610588, Endoblituzumab (MGA271), MGD009, 8H9, Lirilumab, IPH4102, CPI-444, MEDI9447, OMP-31M32, Trabedersen (AP12009), M7824, Galusertinib (LY2157299), IPI-549, Hu5F9-G4, TTI-621 (SIRPalphaFc), 9B12, MOXR 0916, PF08600, MED6383, MED10562, INCAGN01949, GSK3174998, TRX-518, BMS-986156, AMG 228, MEDI1873, MEDI6469, MK-4166, INCAGN01876, GWN323, JTX-2011, GSK3359609, MEDI-570, Utomilumab, Urelumab, ARGX-110, BMS-936561, MDX-1203, Varilumab, CP-870893, APX005M, ADC-1013, JNJ-64457107, SEA-CD40, R07009789, BMX-986205, Indoximod, Epacadostat, MEDI9197, pixatimod, NKTR-214, CB-1158, LTX-315, and AM0010.

The RNA nanostructure robots (linked double robots or single chain double robots) described herein offer unprecedented multi-functional capabilities, including 1) tumor-targeted delivery; 2) potent adjuvant platform for construction tumor-specific vaccines; and 3) programmable release of checkpoint inhibitors. In some embodiments, the programmable release of checkpoint inhibitors occurs by the inclusion of a RNA nanostructure which is in the form of a locked cage with internalized cargo compounds which opens in the presence of a targeted stimulus. Thus, this novel RNA-robot functions at both directions of the immune reactions, i.e., activating tumor-specific immunity as well as antagonizing tumor-associated immunosuppression, which should help synergize and maximize anti-tumor immunity.

Without being bound by theory, the RNA nanostructure robots activate tumor-specific immunity by presenting a tumor antigen peptide to effector T-cells on an immune cell. Effector T cells (also called regulatory T cells, or Treg cells, or suppressor T cells) are immune system cells that inhibit a T cell response and are important in leading to cell-mediated immunity. Effector T cells contain cell surface markers including CD25 (the IL-2 receptor), CD45RB, CTLA4 and FOXP3. A T cell response is an immune-type response that mediated through T cells. When T cells are activated, they will divide and generate more T cells (e.g. Th1 or Th2 cells, also called CD4+ cells or T helper cells; memory T cells; or cytotoxic T cells; also referred to as CTLs or CD8+ T cells). Once activated, T helper cells divide and generate cytokines that regulate or otherwise assist other immune system cells to elicit an immune system response. Memory T cells also generate additional effector T cells upon activation after previous exposure to an antigen. Cytotoxic T cells kill tumor cells when presented with a target that they recognize.

Immuno-Stimulatory RNA Nanostructure Robot

Certain embodiments of the invention provide an RNA nanostructure having immuno-stimulatory properties. As used herein, an immune-stimulatory RNA nanostructure stimulates the immune system by, for example, inducing activation or increasing activity of any components of the immune system, or by reducing inhibition of the immune system. In certain embodiments, the RNA nanostructure is an agonist of a pattern recognition receptor. As used herein, the terms "pattern recognition receptor" or "PRR" refer to proteins expressed by cells of the innate immune system, such as dendritic cells, macrophages, monocytes, neutrophils and epithelial cells, to identify two classes of molecules: pathogen-associated molecular patterns (PAMPs), which are associated with microbial pathogens, and damage-associated molecular patterns (DAMPs), which are associated with components of host's cells that are released during cell damage or death. PRRs also mediate the initiation of antigen-specific adaptive immune response and release of inflammatory cytokines. In certain embodiments, the PRR is a toll-like receptor (TLR) (e.g., TLR3 or TLR7).

Accordingly, certain embodiments provide an RNA nanostructure that is immuno-stimulatory. As used herein, an immuno-stimulatory RNA nanostructure stimulates the immune system thereby inducing activation or increasing activity of any components of the immune system. In some embodiments, the immune-stimulatory RNA structures described herein stimulate immune cell activation, boost anti-tumor immunity, increase anti-tumor (pro-inflammatory) cytokines and/or reduce immunosuppressive cytokines. For example, in some embodiments immuno-stimulatory RNA structures described herein: activate immune cells, e.g., T helper cells, T cells (including CD69+ activated T cells), dendritic cells, natural killer cells, macrophages, reprogram the cytokine microenvironment by, for example, decreasing levels of immunosuppressive cytokines e.g., TGF beta (TGFβ1, TGFβ2, IL10, and IL4 and/or increasing production of anti-tumor (pro-inflammatory) cytokines, for example, interferon gamma and TNF-alpha; inhibit or suppress tumor growth, cause tumor regression and/or induce tumor immunity; stimulate splenic B and T cells; or activate the TLR3-signaling pathway.

Stability

Figure 37:
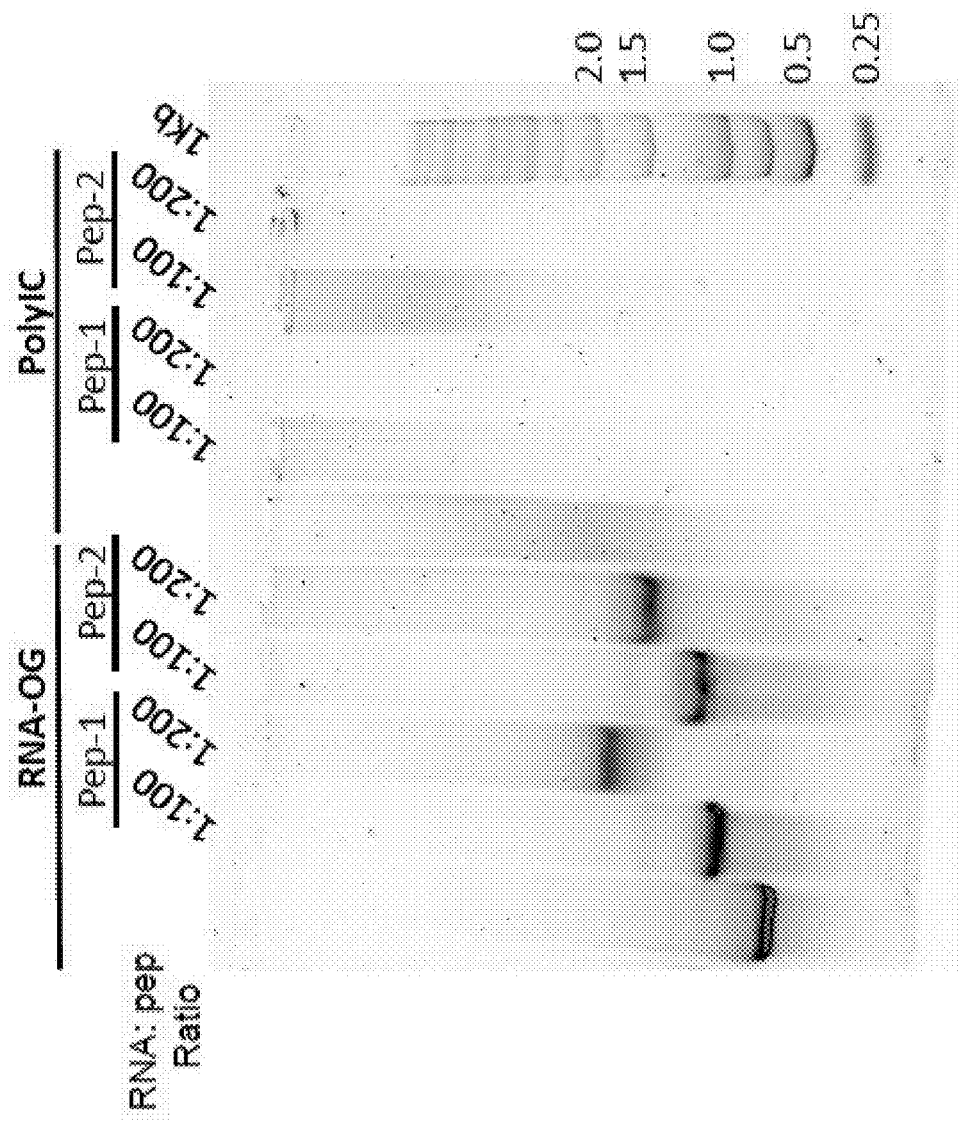
FIG. 37 depicts nondenaturing gel electrophoresis results of ssRNA nanostructure-peptide complexes demonstrating the solubility and stability of the complexes.

Antigen peptides in contact with the RNA nanostructures via a polylysine-RNA interaction exhibit enhanced stability over that of polylysine-polyIC complexes (FIG. 37). The enhanced stability of the polylysine-RNA nanostructures demonstrates that the RNA nanostructures circulate longer in the circulatory system after administration, resulting in a higher potency.

Nuclease Resistance

In certain embodiments, the RNA nanostructure robot has increased nuclease resistance (e.g., as compared to a control, such as an unfolded ssRNA molecule comprising the same nucleic acid sequence as the RNA nanostructure). In certain embodiments, nuclease resistance of the RNA nanostructure is about 10%, 20%, 30%, 40%, 50%, 60%, 70%, 80%, 90%, 95% or more than a control. The increased nuclease resistance enables the RNA nanostructure robot to circulate in the body longer after administration of a dose, resulting in higher potency of the dose.

Linkages

In some embodiments, the linkage between $NR_1$ to L, $NR_2$ to L, $NR_1$ to $R_3$, or $NR_2$ to $R_4$ is any group that can connect the $NR_1$ or $NR_2$ RNA nanostructure robots to each other or the moieties $R_3$ and/or $R_4$ using chemical methods, provided that the connection method does not interfere with the function of the $R_3$ and/or $R_4$ moieties or the RNA nanostructure. Chemistries that can be used to link the $R_3$ and/or $R_4$ moieties to an oligonucleotide can include or exclude: disulfide linkages, amino linkages, covalent linkages, etc. In certain embodiments, aliphatic or ethylene glycol linkers can be used. In certain embodiments phosphodiester, phosphorothioate and/or other modified linkages are used. In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate probe, IgG-protein A, antigen-antibody, aptamer-target and the like. In certain embodiments, a first member of the binding pair comprises avidin or streptavidin and a second member of the binding pair comprises biotin.

In some embodiments, the $R_3$ and/or $R_4$ moieties can comprise a loading oligonucleotide. In some embodiments, the loading oligonucleotide is designed to have all or a portion of the oligonucleotide sequence to be complementary to all or a portion of the ssRNA of $NR_1$ and/or $NR_2$. In some embodiments, the oligonucleotide sequence can comprise RNA, DNA, modified RNA, modified DNA, or combinations thereof. In some embodiments, the 5'- or 3'-ends of the oligonucleotide is modified with a oligonucleoside which can bind to a therapeutic and/or diagnostic agent. In some embodiments, the oligonucleotide is 5'-modified with a thiol-comprising nucleotide. In some embodiments, the thiol-comprising nucleotide is further reacted with a cross-functional linker. In some embodiments, the cross-functional linker is sulfo-SMCC ((sulfosuccinimidyl 4-(N-maleimidomethyl)cyclohexane-1-carboxylate), ThermoFisher cat. 22322). In some embodiments, the cross-functional linker is Sulfo-LC-SPDP (sulfosuccinimidyl 6-(3'-(2-pyridyldithio)propionamido)hexanoate) (ThermoFisher cat. 21650). In some embodiments, the sequence of the loading oligonucleotide is selected from the following loading oligonucleotide sequences:

```
TH-43
                               (SEQ ID NO: 124)
AAAAAAAAAAAAAAACAAAAATCATTGCTCCTTTTGATAAGTTTCAT;

TH-44
                               (SEQ ID NO: 125)
AAAAAAAAAAAAAAAAGATTCAGGGGGTAATAGTAAACCATAAAT;

TH-57
                               (SEQ ID NO: 39)
AAAAAAAAAAAAAAATTTGCCAGATCAGTTGAGATTTAGTGGTTTAA;

TH-64
                               (SEQ ID NO: 40)
AAAAAAAAAAAAAAGCAAATATCGCGTCTGGCCTTCCTGGCCTCAG;

TH-65
                               (SEQ ID NO: 41)
AAAAAAAAAAAAAAATATATTTTAGCTGATAAATTAATGTTGTATAA;

TH-78
                               (SEQ ID NO: 42)
AAAAAAAAAAAAAAACCGTTCTAAATGCAATGCCTGAGAGGTGGCA;
```

TH-139

(SEQ ID NO: 43)
AAAAAAAAAAAAAAAATTATTTAACCCAGCTACAATTTTCAAGAACG;

TH-140

(SEQ ID NO: 44)
AAAAAAAAAAAAAAGAAGGAAAATAAGAGCAAGAAACAACAGCCAT;

TH-153

(SEQ ID NO: 45)
AAAAAAAAAAAAAAAGCCCAATACCGAGGAAACGCAATAGGTTTACC;

TH-160

(SEQ ID NO: 46)
AAAAAAAAAAAAAAATAACCTCCATATGTGAGTGAATAAACAAAATC;

TH-161

(SEQ ID NO: 47)
AAAAAAAAAAAAAAACATATTTAGAAATACCGACCGTGTTACCTTTT;
or

TH-174

(SEQ ID NO: 48)
AAAAAAAAAAAAAAAATGGTTTACAACGCCAACATGTAGTTCAGCT.

Any of the aforementioned oligonucleotide sequences is 5' or 3' modified as described herein.

In some embodiments, the cross-functional compound can further be reacted with an agent. In some aspects, the agent is a protein or peptide comprising a lysine amino acid. The amine on the lysine can react with the amino-reactive cross-functional compound to form a loading oligonucleotide-functionalized agent. In some embodiments, the oligonucleotide-functionalized agent is hybridized to a portion or all of the ssRNA of $NR_1$ and/or $NR_2$.

In some embodiments, this invention provides for a RNA nanostructure robot, wherein the ssRNA sequence comprises a modified ribonucleic acid. The ribonucleic acid can comprise an alkyl amine functional group. In some embodiments, the amino-modified ribonucleoside is incorporated into the ssRNA sequence by the addition of 5-Aminoallyluridine-5'-Triphosphate during a transcription step of forming the ssRNA sequence.

In some embodiments, this invention provides for a RNA nanostructure robot, wherein wherein the therapeutic agent is a protein. The protein is selected from thrombin, prothrombin, or mixtures thereof. In some embodiments, the protein or peptide is conjugated to the amino-modified ribonucleotide by means of a cross-functional compound as described herein. In some embodiments, the maleimide group on the sulfo-SMCC can react to a cysteine on a non-reduced or reduced form of the thrombin molecule, and the sulfosuccinimidyl group on the sulfo-SMCC can react to the amino-modified ribonucleoside. In some embodiments, the maleimide group on the sulfo-SMCC can react to a loading oligonucleotide which has been modified to include a thiol-group to form a loading oligonucleotide-functionalized agent.

Compositions and Kits

Certain embodiments of the invention also provide a composition comprising an RNA nanostructure complex described herein and a carrier. In certain embodiments, the composition comprises a plurality of RNA nanostructures and a carrier.

In certain embodiments, the composition further comprises at least one therapeutic agent as described herein.

In certain embodiments, the composition is a pharmaceutical composition and the carrier is a pharmaceutically acceptable carrier.

Certain embodiments of the invention also provide a vaccine comprising an RNA nanostructure complex as described herein.

The present invention further provides kits for practicing the present methods.

Accordingly, certain embodiments of the invention provide a kit comprising an RNA nanostructure complex described herein and instructions for administering the RNA nanostructure to induce an immune response (e.g., anti-tumor immunity) or to treat a disease or condition. In certain embodiments, the kit further comprises a therapeutic agent described herein and instructions for administering the therapeutic agent in combination (e.g., simultaneously or sequentially) with the RNA nanostructure complex.

Certain Methods

An RNA nanostructure complex described herein may be used as an immune-adjuvant to boost an immune response (e.g., inducing anti-tumor immunity).

Accordingly, certain embodiments of the invention provide a method of inducing an immune response in a subject (e.g., a mammal, such as a human), comprising administering to the subject an effective amount of an RNA nanostructure complex or composition as described herein. In certain embodiments, the administration increases an immune response by at least about, e.g., 20%, 30%, 40%, 50%, 60%, 70%, 80%, 90%, or more (e.g., as compared to a control). Methods of measuring an immune response include using an assay described in the Example. The phrase "inducing an immune response" refers to the activation of an immune cell. Methods of measuring an immune response include using an assay described in the Example. The phrase "effective amount" means an amount of an RNA nanostructure described herein that induces an immune response.

Certain embodiments of the invention also provide a method of treating a disease or disorder in a subject, comprising administering to the subject a therapeutically effective amount of an RNA nanostructure complex or a composition as described herein.

In certain embodiments, a method of the invention further comprises administering at least one therapeutic agent to the subject.

The at least one therapeutic agent may be administered in combination with the RNA nanostructure. As used herein, the phrase "in combination" refers to the simultaneous or sequential administration of the RNA nanostructure and the at least one therapeutic agent. For simultaneous administration, the RNA nanostructure and the at least one therapeutic agent may be present in a single composition or may be separate (e.g., may be administered by the same or different routes).

Certain embodiments of the invention provide a RNA nanostructure complex or a composition as described herein for use in medical therapy.

Certain embodiments of the invention provide the use of an RNA nanostructure complex or a composition as described herein for the manufacture of a medicament for inducing an immune response in a subject (e.g., a mammal, such as a human).

Certain embodiments of the invention provide the use of an RNA nanostructure complex or a composition as described herein for the manufacture of a medicament for inducing an immune response in a subject (e.g., a mammal, such as a human), in combination with at least one therapeutic agent.

Certain embodiments of the invention provide an RNA nanostructure complex or a composition as described herein for inducing an immune response.

Certain embodiments of the invention provide an RNA nanostructure complex or a composition as described herein for inducing an immune response, in combination with at least one therapeutic agent.

Certain embodiments of the invention provide the use of an RNA nanostructure complex or a composition as described herein for the manufacture of a medicament for treating a disease or disorder in a subject.

Certain embodiments of the invention provide the use of an RNA nanostructure complex or a composition as described herein for the manufacture of a medicament for treating a disease or disorder in a subject, in combination with at least one therapeutic agent.

Certain embodiments of the invention provide an RNA nanostructure complex or a composition as described herein for the prophylactic or therapeutic treatment a disease or disorder.

Certain embodiments of the invention provide an RNA nanostructure complex or a composition as described herein for the prophylactic or therapeutic treatment of a disease or disorder, in combination with at least one therapeutic agent.

In certain embodiments, the disease or disorder is a condition that requires a boost of the host immunity. In certain embodiments, the disease or disorder is a hyperproliferative disorder, such as cancer. In certain embodiments, the disease or disorder is an infectious disease.

In certain embodiments, the cancer is carcinoma, lymphoma, blastoma, sarcoma, or leukemia. In certain embodiments, the cancer is a solid tumor cancer.

In certain embodiments, the cancer is squamous cell cancer, small-cell lung cancer, non-small cell lung cancer, adenocarcinoma of the lung, squamous carcinoma of the lung, cancer of the peritoneum, hepatocellular cancer, renal cell carcinoma, gastrointestinal cancer, gastric cancer, esophageal cancer, pancreatic cancer, glioma, cervical cancer, ovarian cancer, liver cancer, bladder cancer, hepatoma, breast cancer (e.g., endocrine resistant breast cancer), colon cancer, rectal cancer, lung cancer, endometrial or uterine carcinoma, salivary gland carcinoma, kidney cancer, liver cancer, prostate cancer, vulval cancer, thyroid cancer, hepatic carcinoma, melanoma, leukemia, or head and neck cancer. In certain embodiments, the cancer is breast cancer.

In certain embodiments, the therapeutic agent is a therapeutic agent described herein. For example, in certain embodiments, the therapeutic agent is an immuno-stimulatory agent, a radioisotope, a chemotherapeutic drug (e.g., doxorubicin) or an immuno-therapy agent, such as antibody or an antibody fragment. In certain embodiments, the therapeutic agent is a vaccine, such as a cancer vaccine. In certain embodiments, the therapeutic agent is a tumor targeting agent, such as a monoclonal tumor-specific antibody or an aptamer. In certain embodiments, the therapeutic agent is an antibody (e.g., a monoclonal antibody, e.g., an anti-PD1 antibody). In certain embodiments, the therapeutic agent is an antigen (e.g., a tumor associated antigen or a tumor specific antigen). In certain embodiments, the therapeutic agent is a tumor antigen peptide(s).

Administration

In some embodiments, methods of the invention comprise administering a RNA nanostructure described herein, and optionally, a therapeutic agent to a subject. Such compounds (i.e., a RNA nanostructure and/or therapeutic agent) may be formulated as a pharmaceutical composition and administered to a mammalian host, such as a human patient in a variety of forms adapted to the chosen route of administration, i.e., orally or parenterally, by intravenous, intramuscular, intraperitoneal or topical or subcutaneous routes.

The active compound may be administered intravenously or intraperitoneally by infusion or injection. Solutions of the active compound or its salts is prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle is a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity is maintained, for example, by the formation of liposomes, by the maintenance of the required particle size in the case of dispersions or by the use of surfactants. The prevention of the action of microorganisms is brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions is brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Pharmaceutical compositions for use in accordance with the present invention may be formulated using one or more physiologically acceptable carriers or excipients. Any suitable concentration of the RNA nanostructure robot may be used, and any active pharmaceutical ingredient will be administered in an amount effective to achieve its intended purpose.

A variety of suspending fluids or carriers may be employed to suspend the RNA nanostructure robot composition. Such fluids include without limitation: sterile water, saline, buffer, or complex fluids derived from growth medium or other biological fluids. Preservatives, stabilizers and antibiotics may be employed in the RNA nanostructure robot composition.

Methods of making a pharmaceutical composition include admixing at least one active compound or agent, as defined above, together with one or more other pharmaceutically acceptable ingredients, such as carriers, diluents, excipients, and the like. When formulated as discrete units, such as tablets or capsule or suspension, each unit contains a predetermined amount of the active compound or agent.

Suitable formulations will depend on the method of administration. The pharmaceutical composition is preferably administered by intradermal administration, but other routes of administration include for example oral, buccal, rectal, parenteral, intramuscular, subcutaneous, intraperitoneal, transdermal, intrathecal, nasal, intracheal. The polyvalent vaccine can also be administered to the lymph nodes such as axillary, inguinal or cervial lymph nodes. The active agent may be systemic after administration or may be localized by the use of regional administration, intramural administration, or use of an implant that acts to retain the active dose at the site of implantation.

Pharmaceutical compositions described herein may be administered directly, they may also be formulated to include at least one pharmaceutically-acceptable, nontoxic carriers of diluents, adjuvants, or non-toxic, nontherapeutic, fillers, buffers, preservatives, lubricants, solubilizers, surfactants, wetting agents, masking agents, and coloring agents. Also, as described herein, such formulation may also include other active agents, for example, other therapeutic or prophylactic agents, nonimmunogenic stabilizers, excipients and the like. The compositions can also include additional substances to approximate physiological conditions, such as pH adjusting and buffering agents, toxicity adjusting agents, wetting agents and detergents.

Adjuvants can include or exclude: polymers, copolymers such as polyoxyethylene-polyoxypropylene co-polymers, including block co-polymers; polymer P1005; monotide ISA72; Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; water-in-oil mixtures, water-in-oil-in-water mixtures or combinations thereof.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds is dissolved or dispersed at effective levels, optionally with the aid of non-toxic surfactants. Adjuvants such as fragrances and additional antimicrobial agents is added to optimize the properties for a given use. The resultant liquid compositions is applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dermatological compositions which can be used to deliver a compound to the skin are can include or exclude, for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference herein in their entirety.

Useful dosages of compounds can be determined by comparing their in vitro activity, and in vivo activity in animal models. Methods for the extrapolation of effective dosages in mice, and other animals, to humans are known to the art; for example, see U.S. Pat. No. 4,938,949, herein incorporated by reference.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound may be conveniently formulated in unit dosage form. In one embodiment, the invention provides a composition comprising a compound formulated in such a unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Certain Definitions

As used herein, the term "about" means±10%.

"Operably-linked" refers to the association two chemical moieties so that the function of one is affected by the other, e.g., an arrangement of elements wherein the components so described are configured so as to perform their usual function.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing synthetic analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The terms "nucleotide sequence", "polynucleic acid", or "nucleic acid sequence" refer to a sequence of bases (purines and/or pyrimidines) in a polymer of DNA or RNA, which can be single-stranded or double-stranded, optionally containing synthetic, non-natural or altered nucleotide bases capable of incorporation into DNA or RNA polymers, and/or backbone modifications (e.g., a modified oligomer, such as a morpholino oligomer, phosphorodiamate morpholino oligomer or vivo-mopholino). The terms "oligo", "oligonucleotide" and "oligomer" may be used interchangeably and refer to such sequences of purines and/or pyrimidines. The terms "modified oligos", "modified oligonucleotides", "modified oligomers", "modified ribonucleosides" or "modified ribonucleotides" may be similarly used interchangeably, and refer to such sequences that contain synthetic, non-natural or altered bases and/or backbone modifications.

In some embodiments, the modified oligos can comprise chemical modifications to the internucleotide phosphate linkages and/or to the backbone sugar.

Modified nucleotides can include or exclude: alkylated purines and/or pyrimidines; acylated purines and/or pyrimidines; or other heterocycles. These classes of pyrimidines and purines can include or exclude: pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylp-seudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; 3-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine. Backbone modifications are can include or exclude: chemical modifications to the phosphate linkage (e.g., phosphorodiamidate, phosphorothioate (PS), N3'phosphoramidate (NP), boranophosphate, 2',5'phosphodiester, amide-linked, phosphonoacetate (PACE), morpholino, peptide nucleic acid (PNA) and inverted linkages (5'-5' and 3'-3' linkages)) and sugar modifications (e.g., 2'-O-Me, UNA, LNA).

The oligonucleotides described herein may be synthesized using standard solid or solution phase synthesis methods. In certain embodiments, the oligonucleotides are synthesized using solid-phase phosphoramidite chemistry (U.S. Pat. No. 6,773,885) with automated synthesizers. Chemical synthesis of nucleic acids allows for the production of various forms of the nucleic acids with modified linkages, chimeric compositions, and nonstandard bases or modifying groups attached in chosen places through the nucleic acid's entire length.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

By "portion" or "fragment," as it relates to a nucleic acid molecule, sequence or segment of the invention, when it is linked to other sequences for expression, is meant a sequence having at least 80 nucleotides, at least 150 nucleotides, or at least 400 nucleotides. If not employed for expressing, a "portion" or "fragment" means at least 9, at least 12, at least 15, or at least 20, consecutive nucleotides, e.g., probes and primers (oligonucleotides), corresponding to the nucleotide sequence of the nucleic acid molecules of the invention.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press (3rd edition, 2001).

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleotide sequences: "reference sequence," "comparison window," "sequence identity," "percentage of sequence identity," "substantial identity," and "complementarity".

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally is 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison can be performed. Thus, the determination of percent identity, including sequence complementarity, between any two sequences is accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms is utilized for comparison of sequences to determine sequence identity or complementarity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575. Science Drive, Madison, Wis., USA). Alignments using these programs is performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score is increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) is utilized. Alternatively, PSI-BLAST (in BLAST 2.0) is used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) is used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

As used herein, the terms "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection.

As used herein, the term, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, the term "identity" or "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that is accommodated by reducing the stringency of the hybridization media to achieve the desired detection of the target nucleic acid sequence.

The term "complementary" as used herein refers to the broad concept of complementary base pairing between two nucleic acids aligned in an antisense position in relation to each other. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, at least about 60%, or at least about 80% of corresponding positions in each of the molecules are occupied by nucleotides which normally base pair with each other (e.g., A:T (A:U for RNA) and G:C nucleotide pairs).

As used herein, the term "derived" or "directed to" with respect to a nucleotide molecule means that the molecule has complementary sequence identity to a particular molecule of interest.

As used herein, the term "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

As used herein, the term "subject" as used herein refers to humans, higher non-human primates, rodents, domestic, cows, horses, pigs, sheep, dogs and cats. In one embodiment, the subject is a human.

As used herein, the terms "treat" and "treatment" refer to both therapeutic treatment and prophylactic or preventative measures, wherein the object is to prevent or decrease an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

Figure 12:
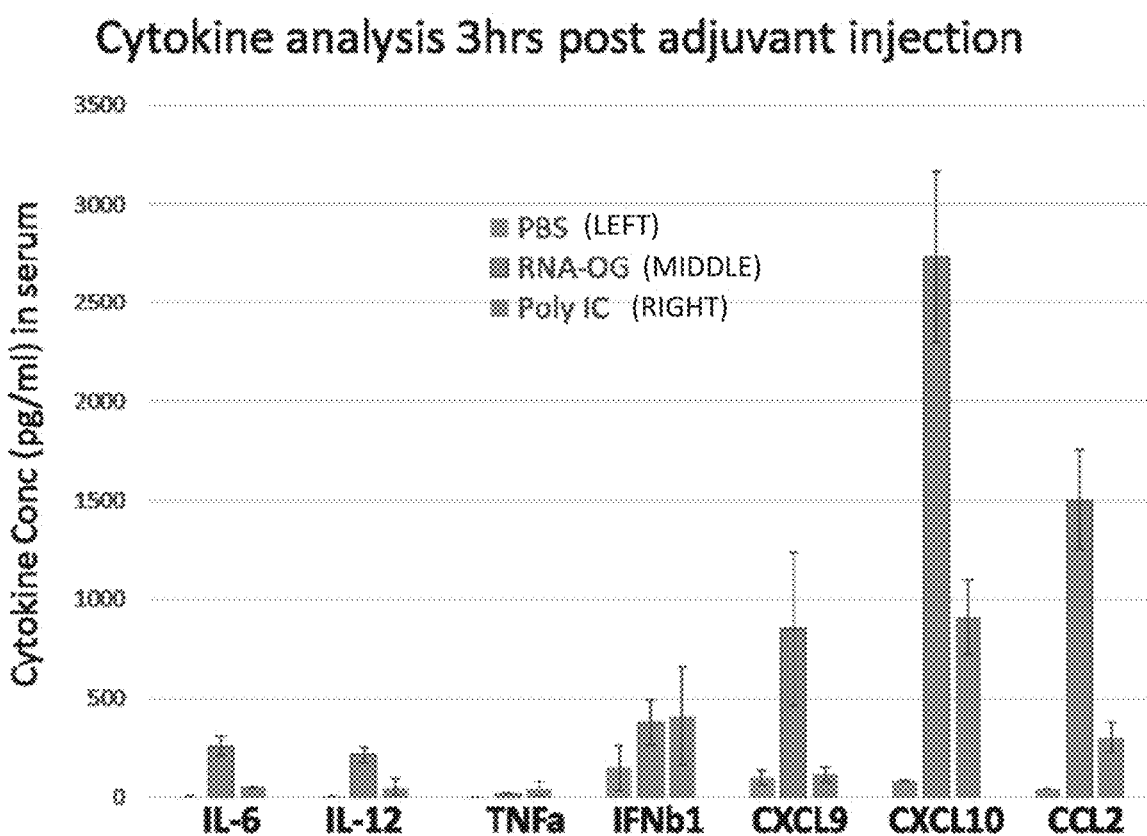
FIG. 12. Cytokines and chemokines three hours after IP treatment. PBS is the left columns in each cytokine set; RNA-OG is the middle column in each cytokine set, and poly IC is the right column in each cytokine set.

As used herein, the term "synergistic" as used herein refers to a therapeutic combination that is more effective than the additive effects of the two or more single agents. A determination of a synergistic interaction between an RNA-origami and one or more chemotherapeutic agent may be based on the results obtained from the assays described herein. The results of these assays can be analyzed using the Chou and Talalay combination method and Dose-Effect Analysis with CalcuSyn software in order to obtain a Combination Index (Chou and Talalay, 1984, Adv. Enzyme Regul. 22:27-55). The combinations provided by this invention can be evaluated in several assay systems, and the data can be analyzed utilizing a standard program for quantifying synergism, additivism, and antagonism among anticancer agents. The program utilized, for example in FIG. 12, is that described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together. In some examples, Combination effects were evaluated using both the BLISS independence model and the highest single agent (HSA) model (Lehir et al. 2007, Molecular Systems Biology 3:80). BLISS scores quantify degree of potentiation from single agents and a BLISS score >0 suggests greater than simple additivity. An HSA score >0 suggests a combination effect greater than the maximum of the single agent responses at corresponding concentrations.

Response Evaluation Criteria in Solid Tumors, Version 1.1 (RECIST v1.1), can be used to evaluate tumor responses in certain human clinical trials. This section provides the definitions of the criteria used to determine objective tumor response for target lesions. "Complete response" (CR) is used to mean disappearance of all observable target lesions with pathological lymph nodes (whether target or non-target) having reduction in short axis to less than about 10 mm. "Partial response" (PR) is used to mean at least about a 30% decrease in the sum of diameters of target lesions, taking as reference the baseline sum of diameters. "Progressive disease" (PD) is used to mean at least about a 20% increase in the sum of diameters of target lesions, taking as reference the smallest sum on study (nadir), including baseline. In addition to the relative increase of about 20%, the sum also demonstrates an absolute increase of at least about 5 mm. In one example, the appearance of one or more new lesions is considered PD. "Stable disease" (SD) is used to mean neither sufficient shrinkage to qualify for PR nor sufficient increase to qualify for PD, taking as reference the smallest sum on study.

Adverse Event Grading (Severity) Scale is used to evaluate safety and tolerability with Grade 1 is mild (intervention not indicated), Grade 2 is moderate (minimal, local, or noninvasive intervention indicated), Grade 3 is severe (severe or medically significant but not immediately life threatening; hospitalization or prolongation of hospitalization indicated), Grade 4 is very severe, life threatening or disabling, urgent intervention indicated, and Grade 5 is death related to the adverse event.

EMBODIMENTS OF THE INVENTION

In some embodiments, the present invention provides a RNA nanostructure robot having the sequence of $(R_3)_n$—$NR_1$-L-$NR_2$—$(R_4)_m$, wherein:
- $NR_1$ represents a first nano-robot comprising a single stranded RNA (ssRNA) of about 1500 to 10,000 bases in length that self-assembles into a first scaffold;
- $NR_2$ represents a second nano-robot comprising a ssRNA of about 1500 to 10,000 bases in length that self-assembles into a second scaffold;
- L is a linker which operably links $NR_1$ to $NR_2$;
- wherein $R_3$ and $R_4$ are independently selected from a pair of fastener strands, an aptamer, a cargo molecule, a capture strand, a targeting strand, or H;
- n is an integer from 0 to 20; and
- m is an integer from 0 to 20.

In certain embodiments, the linker L is an oligonucleotide. The oligonucleotide is comprised of DNA, RNA, modified DNA, modified RNA, or combinations thereof.

In certain embodiments, the RNA nanostructure robot is a single motif, where the sequence $NR_1$-L-$NR_2$ is continuous. The $NR_1$-L-$NR_2$ sequence can be transcribed as a single chain (ssRNA). In alternative embodiments, the RNA nanostructure is comprised of two or more motifs, wherein the first nano-robot comprises a first motif, and the second nano-robot comprises a second motif. In some embodiments, the first and second motifs is separately transcribed as two separate RNA chains. Portions of the two separate RNA chains can be hybridized to each other to form a linker, L. In some embodiments, the hybridization is a direct hybridization between a portion of the first RNA chain which is complementary to a portion of the second RNA chain. In some embodiments, the hybridization is an indirect hybridization via a bridge oligonucleotide wherein a portion of the sequence of one terminus of the bridge oligonucleotide is complementary to a portion of the sequence of the first RNA chain, and a sequence of the other terminus of the bridge oligonucleotide is complementary to a portion of the sequence of the second RNA chain, wherein hybridization occurs between portions of each of the first and second RNA chains and the bridging oligonucleotide. In certain embodiments, the linker is pH-sensitive. The RNA duplex linked to double nanobots can be responsive to an acidic environment for dehybridization. RNA duplex stability is pH sensitive as a lower pH is reduces the melting temperature of short RNA-duplexes.

In certain embodiments, the present invention provides for a RNA nanostructure as described herein where the first scaffold self-assembles into a rectangular shape.

In certain embodiments, the present invention provides for a RNA nanostructure robot that further comprises a moiety $R_4$, wherein $R_4$ is a cargo molecule. In some embodiments, $R_4$ is a cargo molecule and m is an integer from 1 to 20.

The cargo molecule can be an aptamer, protein, or drug molecule. In some embodiments, the protein is an antigen. In some embodiments, the cargo molecule is operably linked to $NR_2$.

In some embodiments, $R_4$ is a fastener strand of DNA. As used herein, the term "fastener strand" is a polynucleic acid which can enforce the first or second RNA nanostructure scaffold into a 3-D shape ("origami structure"). In some embodiments, $R_4$ is a pair of fastener strands which comprise DNA, and the pair of fasteners strands are capable of fastening the first or second scaffold into an origami structure, and n is an integer from 1 to 20. In some embodiments, the fastener strand can comprise an aptamer which binds to a locking protein. In some aspects, the locking protein is selected from: interferon-gamma (IFN-7), VEGF, and IDO. For example, in some embodiments, VEGF aptamers are attached to the RNA nanocage, in which anti-VEGF-Receptor antibodies are encaged. Similarly, if an aptamer that binds IDO were attached to the structure, IDO inhibitors are encaged within the RNA-cage. In some embodiments, the fastener strands comprises a first strand and a second strand, wherein the second strand of DNA comprises a sequence which is partially complementary to the sequence of the first strand. Each of the fastener strands of DNA can comprise a first and a second strand of DNA. In some embodiments, a portion of one terminus of the first strand of fastener DNA is complementary to a portion of one terminus of a second strand of DNA. A portion of the other terminus of the first strand of fastener DNA is complementary to a portion of the ssRNA of $NR_1$ or $NR_2$. In some embodiments, a portion of one terminus of the second strand of fastener DNA is complementary to a different portion of the ssRNA of $NR_1$ or $NR_2$. The fastener strands hybridize with their respective complements thereby configuring the RNA nanostructure into a 3-dimensional shape as described herein ("RNA origami"). The first and second strand of DNA can be selected from a sequence pair of the following oligonucleotides:

```
5'-FITC-labeled F50 and 3'-BHQ1-labeled Comp15;
FITC-F50-48 and Comp15-48-Q;
FITC-F50-73 and Comp15-73-Q;
FITC-F50-97 and Comp15-97-Q;
FITC-F50-120 and Comp15-120-Q;
FITC-F50-144 and, Comp15-144-Q; or
FITC-F50-169 and Comp15-169-Q;
wherein the aforementioned oligonucleotides
have the following sequences:
5'-FITC-labeled F50:
                                  (SEQ ID NO: 10)
5'-FITC-GGTGGTGGTGGTTGTGGTGGTGGTGGTCTAAAGTTTTGTCGT

GAATTGCG-3';

3'-BHQ1-labeled Comp15:
                                  (SEQ ID NO: 11)
5'-GTAAAGCTTTTTTTTTTTACAACCACCACCACC-3';

FITC-F50-48:
                                  (SEQ ID NO: 12)
5'-FITC-GGTGGTGGTGGTTGTGGTGGTGGTGGTCTAAAGTTTTGTCGT

GAATTGCG-3';
```

-continued

Comp15-48-Q:
(SEQ ID NO: 13)
5'-GTAAAGCTTTTTTTTTTTACAACCACCACCACC-BHQ1-3';

FITC-F50-73
(SEQ ID NO: 14)
5'-FITC-GGTGGTGGTGGTTGTGGTGGTGGTGGTAGAGCTTGACGGGGA

AATCAAAA-3';

Comp15-73-Q:
(SEQ ID NO: 15)
5'-TGTAGCATTTTTTTTTTTACAACCACCACCACC-BHQ1-3';

FITC-F50-97:
(SEQ ID NO: 16)
5'-FITC-GGTGGTGGTGGTTGTGGTGGTGGTGGCGAGAAAGGAAGGGAA

CAAACTAT-3';

Comp15-97-Q:
(SEQ ID NO: 17)
5'-TGAGTTTCTTTTTTTTTTTACAACCACCACCACC-BHQ1-3';

FITC-F50-120:
(SEQ ID NO: 18)
5'-FITC-GGTGGTGGTGGTTGTGGTGGTGGTGGATAGGAACCCATGTAC

AAACAGTT-3';

Comp15-120-Q:
(SEQ ID NO: 19)
5'-CAAGCCCATTTTTTTTTTTACAACCACCACCACC-BHQ1-3';

FITC-F50-144:
(SEQ ID NO: 20)
5'-FITC-GGTGGTGGTGGTTGTGGTGGTGGTGGCACCACCCTCATTTTC

CTATTATT-3';;

Comp15-144-Q:
(SEQ ID NO: 21)
5'-CCGCCAGCTTTTTTTTTTACAACCACCACCACC-BHQ1'-3';

FITC-F50-169:
(SEQ ID NO: 22)
5'-FITC-GGTGGTGGTGGTTGTGGTGGTGGTGGCTACATTTTGACGCTC

ACCTGAAA-3';

Comp15-169-Q:
(SEQ ID NO: 23)
5'-CCCTCAGTTTTTTTTTTTACAACCACCACCACC-BHQ1-3'.

In some embodiments, this disclosure provides for a RNA nanostructure robot wherein the first and second strands of fastener DNA are selected from a sequence pair of the following oligonucleotides:

F50 and Comp15;
F50-48 and Comp15-48;
F50-73 and Comp15-73;
F50-97 and Comp15-97;
F50-120 and Comp15-120;
F50-144 and, Comp15-144; or
F50-169 and Comp15-169;
wherein the aforementioned oligonucleotides
have the following sequences:
F50:
(SEQ ID NO: 24)
5'-GGTGGTGGTGGTTGTGGTGGTGGTGGTCTAAAGTTTTGTCGTGA

ATTGCG-3';

Comp15:
(SEQ ID NO: 25)
5'-GTAAAGCTTTTTTTTTTTACAACCACCACCACC-3';

F50-48:
(SEQ ID NO: 26)
5'-GGTGGTGGTGGTTGTGGTGGTGGTGGTCTAAAGTTTTGTCGTGA

ATTGCG-3';

Comp15-48:
(SEQ ID NO: 27)
5'-GTAAAGCTTTTTTTTTTTTACAACCACCACCACC-3';

F50-73
(SEQ ID NO: 28)
5'-GGTGGTGGTGGTTGTGGTGGTGGTGGTAGAGCTTGACGGGGAAA

TCAAAA-3';

Comp15-73:
(SEQ ID NO: 29)
5'-TGTAGCATTTTTTTTTTTACAACCACCACCACC-3';

F50-97:
(SEQ ID NO: 30)
5'-GGTGGTGGTGGTTGTGGTGGTGGTGGCGAGAAAGGAAGGGAACA

AACTAT-3';

Comp15-97:
(SEQ ID NO: 31)
5'-TGAGTTTCTTTTTTTTTTTACAACCACCACCACC-3';

F50-120:
(SEQ ID NO: 32)
5'-GGTGGTGGTGGTTGTGGTGGTGGTGGATAGGAACCCATGTACAA

ACAGTT-3';

Comp15-120:
(SEQ ID NO: 33)
5'-CAAGCCCATTTTTTTTTTTACAACCACCACCACC-3';

F50-144:
(SEQ ID NO: 34)
5'-GGTGGTGGTGGTTGTGGTGGTGGTGGCACCACCCTCATTTTCCT

ATTATT-3';;

Comp15-144:
(SEQ ID NO: 35)
5'-CCGCCAGCTTTTTTTTTTTACAACCACCACCACC-3';

F50-169:
(SEQ ID NO: 36)
5'-GGTGGTGGTGGTTGTGGTGGTGGTGGCTACATTTTGACGCTCAC

CTGAAA-3';

Comp15-169:
(SEQ ID NO: 37)
5'-CCCTCAGTTTTTTTTTTTACAACCACCACCACC-3'.

In some embodiments, one or more of R3 and/or R4 is an aptamer that specifically binds a target molecule and comprises domain which comprises a sequence which is partially complementary to the sequence of the second strand, and m is an integer from 1 to 20.

In some embodiments, one or more of $R_3$ and/or $R_4$ is an RNA targeting strand, wherein each targeting strand is operably linked to a targeting moiety and to $NR_1$ or $NR_2$. As used herein, the term "targeting strand" is a polynucleic acid which can comprise an aptamer sequence. The polynucleic acid can further comprise DNA, RNA, modified DNA, modified RNA, or combinations thereof. The targeting moiety can be an aptamer that specifically binds a target molecule. In some embodiments, the aptamer is specific for nucleolin. In some embodiments, the aptamer that is specific for nucleolin is an F50 AS1411 aptamer having the sequence:

(SEQ ID NO: 38)
5'-GGTGGTGGTGGTTGTGGTGGTGGTGG-3'.

In some embodiments, the aptamer can comprise any of the following sequences:

T-1
(SEQ ID NO: 49)
GGTGGTGGTGGTTGTGGTGGTGGTGGTTTTCGATGGCCCACTACGTAAA

CCGTC;

T-2
(SEQ ID NO: 50)
GGTGGTGGTGGTTGTGGTGGTGGTGGTTTTCGGTTTGCGTATTGGGAACG

CGCG;

T-11
(SEQ ID NO: 51)
GGTGGTGGTGGTTGTGGTGGTGGTGGTTTTGACAGCATCGGAACGAACCC

TCAG;

T-12
(SEQ ID NO: 52)
GGTGGTGGTGGTTGTGGTGGTGGTGGATTTTACTTTCAACAGTTTCTGGG

ATTT;

T-205
(SEQ ID NO: 53)
GGTGGTGGTGGTTGTGGTGGTGGTGGTTTTACCAGTAATAAAAGGGATTC

ACCA;

T-206
(SEQ ID NO: 54)
GGTGGTGGTGGTTGTGGTGGTGGTGGTTTTAATCAATATCTGGTCACAAA

TATC;

T-215
(SEQ ID NO: 55)
GGTGGTGGTGGTTGTGGTGGTGGTGGTTTTATAAATCCTCATTAAATGAT

ATTC;

or

T-216
(SEQ ID NO: 56)
GGTGGTGGTGGTTGTGGTGGTGGTGGTTTTTATAAGTATAGCCCGGCCGT

CGAG.

In some embodiments, the aptamer is any of the aptamers listed in Tables 1 or 2.

TABLE 1

Aptamer sequences of the present invention.

| Aptamer Name | Target | Sequence (5' to 3') |
|---|---|---|
| Macugen (Pegaptanib Sodium) | vascular endothelial growth factor (VEGF) | CGGAAUCAGUGAAUGCUUAUACAUCCG (SEQ ID NO: 57) As modified: (2'-deoxy-2'-fluoro)C-Gm-Gm-A-A-(2'-deoxy-2'-fluoro)U-(2'-deoxy-2'-fluoro)C-Am-Gm-(2'-deoxy-2'-fluoro)U-Gm-Am-Am-(2'-deoxy-2'-fluoro)U-Gm-(2'-deoxy-2'-fluoro)C-(2'-deoxy-2'-fluoro)U-(2'-deoxy-2'-fluoro)U-Am-(2'-deoxy-2'-fluoro)U-Am-(2'-deoxy-2'-fluoro)C-Am-(2'-deoxy-2'-fluoro)U-(2'-deoxy-2'-fluoro)C-(2'-deoxy-2'-fluoro)C-Gm-(3'→3')-dT), 5'-ester with α,α'-[4,12-dioxo-6-[[[5-(phosphoonoxy)pentyl]amino]carbonyl]-3,13-dioxa-5,11-diaza-1,15-pentadecanediyl]bis [ω-methoxypoly(oxy-1,2-ethanediyl)] (SEQ ID NO: 132) |
| CL4 | EGFR | GCCUUAGUAACGUGCUUUGAUGUCGAUUCGAC AGGAGGC (SEQ ID NO: 58) |
| E07 | EGFR | UGCCGCUAUAAUGCACGGAUUUAAUCGCCGUA GAAAAGCAUGUCAAAGCCG (SEQ ID NO: 59) |
| 3.1 | hTNFα | CCCCGGGUUCUGUAUGAUCCGACCGGUCAGAU AAGACCAC (SEQ ID NO: 60) |
| 7.5 | hTNFα | CGCAUCGUUUGCGUGGCGUGUCCGGGCGCCGA UUCGUAAA (SEQ ID NO: 61) |
| 12 | hTNFα | CUAGGCGGAUUGUUUCGAUUCUUUGCCUUGUC CCUAGUGC (SEQ ID NO: 62) |
| 14.8 | hTNFα | CGUAUAUACGGAUUAGGUUGUAGCUCAGACCA GUAAUGUC (SEQ ID NO: 63) |
| 16.3 | hTNFα | CGUGCUAGAUGCUACGAGUGGUCUCCUCACGU AGAAGGGG (SEQ ID NO: 64) |
| 18.10 | hTNFα | GGUCCCACAUAGGUUGGUCUUGUUGUAUGGGC UGUUUGCA (SEQ ID NO: 65) |

TABLE 1-continued

Aptamer sequences of the present invention.

| Aptamer Name | Target | Sequence (5' to 3') |
|---|---|---|
| 1 | hTNFα | GUGUUUUGGGAGAGAAAAGGGGGAGCCUUUACUUUGUUGG (SEQ ID NO: 66) |
| 2 | hTNFα | GACGAUGUUAUCAGGGAGUUGGGAUCAUAUAGUCUUACAU (SEQ ID NO: 67) |
| 4 | hTNFα | CGCAAGAGCCGCCCUAAUGGUUCAAUGGUAACUGUAUAUG (SEQ ID NO: 68) |
| 6 | hTNFα | GACUUCUUGUGCCAUUAUGAAUUAUUGCUAAUCCUCUUGA (SEQ ID NO: 69) |
| 8.6 | hTNFα | AGGACGUACUUGGAAAAGAGGCGCGAAGAACCUGGUAUGU (SEQ ID NO: 70) |
| 9 | hTNFα | UAGGACGUACUUGGAAAAGAGGCGCGAAGAACCUGGUAUG (SEQ ID NO: 71) |
| 10 | hTNFα | UGGCCACCUUGCCACUCUUCCUUGCAUAUUUUACUCCCGC (SEQ ID NO: 72) |
| 11.7 | hTNFα | CAAGCCGAGGGGGAGUAUCUGAUGACAAUUCGGAGCUCCA (SEQ ID NO: 73) |
| 13.2 | hTNFα | UCAUGGUGUGUGAGUUAGCUCACGUGCCGUUUCGAAGGCG (SEQ ID NO: 74) |
| 17.9 | hTNFα | CAUGGGCUAGACCGGCAUAAAACUGCUGUAGUUGCACGCC (SEQ ID NO: 75) |
| 19 | hTNFα | UGGCCACCUUGCCACUCUUCCUUGCAUAUUUUACUCCCGC (SEQ ID NO: 76) |
| 20.4 | hTNFα | CGUUGUAGUAGUGGCUUGGGCAUAACUCAGUUAAACACUA (SEQ ID NO: 77) |
| 5 | hTNFα | GACCGCGGAAAAGGAAGGAAUUAGAUACAACGGAGAAGUG (SEQ ID NO: 78) |
| 15 | hTNFα | GACCGCGGAAAAGGAAGGAAUUAGAUACAACGGAGAAGUG (SEQ ID NO: 79) |
| T1.7.5 | hTNFα | CGCAUCGUUUGCGUGGCGUGUCCGGGCGCCGAUUCGUAAA (SEQ ID NO: 80) |
| T2.13.2 | hTNFα | UCAUGGUGUGUGAGUUAGCUCACGUGCCGUUUCGAAGGCG (SEQ ID NO: 81) |
| T3.11.7 | hTNFα | CAAGCCGAGGGGGAGUAUCUGAUGACAAUUCGGAGCUCCA (SEQ ID NO: 82) |
| T4.14.8 | hTNFα | CGUAUAUACGGAUUAGGUUGUAGCUCAGACCAGUAAUGUC (SEQ ID NO: 83) |
| A38 | Vaccinia virus | TACGACTCACTATAGGGATCCTGTATATATTTTGCAACTAATTGAATTCCCTTTAGTGAGGGTT (SEQ ID NO: 84) |
| Alicaforsen (ISIS 2302) | ICAM-1 | GCCCAAGCTGGCATCCGTCA (SEQ ID NO: 85) |
| AX102 (RNA) | PDGF-B | 5'-dC-dC-dC-dA-dG-dG-dC-T-dA-dC-mG-HEG-dC-dG-T-dA-mG-dA-mG-dC-dA-mU-mC-mA-HEG-T-dG-dA-T-mC-dC-T-mG-mG-mG-3'dT (SEQ ID NOS 86, 130, and 131, respectively) |
| SL(2)-B (DNA) | VEGF | CAATTGGGCCCGTCCGTATGGTGGGT (SEQ ID NO: 87) |
| RNV66 (DNA) | VEGF | TGTGLGGGTGGACGGGCCGGLTALA (L = LNA guanine) (SEQ ID NO: 88) |
| AS1411 | Nucleolin | GGTGGTGGTGGTTGTGGTGGTGGTGG (SEQ ID NO: 89) |

TABLE 1-continued

Aptamer sequences of the present invention.

| Aptamer Name | Target | Sequence (5' to 3') |
|---|---|---|
| FCL-II 6L/12D/24$_{dI}$ | Nucleolin | ggt ggTL ggt ggTD tgt ggt ggt ggdI gg (SEQ ID NO: 90) (2'-deoxyinosine (2'-dI) and D-/L-isothymidine (D-/L-isoT)) |
| PNDA-3 (DNA) | Periostin | ACGAGYYGYCGCAYGYGCGGYYCAGYCYGGYC CYYCAGCACCGYACAACAA (SEQ ID NO: 91) |
| NAS-24 (DNA) | Vimentin | CTC CTC TGA CTG TAA CCA CGC CTG GGA CAG CCA CAC AGA AGT GTA GAC CTC GCG GAA TCG GCA TAG GTA GTC CAG AAG CC (SEQ ID NO: 92) |
| YJ-1 (RNA) | CEA | GCGGAAGCGUGCUGGGCUAGAAUAAUAAUAA GAAAACCAGUACUUUCGU (SEQ ID NO: 93) |
| AGE-apt (DNA) | AGE | CGAAACCAGACCACCCCACCAAGGCCACTCGG TCGAACCGCCAACACTCACCCCA (SEQ ID NO: 94) |
| A-P50 (RNA) | NF-κB | GATCTTGAAACTGTTTTAAGGTTGGCCGATC (SEQ ID NO: 95) |
| OPN-R3 (RNA) | OPN | CGGCCACAGAAUGAAAAACCUCAUCGAUGUUG CAUAGUUG (SEQ ID NO: 96) |
| cy-apt (DNA) | HGC-27 | CGACCCGGCACAAACCCAGAACCATATACACG ATCATTAGTCTCCTGGGCCG (SEQ ID NO: 97) |
| A9g (RNA) | PSMA | GGGACCGAAAAAGACCTGACTTCTATACTAAGT CTACGTTCCC (SEQ ID NO: 98) |
| ESTA (DNA) | E-selectin | CGCTCGGATCGATAAGCTTCGATCCCACTCTCC CGTTCACTTCTCCTCACGTCACGGATCCTCTAGA GCACTG (SEQ ID NO: 99) |
| M12-23 (RNA) | 4-1 BB | GGGAGAGAGGAAGAGGGAUGGGCGACCGAAC GUGCCCUUCAAAGCCGUUCACUAACCAGUGGC AUAACCCAGAGGUCGAUAGUACUGGAUCCCCC C (SEQ ID NO: 100) |
| OX40-apt (RNA) | OX40 | CAGUCUGCAUCGUAGGAAUCGCCACCGUAUAC UUUCCCAC (SEQ ID NO: 101) |
| CD28-apt (RNA) | CD28 | CAGAGACTTCCAAAATAAAAGACTC (SEQ ID NO: 102); CTGAAAGTTGCAAAATAAAAAACTC (SEQ ID NO: 103); CACTTACCACAATAACAAACGGGTG (SEQ ID NO: 104); CCTGCACCACAGGGAGACGGGGGCC (SEQ ID NO: 105); GATTAGACCATAGGCTCCCAACCCC (SEQ ID NO: 106); TCTGAGGTGCTCCTGCTTTGGAACT (SEQ ID NO: 107); and CAAGACCGTTATGTCGTGTGTACTT (SEQ ID NO: 108) |
| De160 (RNA) | CTLA-4 | CCGACGTGCCGCAACTTCAACCCTGCACAACCA ATCCGCC (SEQ ID NO: 109) |
| PSMA-4-1 BB-apt (RNA) | PSMA/4-1 BB | GGGAGGACGAUGCGGAUCAGCCAUGUUUACGU CACUCCUUGUCAAUCCUCAUCGGCAGACGACU CGCCCGA (SEQ ID NO: 110) |
| MP7 (DNA) | PD-1 | GTACAGTTCCCGTCCCTGCACTACA (SEQ ID NO: 111); GTACAGTTCCCGTCCTGCACTACA (SEQ ID NO: 112) |
| aptPD-L1 (DNA) | PD-L1 | ACGGGCCACATCAACTCATTGATAGACAATGCG TCCACTGCCCGT (SEQ ID NO: 113) |
| R5A1 (RNA) | IL10R | CTGTAATTGGCGTATGTAACCCAGGCACCAAAC ACCCCAG (SEQ ID NO: 114) |
| CL-42 (RNA) | IL4Rα | AAAAAGCAACAGGGTGCTCCATGCGCATCGAA CCTGCGCG (SEQ ID NO: 115) |
| CD44-EpCAM aptamer (RNA) | CD44/ EpCAM | GGGATGGATCCAAGCTTACTGGCATCTGGATTT GCGCGTGCCAGAATAAAGAGTATAACGTGTGA ATGGGAAGCTTCGATAGGAATTCGG (SEQ ID NO: 116); GCGACTGGTTACCCGGTCTAA (SEQ ID NO: 117) |

TABLE 1-continued

Aptamer sequences of the present invention.

| Aptamer Name | Target | Sequence (5' to 3') |
|---|---|---|
| TIM3Apt (RNA) | TIM3 | GGGAGAGGACCAUGUAGUCACUAUGGUCUUG GAGCUAGCGGCAGAGCGUCGCGGUCCCUCCC GGGAGAGGACCAUGUACUGGUAGUUCUCUGU GCGACUCCUACAGAGAGUCGCGGUCCCUCCC GGGAGAGGACCAUGUACUGGGUUGUAGGGGG GCUCCUUAGGCAGAGCGUCGCGGUCCCUCCC GGGAGAGGACCAUGUACCCCGCAAUGCGGCCC CAGACUUCAACAGAGCGUCGGGUCCCUCCC GGGAGAGGACCAUGUACCGCAUGUGCGCGAGA GGUAGCGACAGAGCGUCGCGGUCCCUCCC (SEQ ID NO: 118) |
| AptCTLA-4 (DNA) | CTLA-4 | TCCCTACGGCGCTAACGATGGTGAAAATGGGCC TAGGGTGGACGGTGCCACCGTGCTACAAC (SEQ ID NO: 119) |

TABLE 2

Aptamer names and targets of the present invention.

| Aptamer Name | Target |
|---|---|
| ARC126 (RNA) | PDGF-B |
| NOX-A12 (RNA) | CXCL12 |
| E0727 (RNA) | EGFR |
| CL428 (RNA) | EGFR |
| KDI130 (RNA) | EGFR |
| TuTu2231 (RNA) | EGFR |
| TTA140,41 (DNA) | Tenascin-C |
| GBI-1042 (DNA) | Tenascin-C |
| GL21.T (RNA) | Axl |
| AGC03 (DNA) | HGC-27 |
| BC15 (DNA) | hnRNP A1 |
| CD16α/c-Met-apt (RNA) | CD16α/c-Met |
| VEGF-4-1BB apt (DNA) | VEGF/4-1BB |

In some embodiments, this invention provides for a RNA nanostructure robot, wherein the targeting strand comprises a domain comprising a polynucleotide sequence for attaching to $NR_1$ or $NR_2$.

In some embodiments, this invention provides for a RNA nanostructure robot, wherein the first or second scaffold is configured to have a rectangular sheet having four corners and is shaped into a tube-shape. In some embodiments, the dimension of the rectangular sheet is about 90 nm×about 60 nm×about 2 nm. In some embodiments, one or more targeting strands are positioned at one or more corners of the rectangular sheet. In some embodiments, the tube-shaped origami structure has a diameter of about 19 nm.

In some embodiments, one or more of $R_3$ and/or $R_4$ is a capture strand. As used herein, the term "capture strand" is a polynucleic acid which is in part complementary to a homopolynucleic acid sequence. In some embodiments, the capture strand can bind to a poly(A) region in $NR_1$ or $NR_2$. In some embodiments, the capture strands is operably linked to a therapeutic agent. The capture strand can comprise a modified nucleoside or ribonucleoside which can bind to the therapeutic agent. In some embodiments, the capture strand comprises an RNA loop. In some embodiments, the capture strand comprises poly(U). In some embodiments, the capture stand comprises a sequence comprising an amino-modified ribonucleoside.

In some embodiments, one or more of $R_3$ and/or $R_4$ is a therapeutic agent which is operably linked to the RNA nanostructure.

In some embodiments, the RNA nanostructure comprises one single-stranded RNA (ssRNA) molecule which forms at least one paranemic cohesion crossover.

In some embodiments, the RNA nanostructure is immuno-stimulatory.

In some embodiments, the RNA nanostructure comprises a nucleic acid sequence having at least about 90% sequence identity to SEQ ID NO:1 or SEQ ID NO: 9. In some embodiments, the RNA nanostructure comprises a nucleic acid sequence having at least about 95% sequence identity to SEQ ID NO:1 or SEQ ID NO: 9. In some embodiments, the RNA nanostructure comprises SEQ ID NO:1 or SEQ ID NO: 9. In some embodiments, the RNA nanostructure consists of SEQ ID NO: 1 or SEQ ID NO: 9.

In some embodiments, one or more of $R_3$ and/or $R_4$ is a peptide that comprises a positively-charged moiety which comprises from about 10 positively-charged amino acids. The the positively-charged moiety is a peptide comprising 10 lysine residues.

In some embodiments, one or more of $R_3$ and/or $R_4$ is a protein, wherein the protein is selected from: tumor targeting peptide (TTP), a human cancer peptide, or calreticulin protein. In some embodiments, the protein is calreticulin protein to RNA-origami to engage interactions between tumor cells and macrophages or dendritic cells for enhanced antigen presentation and stimulation of antigen-specific T cells. In some embodiments, the protein is Human cancer peptide NY-ESO-1 or Mucd. In some embodiments, the TTP is CTKD-K10 having the sequence: CTKDNNLLGR-FELSGGGSKKKKKKKKKK (SEQ ID NO: 3).

In some embodiments, this invention provides for a pharmaceutical composition comprising a RNA nanostructure robot described herein and a pharmaceutically acceptable carrier. In some embodiments, the pharmaceutical composition further comprises at least one therapeutic agent.

In some embodiments, this invention provides for a method of treating cancer in a subject, comprising administering to the subject a therapeutically effective amount of the composition described herein. In some embodiments, the cancer is breast cancer, ovarian cancer, melanoma or lung cancer.

In some embodiments, this invention provides for a method of inhibiting tumor growth in a subject, comprising administering to the subject a therapeutically effective amount of a composition described herein.

In some embodiments, this invention provides for the use of the RNA nanostructure robot as described herein or a composition as described herein for the manufacture of a medicament for inducing a tumor necrosis response in a subject.

In some embodiments, this invention provides for the use of the RNA nanostructure robot as described as described herein or a composition as described herein for inducing a tumor necrosis response.

In some embodiments, this invention provides for the use of the RNA nanostructure robot as described as described herein or a composition as described herein for the manufacture of a medicament for treating a disease or disorder in a subject.

In some embodiments, this invention provides for the use of the RNA nanostructure robot as described as described herein or a composition as described herein for the prophylactic or therapeutic treatment a disease or disorder.

In certain embodiments, the present invention provides a complex comprising an RNA nanostructure and at least one diagnostic and/or therapeutic agent operably linked to the RNA nanostructure.

In certain embodiments, the RNA nanostructure comprises one single-stranded RNA (ssRNA) molecule, wherein the ssRNA molecule forms at least one paranemic cohesion crossover, and wherein the RNA nanostructure has immunostimulatory properties.

In certain embodiments, the RNA nanostructure comprises one single-stranded RNA (ssRNA) molecule, wherein the ssRNA molecule comprises a plurality of regions of double helices, wherein at least two of the plurality of regions of double helices form a paranemic cohesion crossover, and wherein the RNA nanostructure has immunostimulatory properties.

In certain embodiments, the e ssRNA molecule comprises at least two parallel double helices.

In certain embodiments, about 60-99% of the RNA nanostructure is double stranded and about 1-40% of the RNA nanostructure is single stranded.

In certain embodiments, about 95% of the RNA nanostructure is double stranded and about 5% of the RNA nanostructure is single stranded.

In certain embodiments, the RNA nanostructure comprises rectangular origami nanostructure.

In certain embodiments, the RNA nanostructure comprises a nucleic acid sequence about 1500 to about 2500 nucleotides in length.

In certain embodiments, the RNA nanostructure comprises a nucleic acid sequence having at least about 75% sequence identity to SEQ ID NO:1 or SEQ ID NO: 9.

In certain embodiments, the RNA nanostructure comprises a nucleic acid sequence having at least about 85% sequence identity to SEQ ID NO:1 or SEQ ID NO: 9.

In certain embodiments, the RNA nanostructure comprises a nucleic acid sequence having at least about 95% sequence identity to SEQ ID NO:1 or SEQ ID NO: 9. In certain embodiments, the RNA nanostructure comprises a nucleic acid sequence having at least about 90% sequence identity to SEQ ID NO:1 or SEQ ID NO: 9.

In certain embodiments, the RNA nanostructure comprises SEQ ID NO:1 or SEQ ID NO: 9.

In certain embodiments, the RNA nanostructure consists of SEQ ID NO:1 or SEQ ID NO: 9.

In certain embodiments, the nucleic acid sequence of the RNA nanostructure is about 1500 to about 2500 nucleotides in length.

In certain embodiments, the RNA nanostructure comprises at least one paranemic cohesion crossover.

In certain embodiments, the diagnostic or therapeutic agent is a peptide comprises a positively-charged moiety.

In certain embodiments, the positively-charged moiety is a peptide comprising from about 5 to 20 positively-charged amino acids.

In certain embodiments, the positively-charged moiety is a peptide comprising from about 8 to 12 positively-charged amino acids.

In certain embodiments, the positively-charged moiety is a peptide comprising from about 10 positively-charged amino acids.

In certain embodiments, the positively-charged moiety is a peptide comprising 10 lysine residues.

In certain embodiments, the protein is tumor targeting peptide (TTP), a human cancer peptide, an infectious agent peptide, or calreticulin protein.

In certain embodiments, the infectious agent peptide is specific epitopes for CD8+ T cells involved in the immunity against influenza, HIV, HCV, and other infectious agents.

In certain embodiments, the protein is calreticulin protein. Calreticulin protein allows the RNA-origami to engage interactions between tumor cells and macrophages or dendritic cells for enhanced antigen presentation and stimulation of antigen-specific T cells.

In certain embodiments, the protein is Human cancer peptide NY-ESO-1 or Muc.

In certain embodiments, the present invention provides a pharmaceutical composition comprising the complex described herein and a pharmaceutically acceptable carrier.

In certain embodiments, the present invention provides the pharmaceutical composition described herein and further comprising at least one therapeutic agent.

In certain embodiments, the at least one therapeutic agent is a chemotherapeutic drug.

In certain embodiments, the chemotherapeutic drug is doxorubicin.

In certain embodiments, the present invention provides a method of inducing an immune response a subject (e.g., a mammal, such as a human), comprising administering to the subject an effective amount of a complex or a composition as described herein.

In certain embodiments, the present invention provides a method of treating a disease or disorder in a subject, comprising administering to the subject a therapeutically effective amount of a complex or a composition as described herein.

In certain embodiments, the disease or disorder is cancer.

In certain embodiments, the cancer is breast cancer.

In certain embodiments, the cancer is colon cancer.

In certain embodiments, the method further comprises administering at least one therapeutic agent to the subject.

In certain embodiments, the at least one therapeutic agent is a tumor targeting agent.

In certain embodiments, the tumor targeting agent is a monoclonal tumor specific antibody or an aptamer.

In certain embodiments, the present invention provides a method of enhancing/increasing pro-inflammatory cytokines in a subject (e.g., a mammal, such as a human), comprising administering to the subject an effective amount of a complex or a composition as described herein.

In certain embodiments, the present invention provides a method of activating immune cells by specific triggering of TLR3 signaling pathway in a subject (e.g., a mammal, such as a human), comprising administering to the subject an effective amount of a complex or a composition as described herein.

In certain embodiments, the present invention provides a method of slowing or suppressing tumor growth in a subject (e.g., a mammal, such as a human) as compared to a control subject, comprising administering to the subject an effective amount of a complex or a composition as described herein.

In certain embodiments, the present invention provides a method to elevate levels of anti-tumor proinflammatory cytokines in a subject (e.g., a mammal, such as a human) with a tumor as compared to a control subject, comprising administering to the subject an effective amount of a complex or a composition as described herein.

In certain embodiments, the present invention provides a method to decrease levels of anti-inflammatory cytokines in a subject (e.g., a mammal, such as a human) with a tumor as compared to a control subject, comprising administering to the subject an effective amount of a complex or a composition as described herein.

In certain embodiments, the present invention provides the use of a complex or a composition as described herein for the manufacture of a medicament for inducing an immune response in a subject (e.g., a mammal, such as a human).

In certain embodiments, the present invention provides a complex or a composition as described herein for inducing an immune response.

In certain embodiments, the present invention provides a use of a complex or a composition as described herein for the manufacture of a medicament for treating a disease or disorder in a subject.

In certain embodiments, the present invention provides a complex or a composition as described herein for the prophylactic or therapeutic treatment of a disease or disorder.

In certain embodiments, the present invention provides a kit comprising a complex or a composition as described herein and instructions for administering the RNA anostructure/composition to a subject to induce an immune response or to treat a disease or disorder. In certain embodiments, the kit further comprises at least one therapeutic agent. The kits of the invention can include any combination of the compositions and/or vaccines disclosed above and suitable instructions (e.g., written, audiovisual). In one embodiment, the kit includes a pharmaceutical composition or vaccine that is packaged along with instructions for use and any instrument useful in administering the compositions. For example, the kits of the invention can include one or more of: diluents, gloves, vials or other containers, pipettes, needles, syringes, tubing, sterile cloths or drapes, positive and/or negative controls, and the like.

Figure 20:
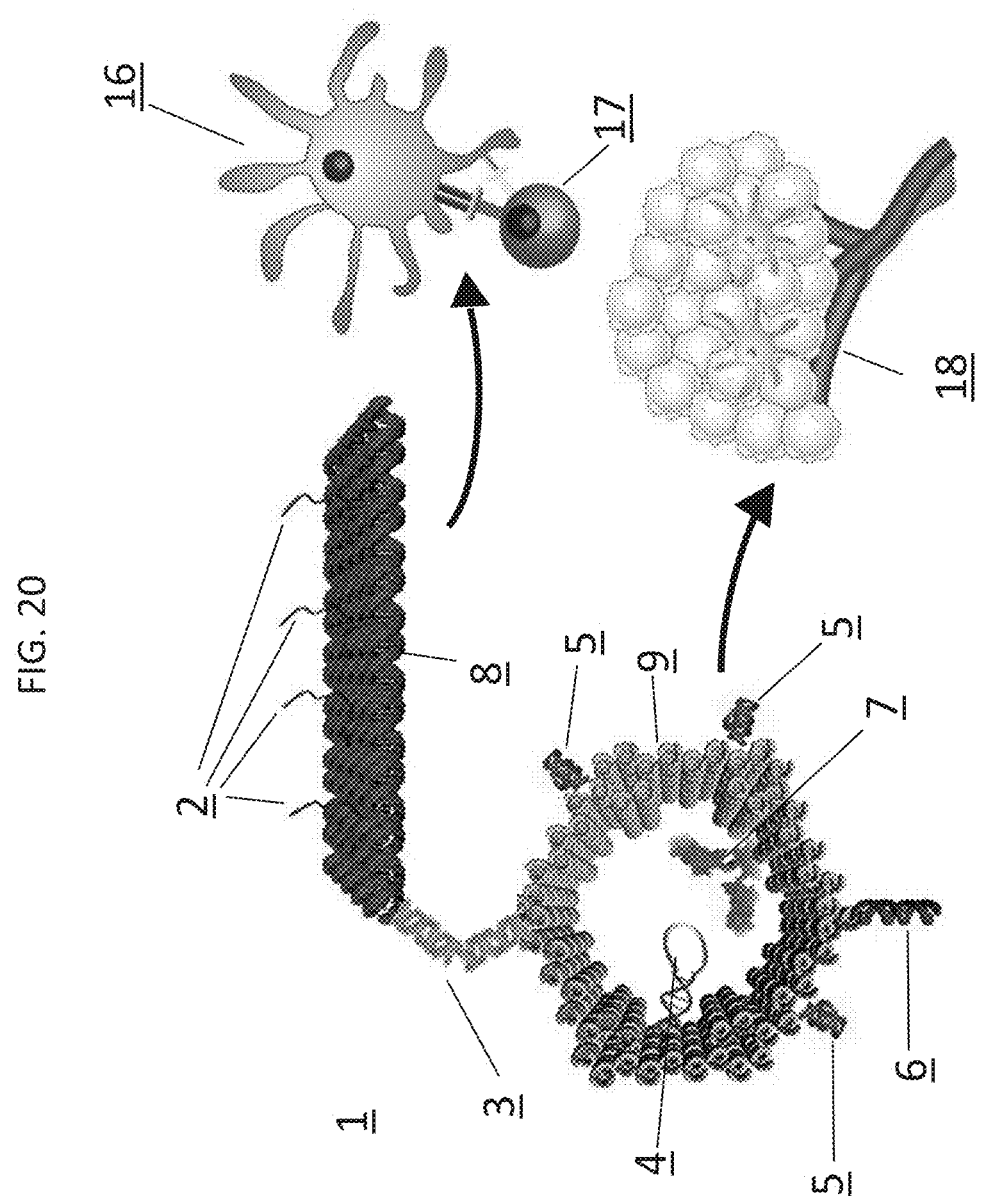
FIG. 20. Exemplary RNA nanostructure double-robot. In some embodiments, RNA-origami comprises antigen-specific peptides, which are linked via a pH-sensitive double helix to an RNA-nanocage that is responsive to interferon-gamma to release checkpoint inhibitor antagonists.

As shown in FIG. 20, in some embodiments the RNA nanostructure polymeric robot 1 comprises a first nano-robot ($NR_1$) 8, a second nano-robot ($NR_2$) 9, a linker (L) 3, a moiety ($R_3$) 2 and n is 1 or more, and the moiety $R_3$ is in contact with $NR_1$. In some embodiments, the moiety $R_3$ is an antigen peptide. A second optionally heterogeneous series of moiety $R_4$ (4, 5, 6, 7) comprise a nucleolin-binding or other cancer tumor marker aptamers 5 wherein m is 2 or more, an aptamer-target bound lock 6, optionally a cargo molecule 7, and optionally a checkpoint antagonist 4. In some embodiments, the linker (L) 3 comprises of a double-stranded oligonucleotide helix. In some embodiments, the antigen peptides are tumor antigen peptides. In some embodiments, the tumor antigen peptides are TTP. In some embodiments, the cargo molecule 7 is a therapeutic agent. In some embodiments, the cargo molecule 7 is an antibody. The antibody can be an anti-PD-1 antibody. The antibody can further comprise a linkage to a polylysine chain. In some embodiments, the checkpoint antagonist is an anti-PD-1 aptamer. In some embodiments, the checkpoint antagonist is an anti-PD-1 antibody. In some embodiments, the first nano-robot ($NR_1$) 8 is an immune-adjuvant RNA robot exhibiting immune-stimulatory properties. In some embodiments, the aptamer-target bound lock 6 is an INF-γ aptamer bound to INF-γ. In some embodiments, the second nano-robot ($NR_2$) 9 is configured to be in a cylindrical conformation which is operably openable via the aptamer-target bound lock 6. The RNA nanostructure polymeric robot 1 induces activation of T cells 11 at antigen-presenting cells 9 by contacting the first nano-robot ($NR_1$) 8 comprising a moiety $R_3$ wherein the moiety is an antigen peptide 2, with a T cell 11. In some embodiments, the second nano-robot ($NR_2$) 9 interacts with the tumor environment 13. In some embodiments, the aptamer-target bound lock 6 is opened when the target is a compound, biomarkers, or protein present in high regional concentration in the tumor environment 13. The aptamer-target bound lock 6 competitively binds with the free target in the tumor environment 13, resulting in the unlocking of the second nano-robot ($NR_2$) 9. The opening of the second nano-robot ($NR_2$) 9 exposes the optional cargo molecule 7, and the optional checkpoint antagonist 4, to the tumor environment. When the cargo molecule 7 is a therapeutic agent and/or the checkpoint antagonist 4 is present, the therapeutic agent and/or checkpoint antagonist effect tumor necrosis in the tumor environment 13.

Figure 21:
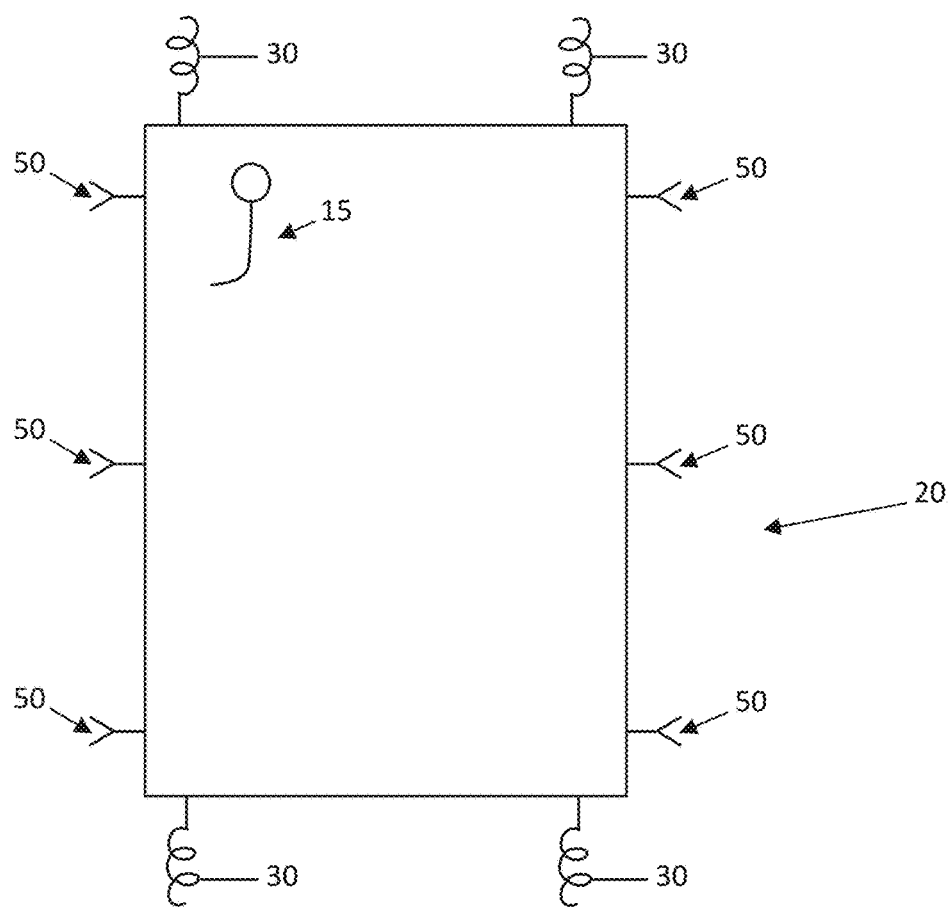
FIG. 21 depicts an unfastened rectangular RNA origami structure having fasteners extending from the edges that can be joined, aptamer-containing targeting strands and antigen-specific peptides (to induce tumor-specific immunity), as well as pH-sensitive linker to allow dissociation of RNA-origami from the RNA nanocages in tumor microenvironment.

As shown in FIG. 21, in certain embodiments the scaffold is an unfolded rectangular RNA origami structure 20 having fasteners 50 extending from the edges that is joined, aptamer-containing targeting strands and a therapeutic agent-RNA conjugate capture strand. In certain embodiments, the RNA origami structure 20 also has aptamer-containing targeting strands 30 attached thereto.

Figure 22:
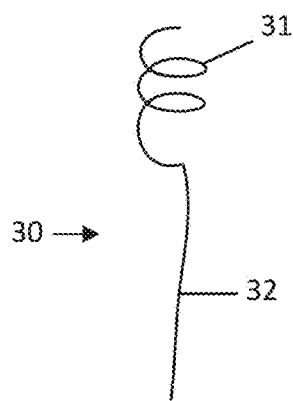
FIG. 22 depicts an aptamer-containing targeting strand containing an aptamer portion and an attaching RNA strand.

As shown in FIG. 22 in certain embodiments the aptamer-containing targeting strand 30 containing an aptamer portion 31 and an attaching RNA strand portion 32.

Figure 23:
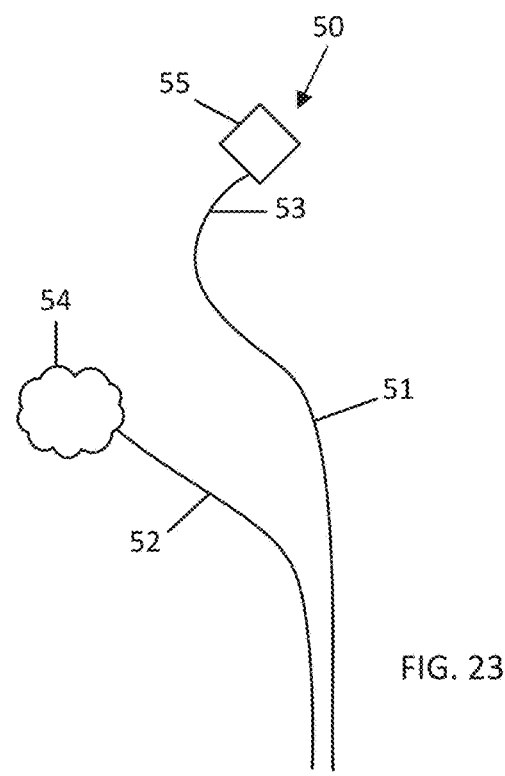
FIG. 23 depicts an aptamer-containing targeting strand containing an aptamer portion and an attaching RNA strand, and having a quencher moiety attached to one arm of the Y-structure and a fluorophore moiety attached to the second arm of the Y-structure.

As shown in FIG. 23 in certain embodiments the fastener 50 has two arms 51 and 52, and having a quencher moiety 54 attached to one arm 52 of the Y-structure and a fluorophore moiety 55 attached to the second arm 51 of the Y-structure by means of a linker 53.

As shown in FIG. 24 in certain embodiments the therapeutic agent-RNA conjugate capture strand 15 has a ssRNA attachment strand 10 and a therapeutic agent payload 11. As shown in FIG. 25 in certain embodiments the therapeutic agent payload 11 is operably linked to an imaging agent 12. As shown in FIG. 26 in certain embodiments the ssRNA attachment strand 10 is linked to a therapeutic agent payload 11 by means of a linker 14. As shown in FIG. 27 in certain embodiments therapeutic agent-RNA conjugate capture strand having a ssRNA attachment strand that is linked to a therapeutic agent payload by means of a linker, where the therapeutic agent payload is operably linked to an imaging agent 12.

As shown in FIGS. 28-31, in certain embodiments the unfolded rectangular RNA origami structure has one to four therapeutic agent-RNA conjugates operably linked to the origami structure. The therapeutic agent-RNA conjugates can be attached to either the "top" or the "bottom" (or both) of the origami structure, such that when the origami structure is rolled into a tube, the therapeutic agent-RNA conjugates can be designed to be either on the inside or outside of the tube.

Figure 32:
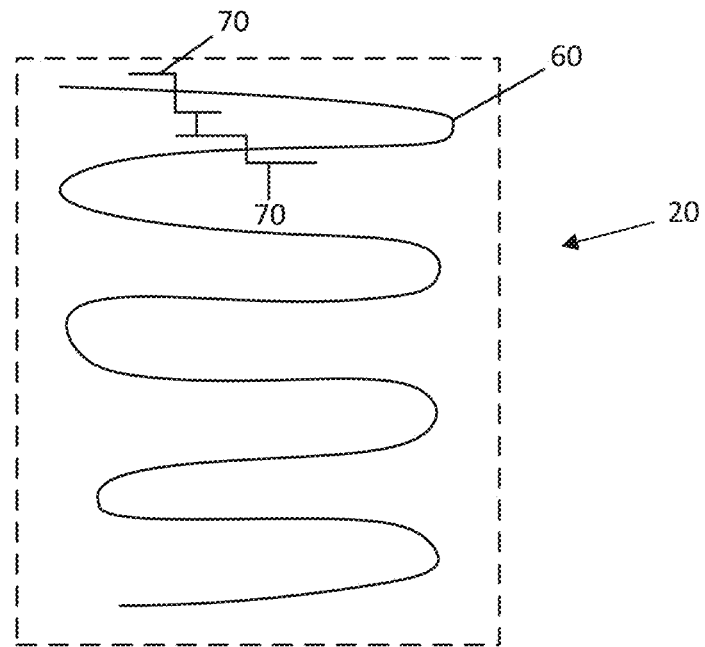
FIG. 32 depicts an exploded view of the RNA origami structure, detailing the hybridization of a single stranded RNA scaffold strand and staple strands, and the interaction of the two staple strands.

FIG. 32 depicts an exploded view of the RNA origami structure 20, detailing the hybridization of a single stranded RNA scaffold strand 60 and staple strands 70, and the interaction of the two staple strands.

Figure 33:
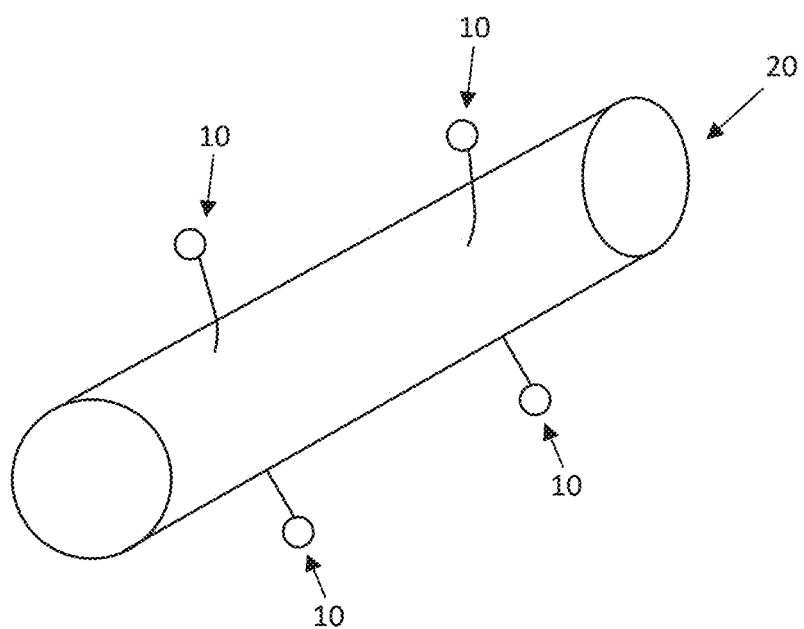
FIG. 33 depicts a tube-shaped RNA origami structure having drug-RNA conjugates positioned on the outside of the tube-shaped RNA origami structure.

As shown in FIG. 33 in certain embodiments, the tube-shaped RNA origami structure have therapeutic agent-RNA conjugates 10 positioned on the outside of the tube-shaped RNA origami structure.

Figure 34:
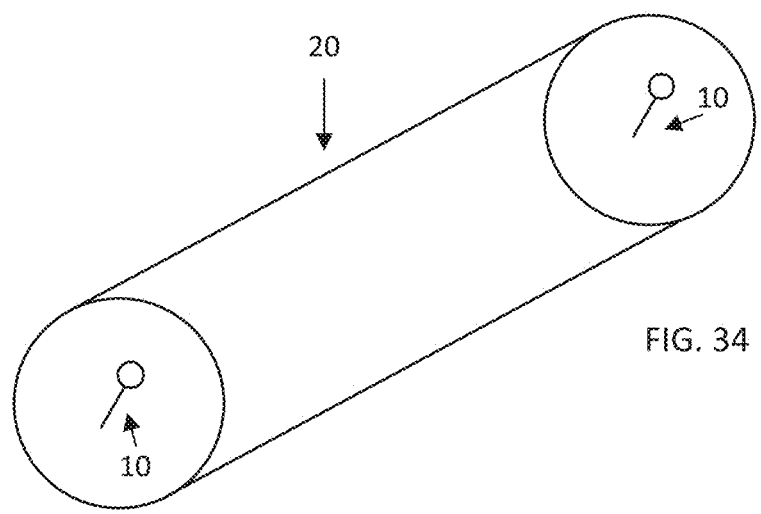
FIG. 34 depicts a tube-shaped RNA origami structure having drug-RNA conjugates positioned on the inside of the tube-shaped RNA origami structure.

As shown in FIG. 34 in certain embodiments, the tube-shaped RNA origami structure having therapeutic agent-RNA conjugates 10 positioned on the inside of the tube-shaped RNA origami structure.

Figure 35:
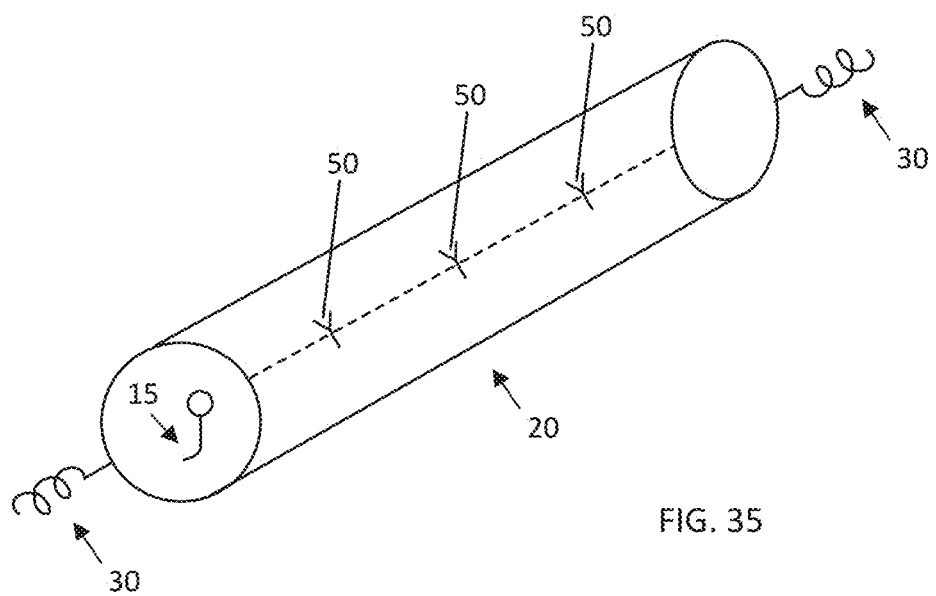
FIG. 35 depicts a tube-shaped RNA origami structure having drug-RNA conjugates positioned on the inside of the tube-shaped RNA origami structure, having aptamer-containing targeting strands positioned at the ends of the tube, and illustrating the fasteners joining the edges of the RNA origami structure so as to form a tube shape.

As shown in FIG. 35, a tube-shaped RNA origami structure 20 having therapeutic agent-RNA conjugates 15 is positioned on the inside of the tube-shaped RNA origami structure, having aptamer-containing targeting strands 30 positioned at the ends of the tube, and illustrating the fasteners 50 joining the edges of the RNA origami structure so as to form a tube shape.

Figure 36:
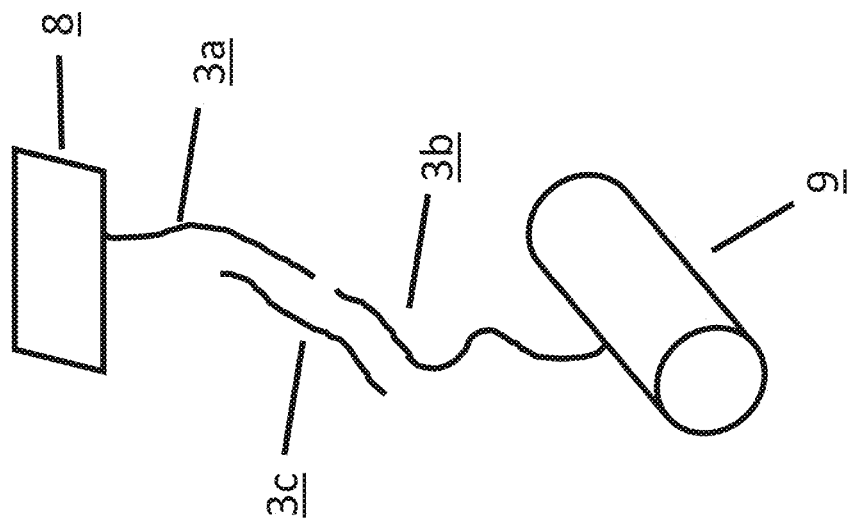
FIG. 36 depicts a schematic for an RNA nanostructure double robot where $NR_1$ and $NR_2$ are separate ssRNA scaffolds linked through a linker either directly via direct partial hybridization or indirectly through a bridging oligonucleotide.
Figure 36:
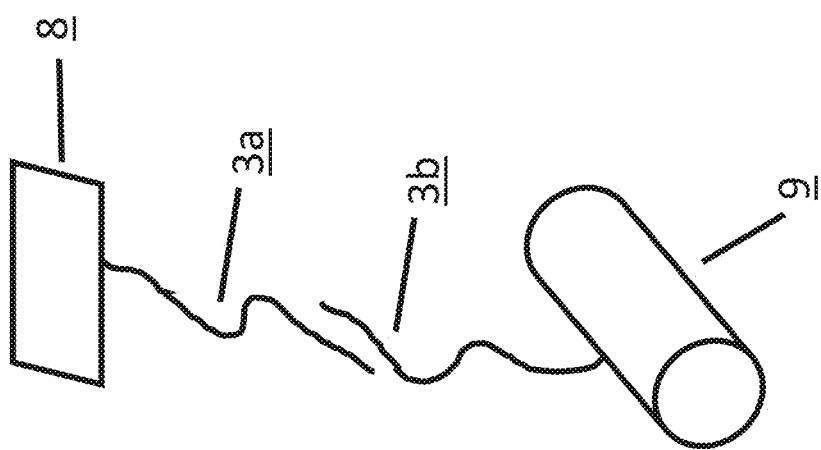

As shown in FIG. 36, a first nano-robot 8 further comprises a single-stranded RNA sequence which forms part of the linker 3a. A second nano-robot 9 further comprises a single-stranded RNA sequence which forms part of the linker 3b. The sequence of linker 3a is complementary, in whole or in part, with the sequence of linker 3b such that hybridization forms linking the first nano-robot 8 to the second nano-robot 9. In some embodiments, the sequence of linker 3a is not complementary to the sequence of linker 3b. In some embodiments, the linker further comprises a bridging oligonucleotide 3c, wherein one terminus of the the sequence of the bridging oligonucleotide 3c is complementary to the sequence of linker 3a, and the other terminus of the sequence of the bridging oligonucleotide 3c is complementary to the sequence of linker 3b. The oligonucleotides can comprise DNA, RNA, or combinations thereof. In some embodiments, the oligonucleotides are pH-sensitive such that hybridization and/or the oligonucleotide sequence denatures at the low pH of the tumor environment. In some embodiments, the sequence of the briding oligonucleotide 3c is complementary to the DNA sequence within the tumor. In some embodiments, the sequence of the briding oligonucleotide 3c is complementary to the RNA sequence overexpressed within the tumor environment.

EXAMPLES

The invention will now be illustrated by the following non-limiting Examples.

Example 1

Figure 2:
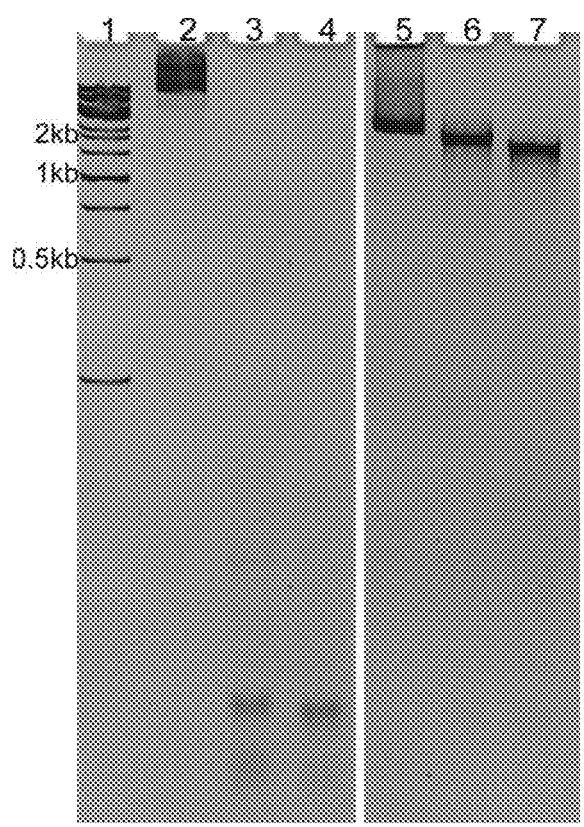
FIG. 2. Nuclease resistance. Self-assembled RNA origami is resistant to RNase I digestion, while the unassembled RNA molecule can be digested easily by RNase I. Lane 1 represents 1 kb dsDNA marker. 1 ug of unassembled RNA molecule was treated without RNase I (lane 2) or with 1 U of RNase I for 10 min or 30 min (lane 3 and 4) at room temperature. The self-assembled RNA origami was also treated without RNase I (lane 5) or with 1 U RNase I for 10 min or 30 min (lane 6 and 7) at room temperature. The results show that for the unassembled (not nanostructured) RNA molecule, the complex is digested by RNase I. The self-assembled (nanostructured) RNA origami, however, did not significantly change in mobility after RNAse I exposure, indicating that the nanostructured RNA origami is more stable than the unassembled sequence.
Figure 3A:
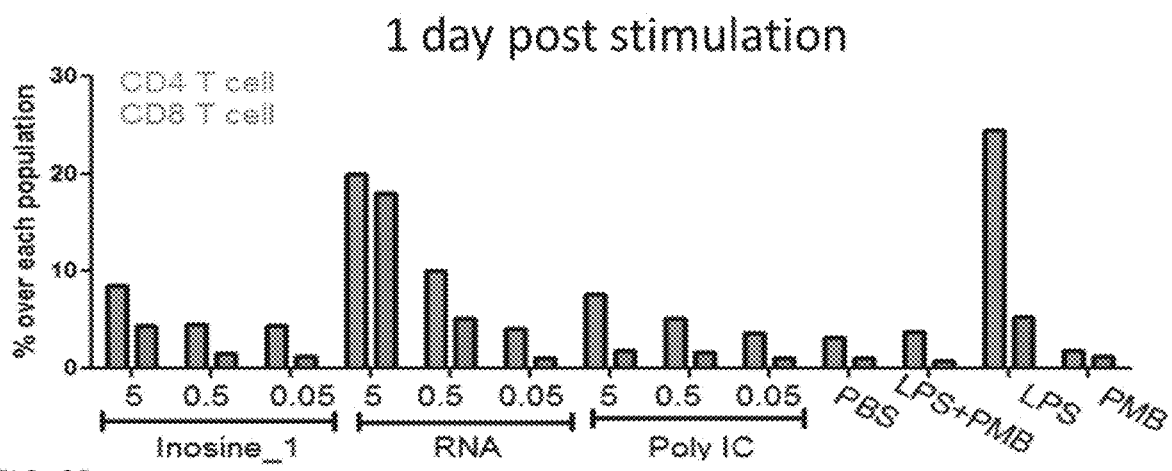
FIG. 3A shows the ex vivo splenocyte stimulation at 1 day post stimulation.
Figure 3B:
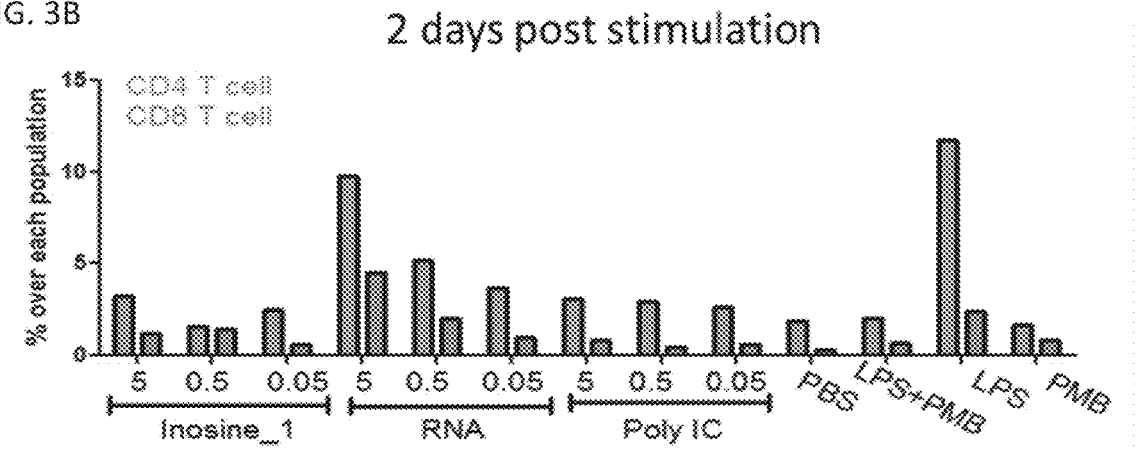
FIG. 3B shows the ex vivo splenocyte stimulation at 2 days post stimulation. CD69 activation in T cell. RNA origami activate both CD8 and CD4 T cells. Percentages of CD69+ cells in CD4 T cells and CD8 T cells are plotted. PBS: phosphate buffer saline, LPS: lipopolysaccharide; PMB: polymyxin B; Inosine_1: inosine-incorporated RNA origami. For each grouping, CD4 T cell is shown in the left and CD8 T cell is shown on the right.
Figure 4A:
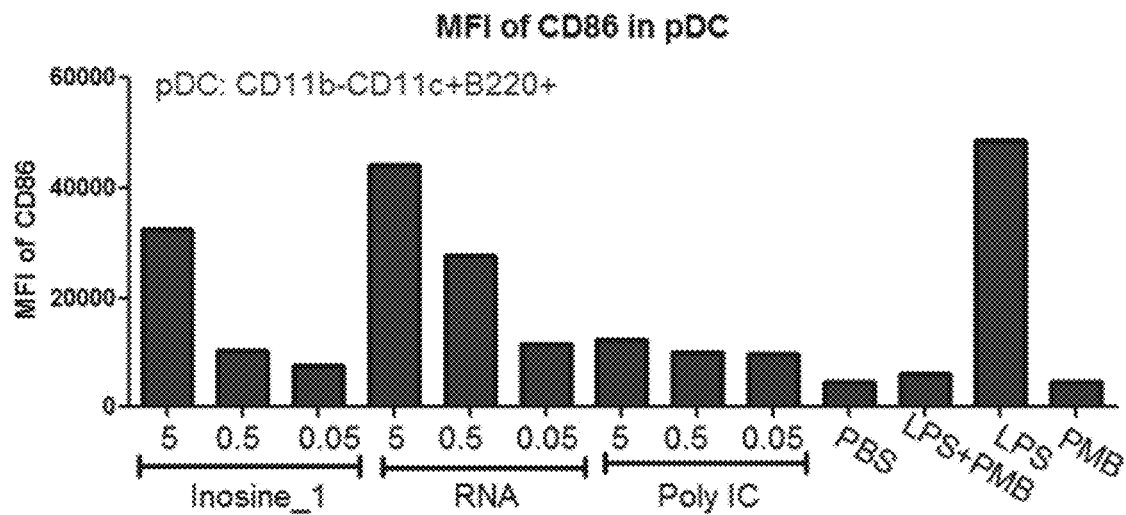
FIG. 4A shows the ex vivo splenocyte stimulation.
Figure 4B:
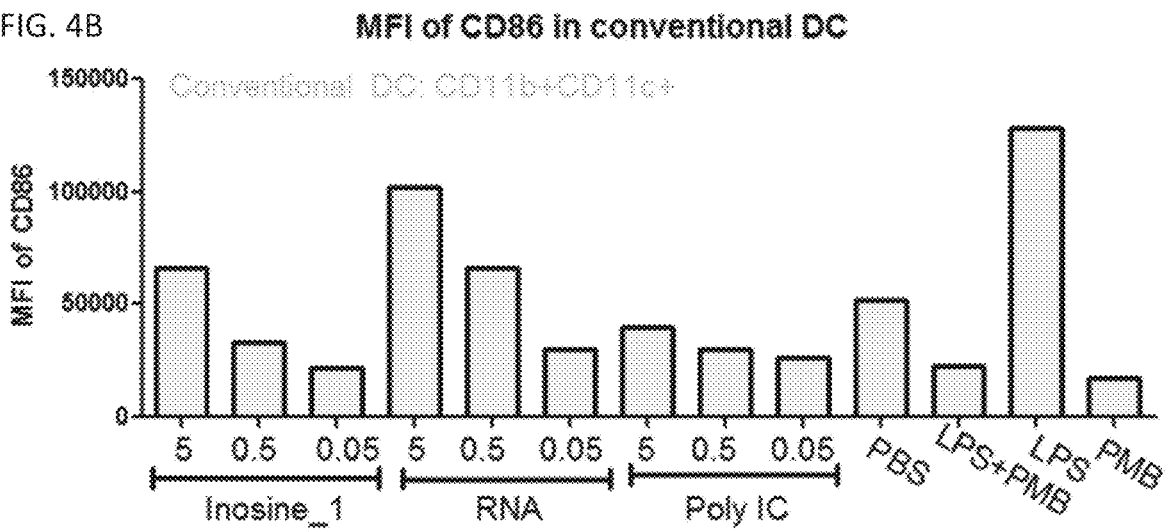
FIG. 4B shows ex vivo splenocte stimulation in plasmacytoid DC. CD86 activation in Dendritic cell. RNA origami activate antigen presenting cells (DC and plasmacytoid DC (pDC)). Mean fluorescence intensity of CD86 in each cell population is plotted.
Figure 5A:
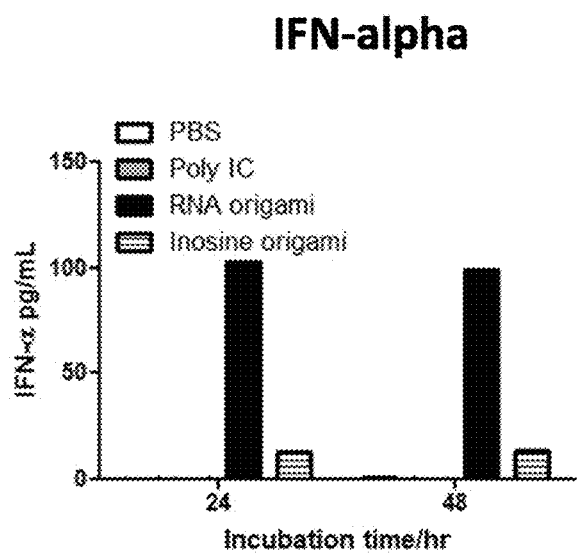
FIG. 5A shows cytokine release in ex vivo splenocyte cell culture supernatant upon stimulation, where RNA origami induces production of IFN-α.
Figure 5B:
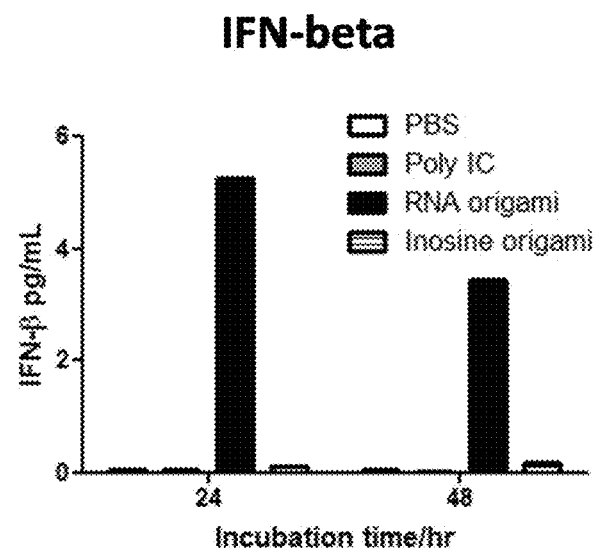
FIG. 5B shows cytokine release in ex vivo splenocyte cell culture supernatant upon stimulation, where RNA origami induces production of IFN-b.
Figure 6:
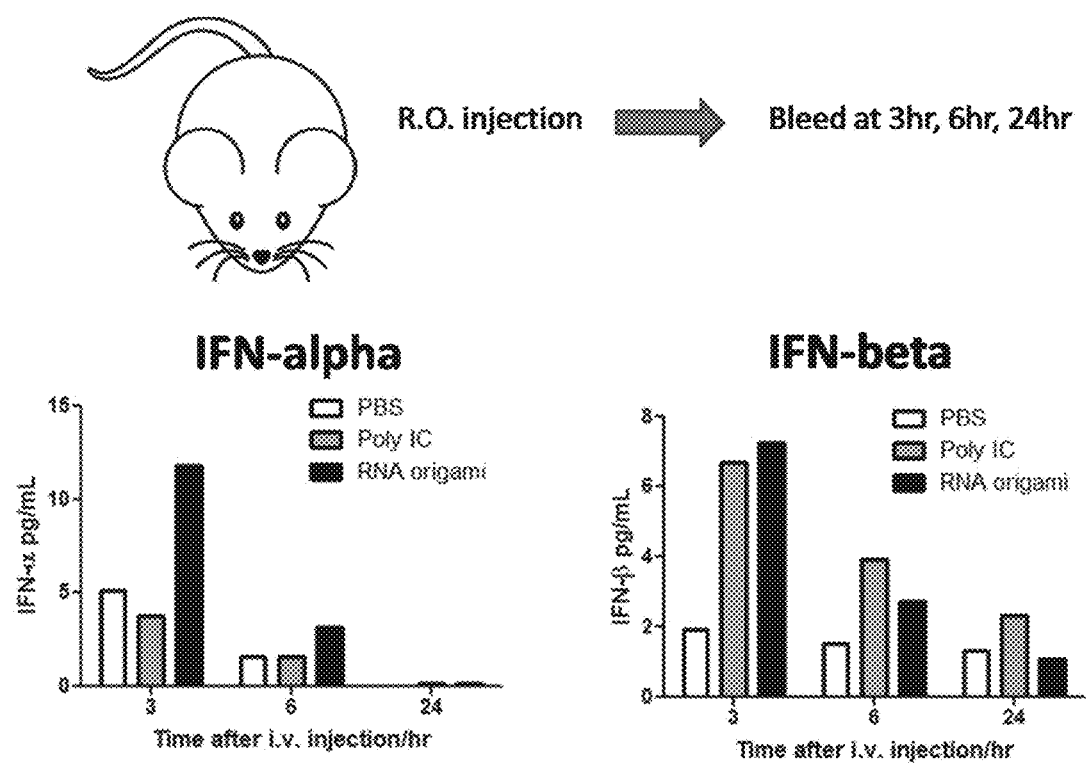
FIG. 6. Serum cytokine in mice injected with RNA origami. Similar to the finding on in vitro stimulation, an intravenous injection of RNA origami through retro-orbital route resulted in a transient elevation of IFNa/b.
Figure 7:
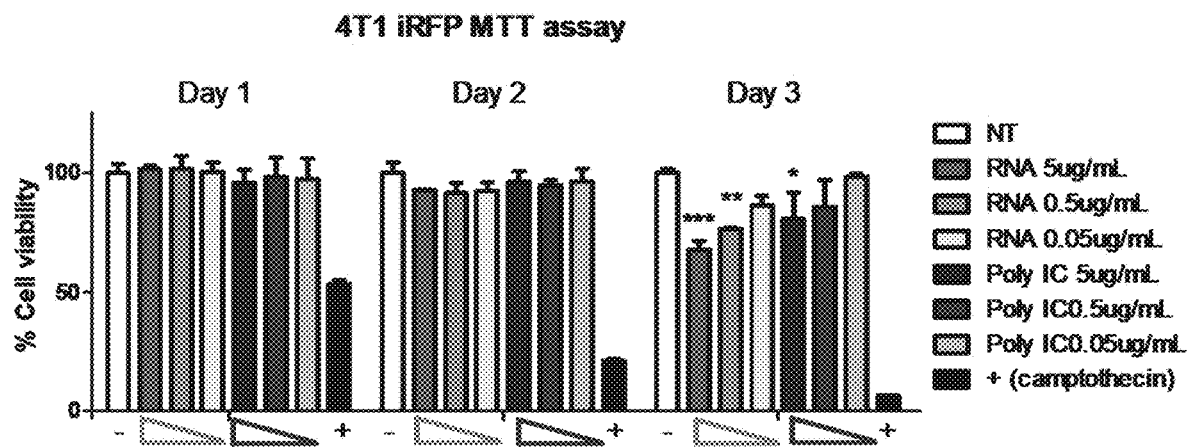
FIG. 7. Influence on tumor cell viabilities. After three days of incubation, RNA origami was found to reduce the viability of 4T1, a mouse breast cancer cell line, in vitro. The delayed inhibitory effect might have been mediated through the production of pro-inflammatory cytokines by the tumor cells after their exposure to RNA origami. RNA origami exerted little or minimal effect on the viability of certain other mouse and human tumor cell lines tested in vitro (not shown). Within each grouping, the following are included from left to right: NT (no treatment), RNA (RNA origami) 5 μg/ml, RNA (RNA origami) 0.5 μg/ml, RNA (RNA origami) 0.05 μg/ml, polyIC 5 μg/ml, polyIC 0.5 μg/ml, polyIC 0.05 μg/ml, +(camptothecin).
Figure 8:
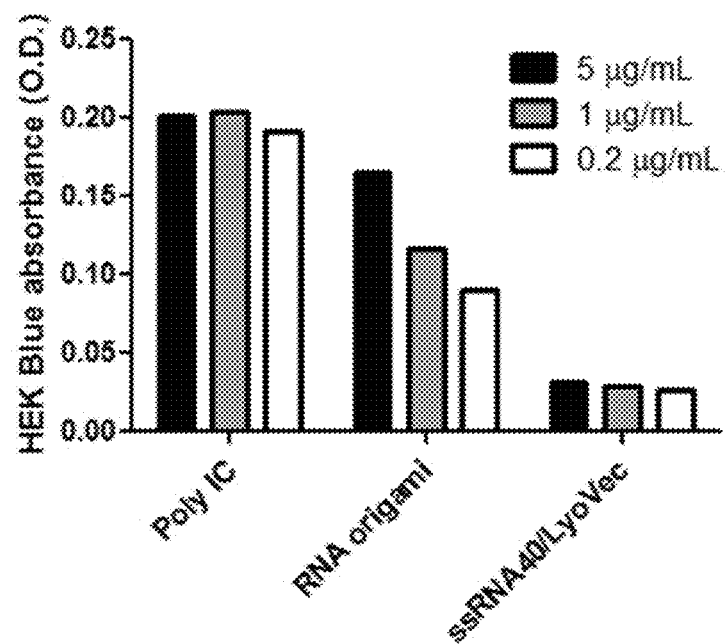
FIG. 8. TLR3 agonist. RNA origami showed as a TLR3 agonist in a reporter cell line, HEK-Blue™-mTLR3 cells, although its activity is not as strong as polyIC.
Figure 9A:
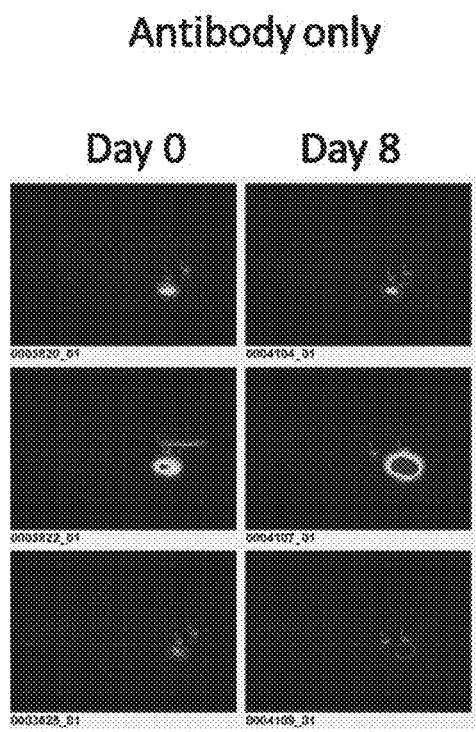
FIG. 9A shows the anti-tumor immunity in vivo where the antibody only is shown.
Figure 9B:
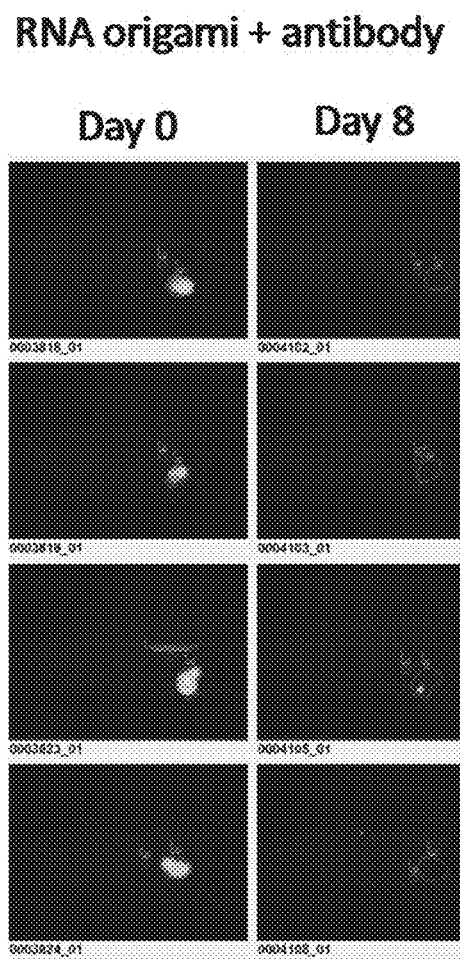
FIG. 9B shows the anti-tumor immunity in vivo where the RNA origami+ antibody is shown. Track in vivo tumor growth with A20-iRFP model.
Figure 10:
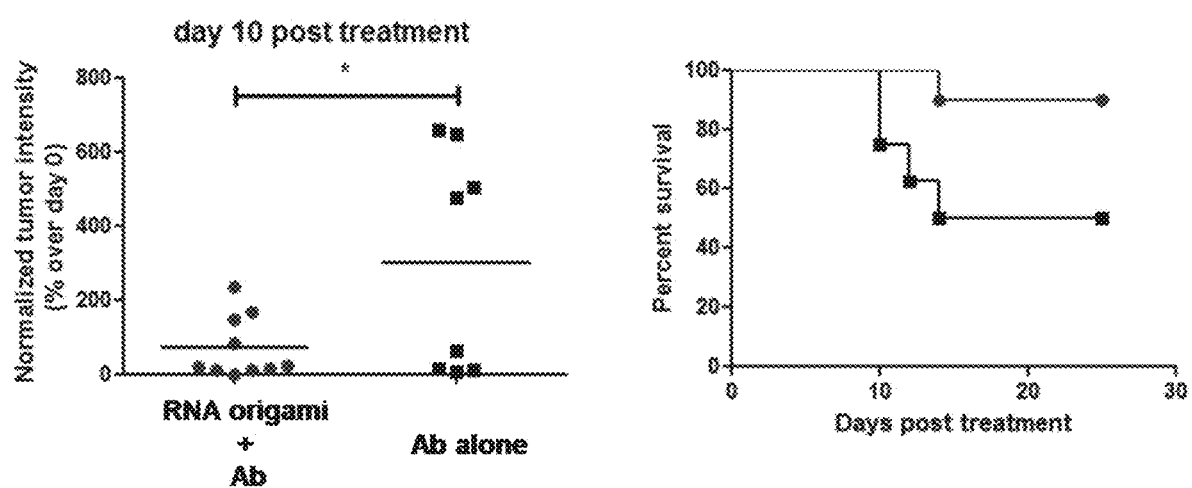
FIG. 10. Tumor reduction upon treatment with RNA origami.

As described in FIG. 1, a plasmid containing an ssRNA origami gene was linearized and the ssRNA was in vitro transcribed using T7 RNA polymerase. The purified RNA molecule was then self-assembled into the ssRNA origami nanostructure. The properly-folded RNA origami was shown to be resistant to nuclease digestion and contained regions of both dsRNA and ssRNA, which may serve as pathogen associated molecular patterns. Specifically, in vitro RNase digestion experiments were conducted and the RNA origami was found to exhibit higher nuclease resistance than the unfolded ssRNA with the same sequence as the RNA origami (FIG. 2). In addition, the immuno-stimulating effects of RNA origami was tested using an ex vivo splenocyte stimulation assay and enhanced stimulatory activity mediated by RNA origami over PolyIC was observed (FIG. 3-FIG. 5). Similar to the in vitro findings on stimulation, an intraveneous injection of RNA origami through a retro-orbital route resulted in a transient elevation of IFNa/b in mice (FIG. 6).Upon prolonged incubation, the RNA origami were also found to reduce the viability of some tumor cells in vitro (FIG. 7). As shown in FIG. 8, the RNA origami acted as a TLR3 agonist in the HEK-Blue™-mTLR3 reporter cell line. Finally, anti-tumor immunity was evaluated in vivo using an A20-iRFP model, which allowed tumor growth to be tracked in vivo (FIG. 9-FIG. 10). In these experiments, mice were either administered an antibody alone or the antibody in combination with RNA origami. As shown in FIG. 9 and FIG. 10, tumor reduction was observed upon treatment with RNA origami, which was greater than with the administration of antibody alone.

Taken together, these results indicate that the RNA origami can function as agonists of pattern recognition receptors, such as TLR3 and TLR7 in immune cells, and serve as a new line of adjuvants. By using an established mouse tumor model, this platform may be further explored for the construction of tumor-specific vaccines.

Materials and Methods

Materials

Restriction endonucleases EcoRI (5,000 units), XhoI (5,000 units) and HindIII (5,000 units), T7 and T3 RNA polymerases (5,000 units), NEB 10-beta competent E. coli were purchased from NEW ENGLAND BIO LABS INC. Pureyield plasmid miniprep system and the Wizard SV Gel and PCR Clean-UP System were purchased from Promega (www.promegA.com). RNA Clean and Concentrator-25 was purchased from Zymo Research (www.zymoresearch.com).

RNA Nanostructure Design

RNA rectangle origami nanostructure and RNA sequence were designed using the Tiamat software (Yanlab.asu.edu/Tiamat.exe).

Artificial RNA sequence was generated by using the following criteria in the Tiamat software: (1) Unique sequence limit: 8 nt; (2) Repetition limit: 6-8 nt; (3) G repetition limit: 4 nt; (4) GC content: 0.45-0.55. Once sequences were generated, a few nucleotides were adjusted to eliminate the restriction enzyme targeting sequences (e.g. by EcoRI, EcoRV, HindII and XbaI) for cloning purposes. A T7 promoter sequence followed with three consecutive Gs were manually incorporated onto the 5' end of the DNA template (SEQ ID NO: 2) in order to facilitate efficient in vitro transcription reaction. The dsDNA template was synthesized by BioBasic Inc. and cloned into the pUC19 vector through EcoRI and HindII restriction sites.

RNA Strand Synthesis

The plasmid containing the ssRNA nanostructure gene was linearized by using a HindII enzyme (New England Biolabs) and the linear plasmid was purified by using a Phenol/chloroform extraction and ethanol precipitation. The in vitro transcription reaction was carried out by using the T7 RiboMAX Express Large Scale RNA Production System (Promega), following the manufacturer's instructions. For inosine containing RNA preparation, additional 5 mM Inosine-5'-triphosphate (TriLink BioTechnologies) was added to the in vitro transcription reaction. The RNA molecules were then purified via a RNA Clean & Concentrator-25 kit (Zymo Research). After purification, the ssRNA was annealed using the same program as ssDNA origami. The RNA molecule produced from DNA template SEQ ID NO: 2 had the RNA sequence of SEQ ID NO: 1.

RNA Origami Nanostructure Assembly

The purified RNA molecule was diluted to 20 nM in 1×PBS buffer (20 mM Sodium phosphate, 130 mM Sodium chloride, pH 7.4). The resulting solution was annealed from 65° C. to 25° C. with a cooling ramp of 1° C. per 20 minutes to form the desired structures. The assemble RNA origami nanostructure was concentrated to the desired concentration using an Amicon Ultra-0.5 mL centrifugal filter (Millipore, 100 kDa cut off).

Atomic Force Microscope characterization

RNA origami was imaged in "ScanAsyst mode in fluid," using a Dimension FastScan microscope with PEAK-FORCE-HiRs-F-A tips (Bruker Corporation). After annealing, 2 µl of each sample was deposited onto a freshly cleaved mica surface (Ted Pella, Inc.), and left to adsorb for 1 minute. Then, 80 µl of 1×TAE-Mg buffer and 2 µl 100 mM of a NiCl2 solution was added onto the mica, and 40 µl of the same buffer was deposited onto the microscope tip. The samples were then scanned by following the manufacturer's instructions.

Animals

Female BALB/c mice were obtained from Charles River Laboratories and maintained in a pathogen-free animal facility at the Arizona State University Animal Resource Center. All mice were handled in accordance with the Animal Welfare Act and Arizona State University Institutional Animal Care and Use Committee (IACUC). Before experimental treatment, the mice were randomly distributed in cages and allowed to acclimate for at least 1 week prior to vaccination.

Splenocyte Isolation and Stimulation

Mice were euthanized with carbon dioxide asphyxia, and the spleens were removed and sterilized by quickly dipping in 70% ethanol for 1 s before transfer to sterile RPMI-1640 medium supplemented with 10% fetal bovine serum (FBS) in the biosafety cabinet. Spleen was cut on one end, and a thin, sealed L-shaped glass tube was used to push spleen marrows out. The extracted spleen cells were pelleted and washed by spinning at 380×g for 3 min in the sterile RPMI-1640 medium described above, and red blood cells were depleted by ACT lysis buffer (combination of 0.16M NH4Cl and 0.17 M Tris [pH 7.65] at a volume ratio of 9:1, pH adjusted to 7.2 with 1 M HCl, and filter sterilized). After washing twice in RPMI-1640 medium supplemented with 10% FBS and antibiotics, the splenocytes were seeded in 12-well plates at a density of $4 \times 10^6$ cells/mL. RNA origami, Inosine-incorporated RNA origami, or other adjuvants are added into each well at desired concentrations (5 µg/mL, 0.5 µg/mL, or 0.05 µg/mL), 50 ng/mL lipopolysaccharide (LPS) was added to the positive control well and Polymyxin B (PMB) is added into each well except for the LPS alone well at final concentration of 100 µg/mL to prevent endotoxin contamination. 24 hours or 48 hours after stimulation, cells were harvested, labelled for surface markers, and analysed by flow cytometry.

Flow Cytometry

Stimulated splenocytes were harvested by spinning down at 380×g for 3 min, and supernatants were saved for cytokine analysis. Pelleted cells were washed once with 1×PBS, and labeled with Zombie Violet viability dye (Biolegend) at room temperature for 15 min. After washing twice in staining buffer (1×PBS, 2% BSA, 0.01% sodium azide), cells were incubated in the following antibody cocktail containing FcR block: (a) FITC anti-mouse CD4, PE anti-mouse CD3, PE/Cy5 anti-mouse CD69, and PE/Cy7 anti-mouse PD1; b) FITC anti-mouse CD11b, PE anti-mouse CD86, PE/Cy5 anti-mouse B220, and PE/Cy7 anti-mouse CD11c. After 30 min incubation at 4° C., cells were washed twice in staining buffer and resuspended in 200 uL staining buffer. Then each sample was analyzed on a FACSAria II instrument at Biodesign Institute, Arizona State University. Live cells were defined as Zombie Violet-low cell population, and CD4 T cells were gated as CD3+CD4+ live cells, CD8 T cells were gated as CD3+CD4-live cells. Percentage of CD69+ cells in CD4 T cell population and CD8 T cell population were plotted for T cell stimulation measurement Plasmacytoid dendritic cells (pDC) were defined as CD11b−CD11c+ B220+ live cells, and conventional dendritic cells (DC) were defined as CD11b+CD11c+ cells. Mean fluorescent intensity of CD86 in each DC cell population is plotted as an indicator of DC stimulation status.

Cytokine Analysis

Cytokine release in ex vivo splenocyte cell culture supernatant was measured by the mouse Procarta IFN 2-plex featured assay of Eve Technologies (catalog no. MIFN-02-103). For serum cytokine analysis, 100 uL of RNA origami (25 µg), PolyIC (25 µg) or 1×PBS were i.v. injected to naive mice through retro-orbital route, and mouse serum were collected at 3 hr, 6 hr, and 24 hr post injection by cheek-vein bleeding. Blood was spin down at 7000 rpm for 10 min at 4° C., and measured by the mouse Procarta IFN 2-plex featured assay of Eve Technologies (catalog no. MIFN-02-103).

Cell Viability Test

Viability of cells after incubation with RNA origami was analyzed by MTT assay, (Vybrant®MTT cell proliferation assay kit from Thermo Fisher) following manufacture's protocol. Camptothecin (Sigma-Aldrich, catalog no. C9911) at final concentration of 5 µM served as the positive control, because it induces apoptosis.

TLR3 Agonist Test

A reporter cell line expressing mouse TLR3, HEK-Blue™ mTLR3 cells, was purchased from Invivogen. Agonist activity of RNA origami and other adjuvants were quantified by the absorbance of HEK-Blue medium after co-incubation of these adjuvants with cells, following manufacture's protocol. ssRNA40/LyoVec™ purchased from Invivogen served as negative control.

A20-iFRP-OVA Tumor Model

Figure 11:
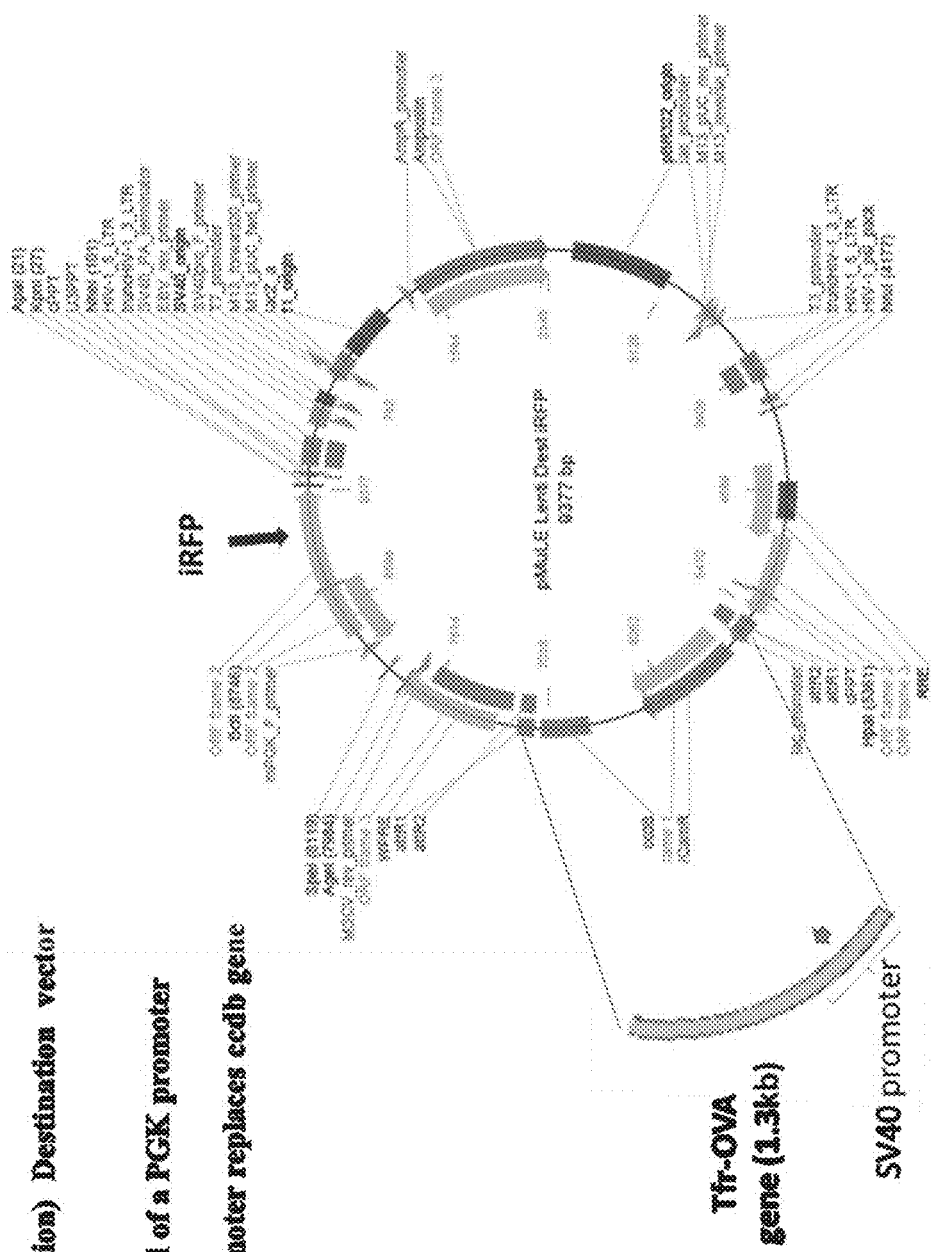
FIG. 11. MuLE (Multiple Leniviral Expression) Destination Vector.

A20, mouse B cell lymphoma cells, were transduced with lentiviral vector that was constructed to express near-infrared fluorescent protein (FIG. 11), iRFP, and oval albumin using LENTI-Smart™ transduction kit from Invivogen by following manufacture's protocols. Cell-sorting was carried out on BD FACSAria II at Biodesign Institute, Arizona State University, to isolate A20-iRFP cells with the top 1% fluorescent intensity for subsequent cell culture. Bright and stable expression of iRFP in A20 cells were confirmed by flow cytometry and Pearl small animal imaging system (LI-COR, San Diego, Calif.). For tumor inoculation, BALB/c mice were shaved at the left flank and injected s.c. with $10 \times 10^6$ A20-iRFP cells. 7-10 days post injection, mice were imaged under the Pearl small animal imaging system, and mice bearing tumors of similar near-infrared intensities were randomized into different groups for subsequent treatments.

For treatment, mice were injected with 25 ug RNA origami in 50 uL PBS, or 50 uL PBS through intratumor injection on day 0. Anti-PD1 antibody (Biolegend, catalog no. 114108) were injected into mouse tumors on day 2 and day 4, at a dose of 2.5 ug per injection. Tumor growth were tracked every other day and tumor size was quantified by measuring the near-infrared fluorescent intensity using Image Studio™ software from LI-COR. The results showed that at day 10 post treatment, the cohort treated with RNA origami with the anti-PD1 antibody exhibited a smaller tumor size than the cohort treated with the anti-PD1 antibody alone (FIG. 10). In addition, the survival rate was surprisingly greater for the cohort treated with RNA origami with the anti-PD1 antibody (round dots) compared to the cohort treated with the anti-PD1 antibody alone (square dots) (FIG. 10). The cohort treated with the combination of RNA origami with the anti-PD1 antibody only had a 5% drop in survival, whereas the cohort treated with the anti-PD1 antibody alone had a 50% drop in survival at 25 days post-treatment.

RNA Nanostructure Sequence for One Embodiment of NR₁

(SEQ ID NO: 1)
GGGAGAGAGCUCGAGCGAACACUAGCCACUUGAUCACGCUGAGCGCUCGU
ACAAUGAAACACAGGUGUGUCAGUGCUAUGCACGUUCGAAGAGCUGUAUC
AGCGUUCGUGUGAAUGAGUUCAACGGAGUGUUGACUAAGCCGGUUGCUAC
AUUUCUGUAGCACACAUAGUCAAGAUUUGCACCAGACGAUACUCUCCCUC
AGUCCUGUUUAUGCAAGUCGUCGUAGUCCUGACGUACUUCCUAAGCUCGU
CACUGUACUGAUGAUUCCACUGAUCAAGAUGCACGUAUCUUCAGUUUCCU
GAAGAUCGGAGUAGGCACUAUAAUCGACAAGUAACGCUUACGAUUCCAUC
ACGAGUGACUUACCUGAACCAUAACUGACAAGGGACCACGCAGAGGUCAU
ACUCACAGGACUUCAAAUCUUGAGUCGGGUUCGAUCAUUUCUGAUCGAGA
CACCAGUGUGAGGUAAUCGUACGUCACUUGAUAGGAGCUCUAAGUAGAGU
UGAGAGCCUGUUAACUAGACACGAGUAACGAGGUUAGCCUGUACGAGAUA
UCGGGCUAUAGUGCGGACACGAUUGCACCAUUUCUGGUGCAACGAAGGUG
AGCAUGUAUGGACAGGUCAGUGUGACUCAAGUCGAUAGUCCAAGUAGGUU
AUCGACUCGCAUAGCUCAAUGACGUCAUCGCCAGAGUAUCUAGGUGUCU
ACCUCACGAAUCGCGUCGUUACAUUUCUGUAACGCUCAUACCGUGCUGAU
CUAUGGGACACGUCGCUUAUUCUUGGGUCAUGACAGUUGCCACAAACAAG
GCACGACCUCACACCUGCGAACUUCAAGCGUUAGGCUGACGUUACAUGCU
UGCGUGCACUGAUUCGUUUCCGAAUCAGAGACCUACGAAGCCAGAGUUCG
UUCACUAUCAUAAGUGCACUGAUGCAUUUGUGCCAACAUUGAAGGCAUCG
AGAUAAACAGCCGUCUUAAUCAAGUGAGCACCUGAGAUCAGCAUGAUUCG
UCUAUUUCUAGACGAAUCAACUUCCAUUCAGGUGCCUUGCUACUUAAGAC
GGGAUUAACUCUCGAUGCAACGUGCAUUGGCACAACUCGUGAUGUGCACU
UUCACACUGGAACGAACUCUGGCUUCGUAGGUCUGUUUGUCAUUUCUGAC
AAACUGCACGCACUGUUAGUACGUCAGCCACUUAACCGAAGUUCGUCAUA
AGUAGGUCGUGCGACUACGAUGGCAACUUCUACUUACCAAGAAUAAGCGA
CGUGUCCCAUAAUGGAAGUCGGUAUGAGGUAUGACUUUCGUCAUACACGC
GAUUCCACAAUGUGACACCUAACGUUUGAGGCGAUGACCUGAUACAAGCU
AUGCAUGGUUCAAACCUACUUGGACUAUCGACUUGAGAUGAUAGUACCUG
UCCAACUAACAGCACCUUCGAUACCUCGUUUCCGAGGUAUUCGUGUCCUG
UGUCAGGCCCGAUAUUAAUGUGUGGCUAACCCUUAGGAACGUGUCUAGUU
AACAGGCUCUCAACGUCAUGACGAGCUCCUAGUAGCAAGCGUACGAUACA
UUGUGACUGGUGUCUACUGGAUUUCUCCAGUAACCCGACUCCGACUACAA
AGUCCUGACUCAUUCACCUCUGCGUGGUCCCUUGUCAGUUGAGUCGAUGG
UAAGUCAAUGCAUCAGGAAUCGUGGUUAAGUCUUGUCGAUCUGACACACU
ACUCCGCUGUCCUGUUUCCAGGACAGACGUGCAUUAGCAGUUGUGGAAUC
AUCAGUACAGUGACGAGUCGUUACUGUACGUCAGCUUGUUUGCGACUUGC
AGUUAAUCGACUGAGGGUCAAACGUGUCUGGUGUGUAGUCGGACUAUGUG
ACGUUCAUUUCUGAACGUACCGGCUUAGUCAACACUCCGUUGAUGAGUAU
GACACGAACGAGUCAUUGGCUCUUCGCUUCAAUGUAGCACUGAACUUAUG
AUGUUUCAUACACAUUACGCUCAGCGAACUGCUAUGGCUAGUGUUCGGAU
CC

DNA Sequence Encoding RNA Nanostructure Having SEQ ID NO: 1

(SEQ ID NO: 2)
GGGAGAGAGCTCGAGCGAACACTAGCCACTTGATCACGCTGAGCGCTCGT
ACAATGAAACACAGGTGTGTCAGTGCTATGCACGTTCGAAGAGCTGTATC
AGCGTTCGTGTGAATGAGTTCAACGGAGTGTTGACTAAGCCGGTTGCTAC
ATTTCTGTAGCACACATAGTCAAGATTTGCACCAGACGATACTCTCCCTC
AGTCCTGTTTATGCAAGTCGTCGTAGTCCTGACGTACTTCCTAAGCTCGT
CACTGTACTGATGATTCCACTGATCAAGATGCACGTATCTTCAGTTTCCT
GAAGATCGGAGTAGGCACTATAATCGACAAGTAACGCTTACGATTCCATC
ACGAGTGACTTACCTGAACCATAACTGACAAGGGACCACGCAGAGGTCAT
ACTCACAGGACTTCAAATCTTGAGTCGGGTTCGATCATTTCTGATCGAGA
CACCAGTGTGAGGTAATCGTACGTCACTTGATAGGAGCTCTAAGTAGAGT
TGAGAGCCTGTTAACTAGACACGAGTAACGAGGTTAGCCTGTACGAGATA
TCGGGCTATAGTGCGGACACGATTGCACCATTTCTGGTGCAACGAAGGTG
AGCATGTATGGACAGGTCAGTGTGACTCAAGTCGATAGTCCAAGTAGGTT
ATCGACTCGCATAGCTCAATGACTGTCATCGCCAGAGTATCTAGGTGTCT
ACCTCACGAATCGCGTCGTTACATTTCTGTAACGCTCATACCGTGCTGAT
CTATGGGACACGTCGCTTATTCTTGGGTCATGACAGTTGCCACAAACAAG
GCACGACCTCACACCTGCGAACTTCAAGCGTTAGGCTGACGTTACATGCT
TGCGTGCACTGATTCGTTTCCGAATCAGAGACCTACGAAGCCAGAGTTCG
TTCACTATCATAAGTGCACTGATGCATTTGTGCCAACATTGAAGGCATCG
AGATAAACAGCCGTCTTAATCAAGTGAGCACCTGAGATCAGCATGATTCG
TCTATTTCTAGACGAATCAACTTCCATTCAGGTGCCTTGCTACTTAAGAC
GGGATTAACTCTCGATGCAACGTGCATTGGCACAACTCGTGATGTGCACT
TTCACACTGGAACGAACTCTGGCTTCGTAGGTCTGTTTGTCATTTCTGAC
AAACTGCACGCACTGTTAGTACGTCAGCCACTTAACCGAAGTTCGTCATA
AGTAGGTCGTGCGACTACGATGGCAACTTCTACTTACCAAGAATAAGCGA
CGTGTCCCATAATGGAAGTCGGTATGAGGTATGACTTTCGTCATACACGC
GATTCCACAATGTGACACCTAACGTTTGAGGCGATGACCTGATACAAGCT
ATGCATGGTTCAAACCTACTTGGACTATCGACTTGAGATGATAGTACCTG
TCCAACTAACAGCACCTTCGATACCTCGTTTCCGAGGTATTCGTGTCCTG
TGTCAGGCCCGATATTAATGTGTGGCTAACCCTTAGGAACGTGTCTAGTT

-continued

```
AACAGGCTCTCAACGTCATGACGAGCTCCTAGTAGCAAGCGTACGATACA
TTGTGACTGGTGTCTACTGGATTTCTCCAGTAACCCGACTCCGACTACAA
AGTCCTGACTCATTCACCTCTGCGTGGTCCCTTGTCAGTTGAGTCGATGG
TAAGTCAATGCATCAGGAATCGTGGTTAAGTCTTGTCGATCTGACACACT
ACTCCGCTGTCCTGTTTCCAGGACAGACGTGCATTAGCAGTTGTGGAATC
ATCAGTACAGTGACGAGTCGTTACTGTACGTCAGCTTGTTTGCGACTTGC
AGTTAATCGACTGAGGGTCAAACGTGTCTGGTGTGTAGTCGGACTATGTG
ACGTTCATTTCTGAACGTACCGGCTTAGTCAACACTCCGTTGATGAGTAT
GACACGAACGAGTCATTGGCTCTTCGCTTCAATGTAGCACTGAACTTATG
ATGTTTCATACACATTACGCTCAGCGAACTGCTATGGCTAGTGTTCGGAT
CC
```

RNA Nanostructure Sequence for One Embodiment of NR$_2$ (SEQ ID NO: 9)

```
5'-CACGAACUCAUCCUCACGCCGCCGGUCGCGUGCGGCGCCGGCAG
AAGGACCUGAUGCAUCGAGCGGUGACAGCGCCACCGGAGUAGCUCAGUUA
UUCGAUUCAGUAUAUUACGUAAUAUACGGCGAGAAGUUGCAGCAGUGCGC
UGUAUUUUAGCAUGUCGCGCUAACUACGAUGAUUGGCAAUAAGAUUACGA
CCGCUAUCUCAUGGCUUAUCAAAGUGGGCAAGGUCUUGCCCACGGCGUUG
ACGUCCGACCCGUCGUUAAGUGUCAGAGUCGUGUACCCUUAGAUCUGGC
CACGCACGAGGUCCACCAUGGGUACUCGCGUCAGGACAGUAACCUUACUG
UCGCCGCUCCGAGCGCAUAUUUCGCCUCAGGCGGGCGGUUACCCGUUAAU
CUUUAGGCAAACUACGCACGGGCUUGUUUUGUGUCUCCACUCUCGGGUA
CUUUGGAGUACCCCGGUAGAAGAAUGUUCCGGUUCGCGUGCGGGCGGCCG
UUACACUGGGCGACUGCAUAGGGCCGCCCGCCCGCCUCGCCCUAAAUUUC
ACCCAUUAAGCGAGAAAGCAUUCUCGCAACUGGGUAUGGACUUGGGGUGU
CCUGGAUUCGAUCACGCACCGGUCGCCGAAGUGGCGGGAAGAGCACCCCU
ACGUCGGGUCUUACAGGACACGCGACCCUACUUCGGCGUACCCCCCGGUA
CGCCCGCGCCCGCAGAGCGGUCGAUUGGUCACACGGUGGAAGUGAGUCUG
UUGUCGCCGUUUCUACAAUCCGUCUGCUGCAACGGGCCAGGUUGGUUAUU
AAUAACCAAAGUGCCGGAGCUCCGCCCCGUCAUAGGUGAUCCACAGCGGG
UAAUAUCUUACCUGCUCCUUCAGAGGGCGGGGCAAGGGCGUCGGACGAGU
GUAUUUGUUACGUCAUAACGUAACACUACGGCAUCGGGUGCUAGCGCCAG
ACCGCGCGCACUGGCGGCGAGAGAGUCUUAUACGCCAGGUGCUAGCCAAU
AUGCGCUCACUUAAGGUGUUCAUGUACAUGAACAAAAGCUACAUGAGGAC
GGCUGCUUGAUUCCAACAGGCUACGGUGUUUCGGCUGGCCAAAUAAGU
CGAGGAGGCGGGAACAUUUGACGACUCUCUGGUAUCCUUACCAGAGGGGU
GAACUAACCAAAUUCCUGGAAGAAUUGGUCCUAUAGCCCUAUGAGCUAGG
AACGGUCUGUUUUCCGAGACCGUCAAGUCCAGUUGGCGAUGGUGGGCG
UCCCCACCAUGUAGGCUACCUUGUCGUGACCGAAUUCCGGCCCAGAGAAU
UGGGGCAACGGCGCACUUCCUUCUGCCGCCCUCCCCGCUCUGCAGGCGCC
ACAGCUCGCGCACGAGCUGUCCCUACGCCAGAAGGGCUCCUCAUGCGAAG
UACACCGUCAGUAAGUCUGGCCCUCUAAAAUAAAUACCUUGCCGGAGCGA
GGCACUGGGAACGUAGGGACGUUCCUCUAAGUAUGCACAAUCCACAUAAG
CCGACGAAUGCGCCGCACUGACGUGAAACUGGACUUGGCUGACACUCAAA
AGGCCGCACCCGAGGCCCCCCGAUGUGGUCACGACCACAUCUCGCGCCGU
UGUAAGGUCGAGCCCUUCAACUAAUAGUUUUAAACCCACUCGGUAGGGUU
CCCUAUAACCCAAAACCCCGCCUGUUUGGGCGCGUCCUCAUAGGUGCCUA
GGCAAGGCCGCUUGCCUUGGUUGCGGGGCAGAUUUUCCUAACUAAUCGUC
CACCGCGAAGGCUCCCUGAAAAGCACCCGCCCGCACACGUGUAUUUGGUU
AUGGUCUUCUACGAUUGGACGCAAUCGUAUCCUACCCCGUCGGGGCCGGC
CCGCGACAACAGGUGAACGACCUUGGCUUGGGCAUGUCAUCGGACGGAUA
GCAAGCACCGAAUCCACAACCUGUCGACAAGGCUGAUCCUCCCUCCGGGG
AGGAUCAGUGGGCAAUACAGGUUGUUAGUCCGGUGCUUGCUCGCUCGAUA
AGGUCGUACCGUGUGUGUCGCGGGCCCUUCUGGCCGGGGUAGGAUCAGCA
CCAAAUGGUGCUGAGAAGACCAUUAAAGGGUACACGUGUCAACAUAGAUA
GGAUUUUACGCCGGGUGCUUUUGUAGUUAGCUUCGCGGUGGAUCACCAGU
UAGGAGUCGUGGAUUGGCAACCACAUUAACGACGGUUAAUGAGGCACCUA
AAUCAUUUCGCCCAAAUCUACCAAGUUUUGGGUUAAGGGUAACCCUACCC
GCGCGGUUUAAAACGACCUUACAACGGCGCGAACGCCAUGUACGCAUGGC
GUGGGGGGCCGACCGAAUGGCCUUUUGGGGUAUGCCCAAGUCCAGAUUAA
CGUCAGUGCGUUGGAAAUGUCGGCUUAUAGCAAAUCUGCAUACUUAGAGU
GACGCUAGAGCGUCACCAGUGCCUCUGAUUCUUAAGGUAUUCCUCAGCCU
CCCUCUAACUAUGCACAGGGCCAGAUCGCCCAGCGGUGUACACCAAUUCA
GGAGCCGGCCCCGAGUAGGGUGCAGAUGUGGGCAUCUGCAGGCGCCUGGG
UCGGCUGGAGGGCGGGUGUCGAAAGUGCGCCGGCGACCGAAUUCUCUGGG
CCGGAAUUAACGGUUUCCCGAGUGGCGGUCAAUUGCCCAUAGCCUACAGC
GACACGCAGGUGUCGCUCCGCCAACGAAUUAGUACGGUCUCUCCGGUGGA
GACCGUUCCUACAGACUCGGGCUAUAGGUUCGCAUGUUCCAGGAACCCUU
UAAGUUCACCCCUGCACCGAGGCCGGUGCAGAGUCGUCAGACGGGCGCGC
CUCCUCCUUAUUGCUGGCCAGCUCCGGUAAGAUUAGCCUGGCGCAUUCCA
AGCAGCAAAUGAUUUGUAGCUUUAAUUAAGGCACCUUAAUUCCUUAAGUG
AUCGUCUCUUGGCUAGUCGUGCGUGUAUAAGACUCUCUCGCCGCCAGUGG
AGUGGGUCUGGCGCUAAUUCGGUCUGCCUAGGUUCCUACCUUUGUAGGA
ACAAUACACUCUAACUAGGCCCUUGCCUGCGUAGUUGAAGGAGCAGUUCA
GAAACAACCCGCUGUGGACGAUUUAUGACGGAGGAAUCAUCCGGCACUUG
CUUUAUCGAUAAAGCACCUGGCCCGUUACGCAGGACGGAUUCGGGCGGCG
GCGACAAGCUCAUAACUUCCUCACCGUACCAAUCGAAGCCGACCCGGGC
GCGUCAGCGGGGUACCCGCUGAGAAGUAGGGAUGGGCGUCCUGGGUGCU
CUUCCCGCCACUUCGUUGCCCCGUGCGUGAUCGGACUAAGGACACCCACU
AAUUCUACCCAGUUCGUAACGAUAUCGUUACGUUAAUGGGUGAAAUAACU
```

-continued

GGCGAGGCGGGGUAGAAACCCUAUGCAGCUUACUGAUGUAACGGCCGGCG
UGACGCGAACCCGCCCGUCCUUCUACCGUGAUUGGUGUCCCAAUCACGAG
AGUGGCAUCAUGAGAUAAGCCCGCCGCCCUCUUGCCUAAAGUUUCACGGG
UAACCGUUGGUAGAAGGCGAAAGAGACGAUCGGAGCGGCCCCCGUCGCCU
GACGGGGCUGACGCGAGUACCCAUGGUCGCAUGCCCGUGCAGAUGGACCC
ACCUGGCGGCCAGAUCUAUAGGGACACCGACUGCAUACCCUAACGACGGC
UAGUUAGUCAACGCCGGGGCCGCACACGCGGCCCCUUUGAUAAGCGACAG
ACACAAGGUCGUAAUGACUUAUUCAAUCAUCCAGGGAGCCGCGACAUGGU
GCAAGGCAGCGCACCUGCGUAACUUCUCGCCCGAGGAUACUCAUCCUCGU
GAAUCGAAUUUAGGAGCUACGGAAAAACCGCUGUCACAUCCGGCCGCAUC
AGGUUCGACACCCGGCGCCGCGCCCAUCCGGCGGCGUGAGGAUGAGUUCG
UGUCCGCGGGCCACC-3'

DNA Sequence Encoding RNA Nanostructure Having SEQ ID NO: 9

(SEQ ID NO: 120)
5'-CATGAACTCATCCTCACGCCGCCGGTCGCGTGCGGCGCCGGCAG
AAGGACCTGATGCATCGAGCGGTGACAGCGCCACCGGAGTAGCTCAGTTA
TTCGATTCAGTATATTACGTAATATACGGCGAGAAGTTGCAGCAGTGCGC
TGTATTTTAGCATGTCGCGCTAACTACGATGATTGGCAATAAGATTACGA
CCGCTATCTCATGGCTTATCAAAGTGGGCAAGGTCTTGCCCACGGCGTTG
ACGTCCGACCCGTCGTTAAGTGTCAGAGTCGGTGTACCCTTAGATCTGGC
CACGCACGAGGTCCACCATGGGTACTCGCGTCAGGACAGTAACCTTACTG
TCGCCGCTCCGAGCGCATATTTCGCCTCAGGCGGGCGGTTACCCGTTAAT
CTTTAGGCAAACTACGCACGGGCTTGTTTTGTGTCTCCACTCTCGGGGTA
CTTTGGAGTACCCCGGTAGAAGAATGTTCCGGTTCGCGTGCGGGCGGCCG
TTACACTGGGCGACTGCATAGGGCCGCCCGCCCGCCTCGCCCTAAATTTC
ACCCATTAAGCGAGAAAGCATTCTCGCAACTGGGTATGGACTTGGGGTGT
CCTGGATTCGATCACGCACCGGTCGCCGAAGTGGCGGGAAGAGCACCCCT
ACGTCGGGTCTTACAGGACACGCGACCCTACTTCGGCGTACCCCCCGGTA
CGCCCGCGCCCGCAGAGCGGTCGATTGGTCACACGGTGGAAGTGAGTCTG
TTGTCGCCGTTTCTACAATCCGTCTGCTGCAACGGGCCAGGTTGGTTATT
AATAACCAAAGTGCCGGAGCTCCGGCCCGTCATAGGTGATCCACAGCGGG
TAATATCTTACCTGCTCCTTCAGAGGGCGGGCAAGGGCGTCGGACGAGT
GTATTTGTTACGTCATAACGTAACACTACGGCATCGGGTGCTAGCGCCAG
ACCGCGCGCACTGGCGGCGAGAGAGTCTTATACGCCAGGTGCTAGCCAAT
ATGCGCTCACTTAAGGTGTTCATGTACATGAACAAAAGCTACATGAGGAC
GGCTGCTTGATTTCCAACAGGCTACGGTGTTTCTGGCTGGCCAAATAAGT
CGAGGAGGCGGGAACATTTGACGACTCTCTGGTATCCTTACCAGAGGGGT
GAACTAACCAAATTCCTGGAAGAATTGGTCCTATAGCCCTATGAGCTAGG
AACGGTCTGTTTTTCCGAGACCGTCAAGTCCAGTTGGCGGATGGTGGGCG

TCCCCACCATGTAGGCTACCTTGTCGTGACCGAATTCCGGCCCAGAGAAT
TGGGGCAACGGCGCACTTCCTTCTGCCGCCCTCCCCGCTCTGCAGGCGCC
ACAGCTCGCGCACGAGCTGTCCCTACGCCAGAAGGGCTCCTCATGCGAAG
TACACCGTCAGTAAGTCTGGCCCTCTAAAATAAATACCTTGCCGGAGCGA
GGCACTGGGAACGTAGGGACGTTCCTCTAAGTATGCACAATCCACATAAG
CCGACGAATGCGCCGCACTGACGTGAAACTGGACTTGGCTGACACTCAAA
AGGCCGCACCCGAGGCCCCCCGATGTGGTCACGACCACATCTCGCGCCGT
TGTAAGGTCGAGCCCTTCAACTAATAGTTTTAAACCCACTCGGTAGGGTT
CCCTATAACCCAAAACCCCGCCTGTTTGGGCGCGTCCTCATAGGTGCCTA
GGCAAGGCCGCTTGCCTTGGTTGCGGGGCAGATTTTCCTAACTAATCGTC
CACCGCGAAGGCTCCCTGAAAAGCACCCGCCCGCACACGTGTATTTGGTT
ATGGTCTTCTACGATTGGACGCAATCGTATCCTACCCCGTCGGGGCCGGC
CCGCGACAACAGGTGAACGACCTTGGCTTGGGCATGTCATCGGACGGATA
GCAAGCACCGAATCCACAACCTGTCGACAAGGCTGATCCTCCCTCCGGGG
AGGATCAGTGGGCAATACAGGTTGTTAGTCCGGTGCTTGCTCGCTCGATA
AGGTCGTACCGTGTGTGTCGCGGGCCCTTCTGGCCGGGGTAGGATCAGCA
CCAAATGGTGCTGAGAAGACCATTAAAGGGTACACGTGTCAACATAGATA
GGATTTTACGCCGGGTGCTTTTGTAGTTAGCTTCGCGGTGGATCACCAGT
TAGGAGTCGTGGATTGGCAACCACATTAACGACGGTTAATGAGGCACCTA
AATCATTTCGCCCAAATCTACCAAGTTTTGGGTTAAGGGTAACCCTACCC
GCGCGGTTTAAAACGACCTTACAACGGCGCGAACGCCATGTACGCATGGC
GTGGGGGCCGACCGAATGGCCTTTTGGGGTATGCCCAAGTCCAGATTAA
CGTCAGTGCGTTGGAAATGTCGGCTTATAGCAAATCTGCATACTTAGAGT
GACGCTAGAGCGTCACCAGTGCCTCTGATTCCTAAGGTATTCCTCAGCCT
CCCTCTAACTATGCACAGGGCCAGATCGCCCAGCGGTGTACACCAATTCA
GGAGCCGGCCCCGAGTAGGGTGCAGATGTGGGCATCTGCAGGCGCCTGGG
TCGGCTGGAGGGCGGGTGTCGAAAGTGCGCCGGCGACCGAATTCTCTGGG
CCGGAATTAACGGTTTCCCGAGTGGCGGTCAATTGCCCATAGCCTACAGC
GACACGCAGGTGTCGCTCCGCCAACGAATTAGTACGGTCTCTCCGGTGGA
GACCGTTCCTACAGACTCGGGCTATAGGTTCGCATGTTCCAGGAACCCTT
TAAGTTCACCCCTGCACCGAGGCCGGTGCAGAGTCGTCAGACGGGCGCGC
CTCCTCCTTATTGCTGGCCAGCTCCGGTAAGATTAGCCTGGCGCATTCCA
AGCAGCAAATGATTTGTAGCTTTAATTAAGGCACCTTAATTCCTTAAGTG
ATCGTCTCTTGGCTAGTCGTGCGTGTATAAGACTCTCTCGCCGCCAGTGG
AGTGGGTCTGGCGCTAATTCGGTCTGCCGTAGGTTCCTACCTTTGTAGGA
ACAATACACTCTAACTAGGCCCTTGCCTGCGTAGTTGAAGGAGCAGTTCA
GAAACAACCCGCTGTGGACGATTTATGACGGAGGAATCATCCGGCACTTG
CTTTATCGATAAAGCACCTGGCCCGTTACGCAGGACGGATTCGGGCGGCG
GCGACAAGCTCATAACTTCCTCACCTGTACCAATCGAAGCCGACCCGGGC
GCGTCAGCGGGGTACCCGCTGAGAAGTAGGGATGGGCGTCCTGGGTGCT
CTTCCCGCCACTTCGTTGCCCCGTGCGTGATCGGACTAAGGACACCCACT

-continued

```
AATTCTACCCAGTTCGTAACGATATCGTTACGTTAATGGGTGAAATAACT
GGCGAGGCGGGGTAGAAACCCTATGCAGCTTACTGATGTAACGGCCGGCG
TGACGCGAACCCGCCCGTCCTTCTACCGTGATTGGTGTCCCAATCACGAG
AGTGGCATCATGAGATAAGCCCGCCGCCCTCTTGCCTAAAGTTTCACGGG
TAACCGTTGGTAGAAGGCGAAAGAGACGATCGGAGCGGCCCCCGTCGCCT
GACGGGGCTGACGCGAGTACCCATGGTCGCATGCCCGTGCAGATGGACCC
ACCTGGCGGCCAGATCTATAGGGACACCGACTGCATACCCTAACGACGGC
TAGTTAGTCAACGCCGGGGCCGCACACGCGGCCCCTTTGATAAGCGACAG
ACACAAGGTCGTAATGACTTATTCAATCATCCAGGGAGCCGCGACATGGT
GCAAGGCAGCGCACCTGCGTAACTTCTCGCCCGAGGATACTCATCCTCGT
GAATCGAATTTAGGAGCTACGGAAAAACCGCTGTCACATCCGGCCGCATC
AGGTTCGACACCCGGCGCCGCGCCCATCCGGCGGCGTGAGGATGAGTTCG
TGTCCGCGGGCCACC-3'
```

Example 2

TLR3 and TLR7/8 HEK-293T reporter lines were used to study whether RNA-origami could activate TLR3-signaling pathway and/or the TLR7 pathway. The results indicated that the RNA-origami activate TLR3-signaling pathway, but not the TLR7. Unlike dsRNA-mediated activation, the stimulatory activity observed was independent of transfection, which suggests that RNA-origami are taken up by HEK-293T cells to trigger TLR3-signaling pathway, rather than mediated through cytoplasmic RNA sensors, i.e., MDA5/RIG. Interestingly, although the RNA-origami and polyIC displayed a comparable level of activation in TLR3-reporter line, much more potent activation of splenocytes was found by RNA-origami than polyIC (see FIG. 3 and FIG. 4). This finding suggests that antigen presenting cells present in the spleen can uptake RNA-origami for the activation of these immune cells.

Furthermore, the cytokine profiles were examined in mice receiving intraperitoneal injection of RNA origami or low molecular weight polyIC that is in the same size range as the present RNA-origami. Interestingly, it was found that the cytokine profile in RNA-origami mice showed high levels of IL12, chemokines, but low and moderate levels of TNFa and IL6, respectively (FIG. 12). PolyIC used in this example has low molecular weight, whereas the one used in Takeda's report likely are high molecular weight PolyIC, which is associated with high toxicity. (Takeda et al., A TLR3-Specific Adjuvant Relieves Innate Resistance to PD-L1 Blockade without Cytokine Toxicity in Tumor Vaccine Immunotherapy, Cell Rep. 2017 May 30; 19(9):1874-1887.) Nevertheless, the polyIC-LMW did not induce significant elevation of these cytokines, similar to the study reported by Zhou, Y., 2012. TLR3 activation efficiency by high or low molecular mass polyIC. Innate Immunity. 19:184-192, which shows that high molecular weight (HMW) PolyIC (also referred to as "PolyIC-HMW") is more potent in vivo than low molecular weight (LMW) polyIC (polyIC-LMW). In addition, PolyIC-HMW is usually used as vaccination adjuvants and its systemic application is associated with toxicity. Compared to the levels of TNFa and IL-6 shown in Takeda's study, the levels of these cytokines induced by RNA-origami are at the range of those induced by two ARNAX, i.e., have low toxicity. Thus, the present RNA-origami may function more like ARNAX. On the other hand, elevation of three chemokines, CXCL9, CXCL10 and CCL2 play important roles to recruit CD8-T and NK cells to mount anti-tumor immunity.

Figure 13A:
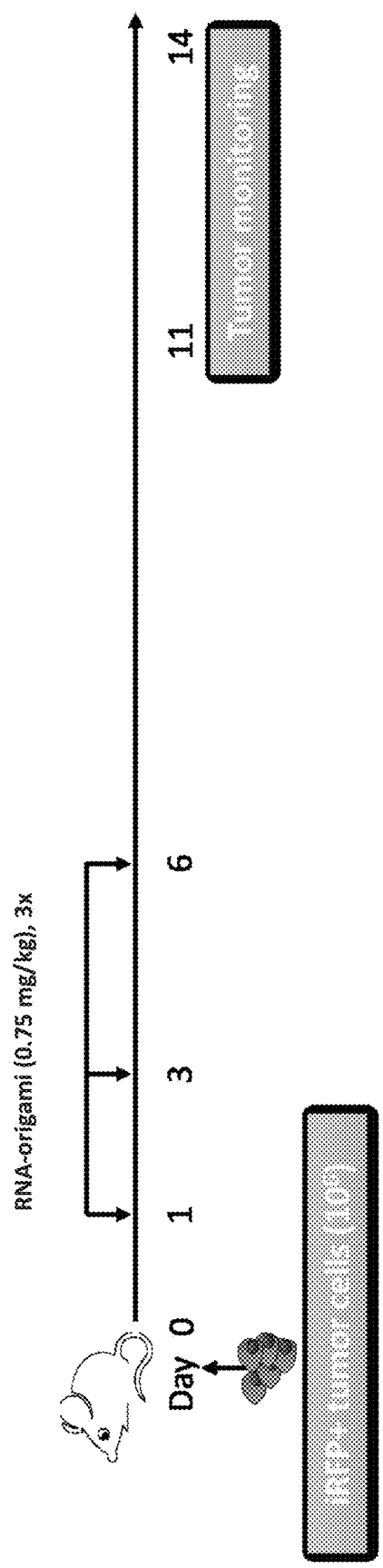
FIG. 13A shows the treatment and scheduling of mice with certain embodiments of the RNA nanostructures ("RNA-origami") described herein.
Figure 13C:
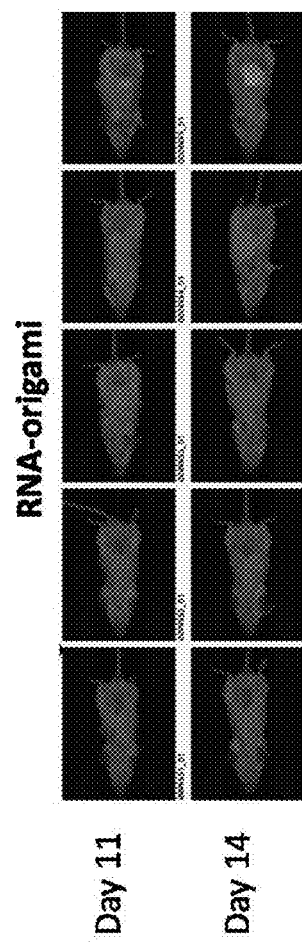
FIG. 13C shows inhibition of tumor growth in control after RNA-origami injection. Mice treated with RNA-origami show significant reduction in tumor growth.
Figure 13B:
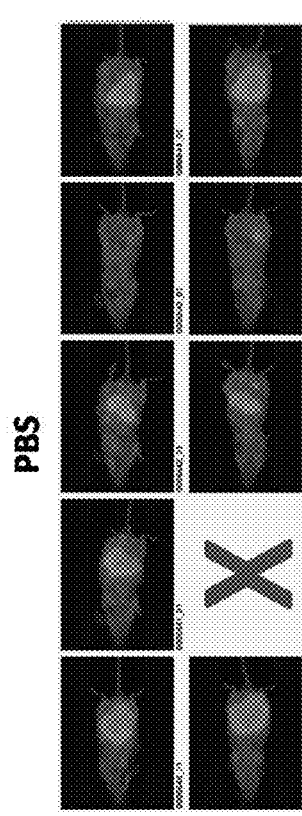
FIG. 13B shows lack of inhibition of tumor growth in control.
Figure 14:
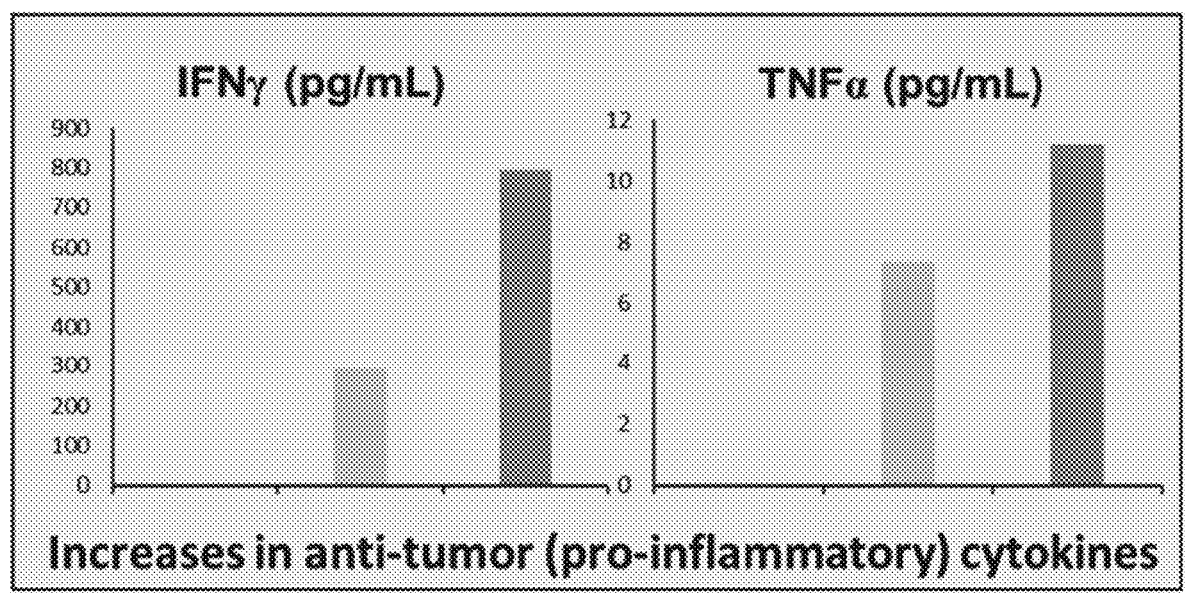
FIG. 14. RNA-origami increases pro-inflammatory cytokines and reduces anti-inflammatory cytokines. The high levels of IFNg and TNFa in the bearing-tumor bearing mouse treated with RNA-origami clearly showed strong induction of adaptive anti-tumor immunity. The left column (which is not visible in the Figure) is the biomarker levels in normal serum. The middle column is the biomarker levels of ascites fluid from tumor bearing mice. The right-most column is the biomarker levels of ascites fluid from RNA-origami treated tumor bearing mice. The results demonstrate that the RNA origami results in increases of anti-tumor (pro-inflammatory) cytokines.
Figure 15:
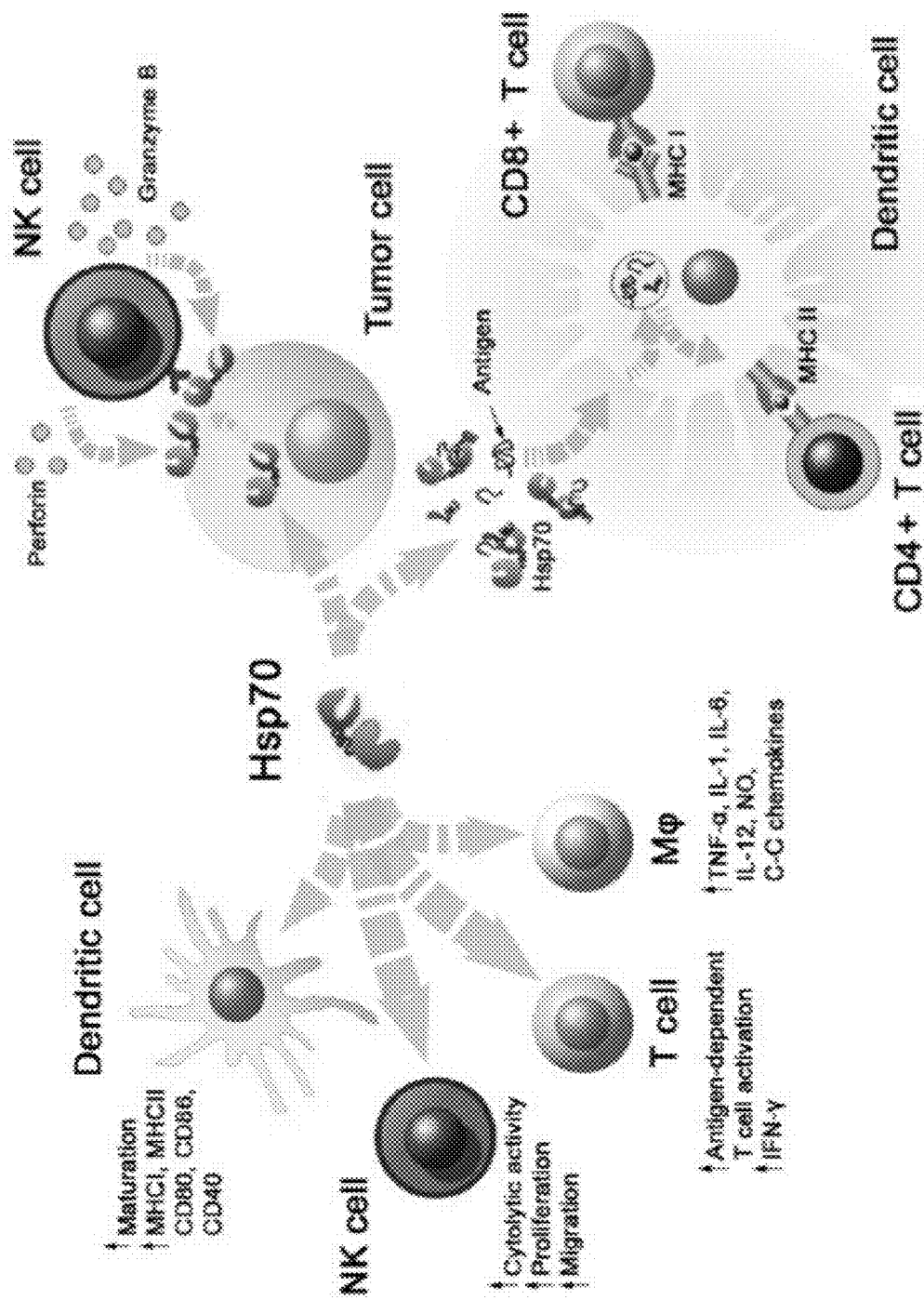
FIG. 15. Schematic of functions of HSP70 protein and derived peptides (also referred to as "TPP" or "TKD").

To determine whether the in vitro stimulation of immune cells can be translated into anti-cancer immune adjuvants, CT26 peritoneal colon carcinoma model was used, which has been explored as a peritoneal metastatic model, to test whether RNA-origami can reduce tumor growth in the peritoneal cavity. To monitor tumor growth in real time, a gene iRFP was introduced into CT26 cells, which codes for a near infrared fluorescence protein, such that the growth of tumor cells is measured by iRFP fluorescence intensity. A higher fluorescence intensity is indicative of a larger tumor mass. Specifically, on day 0, mice received one million CT26-iRFP cells via i.p. injection. The mice were treated with RNA-origami or control PBS on day 1, 3 and 7 at 16 microgram/dose, and tumor cells in peritoneal cavity was monitored by iRFP fluorescence intensity using LI-COR Pearl Small Animal Imaging System. It was found that while the mice injected with PBS developed tumor quickly (with 10-12 days), the mice treated with RNA-origami showed a significant reduction in tumor growth (FIG. 13). Thus, at a rather low doses used in the experiment, RNA-origami suppressed tumor growth. When the cytokines produced from ascites fluid that were accumulated within tumor cells present in the peritoneal cavity were analyzed, it was found that the ascites contained very high levels of immunosuppressive cytokines, including TGFb1, TGFb2, IL-10 and IL-4 (FIG. 14). In contrast, for the tumor-bearing mice treated with RNA-origami, they had much lower levels of immunosuppressive cytokines, but elevated levels of anti-tumor proinflammatory cytokines, which correlates with the small tumor load in the treated mice.

Example 3

Induction of Strong Anti-Tumor Immunity by RNA-Origami Complexed with Tumor Penetrating Peptide (TPP)

Nucleic acid based Toll-like receptor ligands, such as poly IC, ssRNA and CpG oligonucleotides are potent adjuvants via activation of TLR3, TLR7/8 and TLR9 signaling pathways, respectively. Tumor-specific antigens in combination with these TLR ligands have been explored as cancer vaccines to reduce tumor growth. Building on the finding of RNA origami as a TLR3 ligand discussed above, peptide-tagged RNA-origami complexes were constructed, and the complexes were shown to be stable and able to induce strong anti-tumor immunity.

Heat shock protein 70 (HSP70) is a cellular stress response protein, presumably protecting cells from toxic agents and harsh environment. On the other hand, because of its chaperon function in associated with tumor specific or tumor-associated antigens (TSAs or TAAs), HSP70 has also been explored as a TAA. It was reported to induce multi-faceted responses against cancer cells, including both innate and adaptive immunity. Interestingly, one peptide derived from the C-terminus of HSP70, also referred to as "TKD peptide", has been demonstrated (1) to activate NK cells, (2) to direct tumor-targeted binding and internalization, and (3) to promote DC cross-presentation and ultimately induction of cytotoxic T cell responses toward tumor cells. It was investigated whether the combination of this peptide with RNA-origami would constitute a potent cancer vaccine.

Given the potent and unique adjuvant activity of RNA-origami, it was hypothesized that complexing RNA-origami with TKD peptide would increase tumor-specific immunity. RNA-origami was complexed with tumor targeting peptide (TPP) TKD-peptide. TKD (TPP)-peptide has the sequence TKDNNLLGRFELSG (SEQ ID NO: 121) (C-terminal region of human HSP70), which is highly homologous to murine HSP70 sequence TRDNNLLGRFELSG (SEQ ID NO: 122).

To simplify the complex formation with RNA-origami, the TKD was modified by adding a cystine (C) at the N-terminus and adding 10 lysine residues to the C-terminus of the TKD peptide, thus creating CTKD-K10: CTKDNNLLGRFELSGGGSKKKKKKKKKK (SEQ ID NO: 3). The C residue allows peptide-dimerization to promote peptide binding to and clustering of HSP70 on the surface of tumor cells. Pre-incubation of CTKD-K10 with splenocytes can activate NK cells, which in turn kill tumor cells. CTKD-K10 can also bind to many tumor cells, also referred to as tumor penetrating peptide (TPP) and upon binding, it can induce internalization of the peptides, possibly via HSP70 oligomerization, reaching to endosome, lysosome and even mitochondria.

Figure 16:
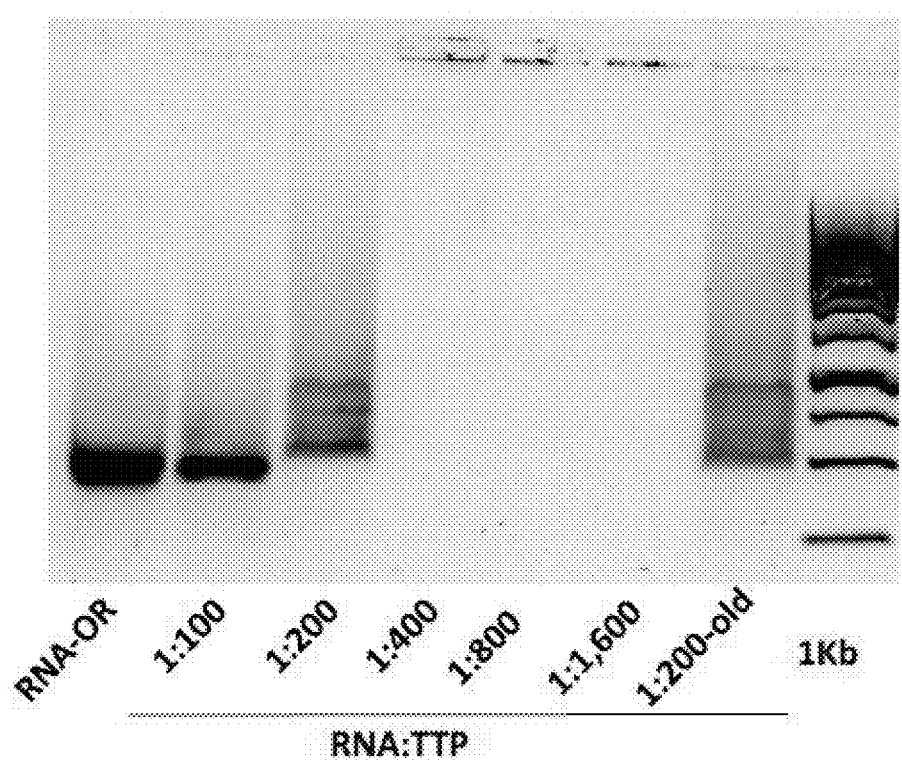
FIG. 16. Different RNA-OG/TTP ratios lead to different sizes of complexes. The complex appear stable after its formation as the old and new complexes formed at 1:200 (molar) ratios displayed similar pattern of mobility (lane 3 and lane 7).

RNA-origami are negatively charged structure, so the positive charge of polylysine on the TKD-K peptides enables direct, non-covalent complex formation with the RNA-origami. The complex was demonstrated formation by gel electrophoresis (FIG. 16). Depending on the RNA: peptide ratios, the size of the complexes is increased and some become aggregated. Different RNA-OG/TTP ratios lead to different sizes of complexes. The complex appears stable after its formation as the old and new complexes formed at 1:200 ratios displayed similar pattern of mobility (FIG. 16, lane 3 and lane 7).

Figure 17:
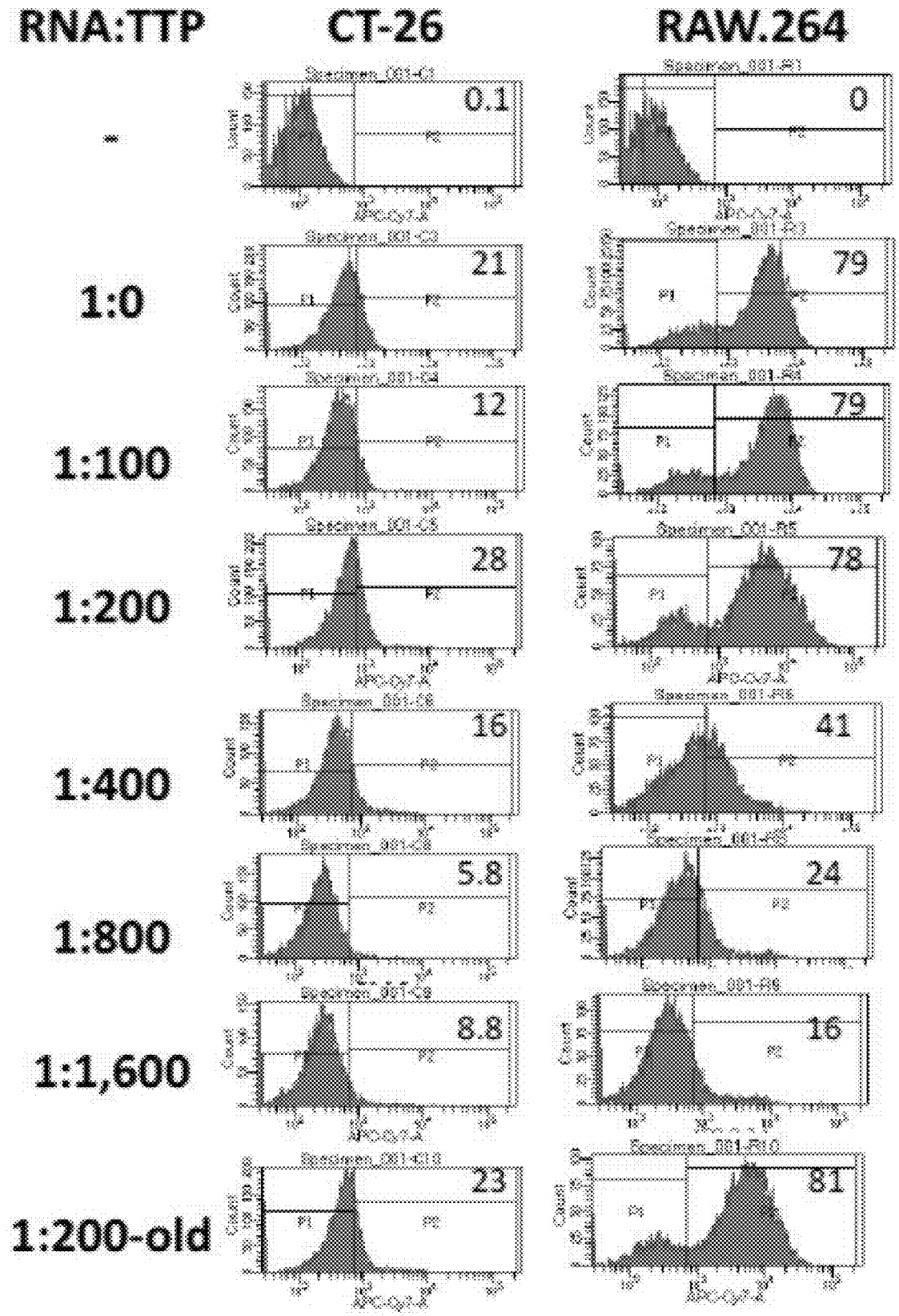
FIG. 17. Different complexes exhibit different binding/internalization profiles, as shown by flow cytometry. Higher internalization of RNA-origami (OG) by RAW cells than CT-26. Upon increase amount of the peptide, the lower level of binding to both CT-26 and RAW cells.

Different complexes exhibit different binding/internalization profiles, as shown by flow cytometry (FIG. 17). It was observed that the internalization of RNA-peptide complex is hindered if more peptides associated with the RNA. It was found that at RNA:peptide ratio of 1:100 or 1:200, the complex size was slightly shifted up, but is still taken up by both CT-26 colon cancer cell line and RAW-264 macrophage line (FIG. 17). Higher internalization of RNA-origami (OG) by RAW cells than CT-26. Upon increase amount of the peptide, the lower level of binding to both CT-26 and RAW cells. It was predicted that the combination of the RNA-origami and TKD peptide would further enhance and integrate TLR3 activation, NK-activation, antigen-cross presentation for effective induction of cytotoxic T cell responses.

Figure 18:
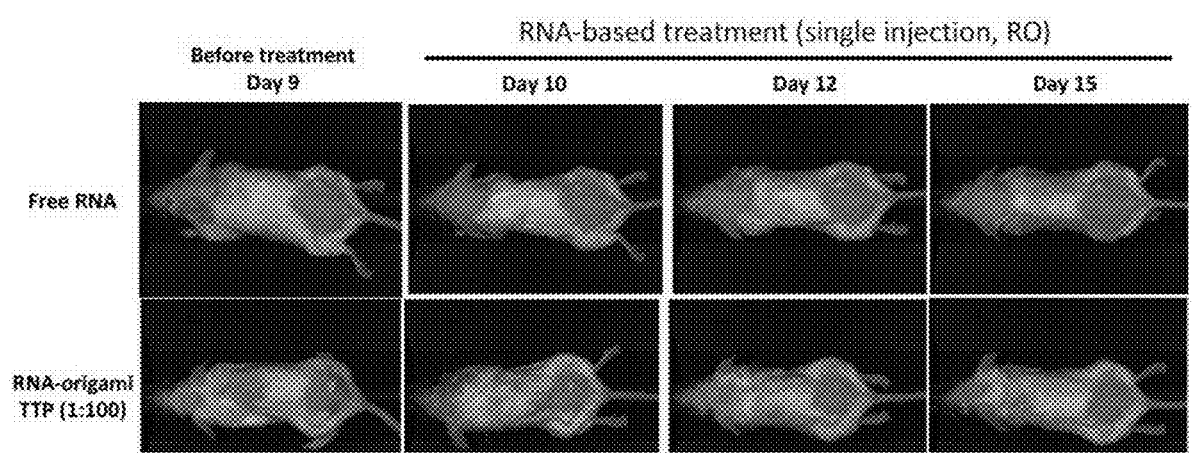
FIG. 18. Red-fluorescence positive tumor cells were inoculated at day 0 and tumor nodule formed on day 9 (i.e., pretreatment). These mice were then treated with a single injection of different types of RNA structures, free RNA or RNA-origami coated with tumor-targeting peptide (TTP). The mice were monitored for more than 20 days, and tumor regression was found in the mouse receiving the RNA-Origami polymer, but not other groups (including RNA-origami only group).

In an in vivo tumor model, the RNA-peptide complex was tested at the 1:100 ratio. Interestingly, a single injection of this complex into a mouse-bearing tumor led to complete tumor regression (FIG. 18). Red-fluorescence positive tumor cells were inoculated at day 0 and tumor nodule formed on day 9 (i.e., pre-treatment). These mice were then treated with a single injection of different types of RNA structures, free RNA or RNA-origami coated with tumor-targeting peptide (TTP). The mice were monitored for more than 20 days, and tumor regression was found in the mouse receiving the RNA-Origami polymer, but not other groups (including RNA-origami only group).

In a separate experiment, RNA-peptide complex (1:200 ratio) were also injected intraperitoneally, where the intraperitoneal colon tumor cells were inoculated (FIG. 19A). One RNA-OG/TPP and RNA-origami (OG) out of five treated mice showed tumor regression, whereas all the control groups, including the mice receiving free RNA, succumbed to tumor growth. The adaptive immunity of splenocytes recovered from the tumor-free mouse treated with RNA-OG/TPP were further tested and it was found that these cells are reactivated in vitro by the co-culture with TPP, but not when administered irrelevant KLH peptides (FIG. 19B-FIG. 19C). Thus, tumor-targeted adaptive immunity was elicited by the RNA-OG-TPP complexes.

Example 4

Incorporation of Modified Ribonucleotides into Transcribed ssRNA Sequence

The same RNA strand synthesis procedure as above was performed but a modified ribonucleotide was added during the in vitro transcription reaction. The 5-Aminoallyluridine-5'-Triphosphate (AA-UTP) is commercially available and is a good substrate for RNA polymerases to easily incorporate into RNA strand. The ratio of AA-UTP to UTP (non-modified ribonucleotides) was varied from 1:10 to 1:50, which generated 2-10% AA-UTP incorporation into the RNA strand, respectively.

The amine group in the resulting synthesized RNA strand is capable of conjugatation with peptides or antibodies through a bifunctional compound (e.g., SMCC crosslinker or sulfo-SMCC). When the total length of the ssRNA strand is 1000 bp, about 20 to about 100 AA-UTP are incorporated, representing potentially about 20 to about 100 conjugation sites.

Example 5

Stability of Peptide-ssRNA Complexes ($NR_1$—$R_3$, Wherein $R_3$ is a Peptide) ("RNA-OG")

The ssRNA from Example 1 was synthesized. Two different peptides ("Pep-1" and "Pep-2") that each comprise an additional 10 lysine residues were added to a solution of the rectangular sheet scaffold formed from folded ssRNA in 1×PBS buffer and allowed to form the complex formation between peptide and the RNA-OG. Similar complexes were constructed using the non-foldable polyIC chain. The peptides were added at molar ratios of (none), 1:100 (ssRNA: peptide), and 1:200 (ssRNA peptide). The RNA-OG or polyIC along with their peptide complexes were run on non-denaturing agarose gel electrophoresis. The left-most lane represents no added peptide. The right-most lane is a 1 Kb marker. The results show that for the ssRNA:peptide complexes were soluble and stable in solution, and the total MW increased in a dose-dependent manner as the peptide amount was increased. The polyIC control, however, failed to exhibit any form of soluble or stable complex under the same conditions.

Example 6

Demonstration of pH Sensitivity of Linker

In certain embodiments, the linker is pH-sensitive. The RNA duplex linked to double nanobots can be responsive to an acidic environment for being dehybridized. RNA duplex stability is pH sensitive as a lower pH reduces the melting temperature of short RNA-duplexes. The double-nanorobot is incubated in an acid low pH cell culture condition (pH 6.8) used to mimic tumor microenvironment. RNA-duplexes that are stable under pH7.4, but labile at pH 6.8, are designed using the Tiamat software and are tested under such denaturing conditions. Factors affecting the pH sensitivity include the hybridization length, the GC content of the sequences, and the proximity of the GC content to the terminae of the hybridized sequence.

In a further experiment, serum that contains nucleases are added to the culture to facilitate the degradation of RNA-duplexes to dissociate the two RNA nanostructures whereas the RNA-cage or RNA-origami are likely resistant to the nuclease.

Example 7

Thrombin Loading and Release

To the prepared RNA nanostructure is further added a 20-fold molar excess of fasteners and a fivefold molar excess of targeting strands, including the AS1411 sequence. Thrombin molecules are loaded on the top or the bottom surface of RNA nanostructure scaffolds, wherein the scaffold is an origami sheet. After fastening of the rectangular sheet into a tube, the top surface is rolled inside the tube due to curvature driving forces. Thus, thrombin is loaded on the inside or the outside surface of origami tubes. Thrombin loaded inside tubes is protected and shielded before delivery to the target location in vivo, while uncaged thrombin is subject to degradation. The topography is assayed through a platelet aggregation assay. For the rectangular RNA scaffold sheet structures, the ssRNA strand and thrombin-loading strands are mixed in 1×TAE-Mg buffer. The mixtures are then placed on an Eppendorf thermal cycler with the program: rapid heating to 65° C., then cooling to 25° C. at a rate of 10 min/° C. for annealing. For a control rectangular sheet structures, ssRNA and thrombin-loading strands are mixed together and annealed. Thrombin-RNA conjugates are then mixed with the rectangular RNA nanostructure scaffold sheet or control nanostructure. The mixtures are heated to 45° C. and cooled to 25° C. at a rate of 10 min/° C. to facilitate annealing.

The resultant thrombin-rectangle-RNA nanostructure origami assemblies are purified using 100 kD centrifugal filters to remove excess thrombin-RNA nanostructure conjugates. After loading thrombin, a 20-fold molar excess of fastener strand polynucleic acids and a 5-fold molar excess of targeting strand polynucleic acids, are added to induce the formation of tube structures. To facilitate annealing, the mixture is heated to 37° C. and then cooled to 15° C. at a rate of 10 min/° C.

The thrombin-loaded rectangular and tubular RNA nanostructure origami nanostructures are applied to the platelet aggregation assay described herein. Additionally, thrombin-RNA nanostructure and control RNA nanostructure are pretreated with proteinase K for 15 min at room temperature to remove the thrombin molecules on the outside surface of the tubes. Next, the proteinase-treated nanostructures are degraded with 20 U/ml DNase I (Invitrogen, Carlsbad, Calif., USA) at 37° C. for 30 min to expose the thrombin molecules inside the tubes. The expected considerably low platelet aggregation using thrombin-loaded RNA nanostructure or RNA nanostructure controls without such treatment indicates that only a small amount of thrombin molecules are loaded onto the outside surface of the tubes. Aggregation results of tube structures are obtained after proteinase and DNase I treatment and further demonstrate potent platelet aggregation, reflecting the vast majority of thrombin are loaded inside the RNA nanostructure tubes. The results of these experiments are used to estimate the percentage of thrombin loaded on the inside and outside surfaces of the thrombin-loaded RNA nanostructures. These results will demonstrate that the thrombin molecules can be arranged inside the RNA nanostructure in a shielded state by design.

Example 8

Confirming the Functionality of the IFN-γ Lock

The IFN-based RNA cage efficacy in a model tumor environment is demonstrated.

Figure 38:
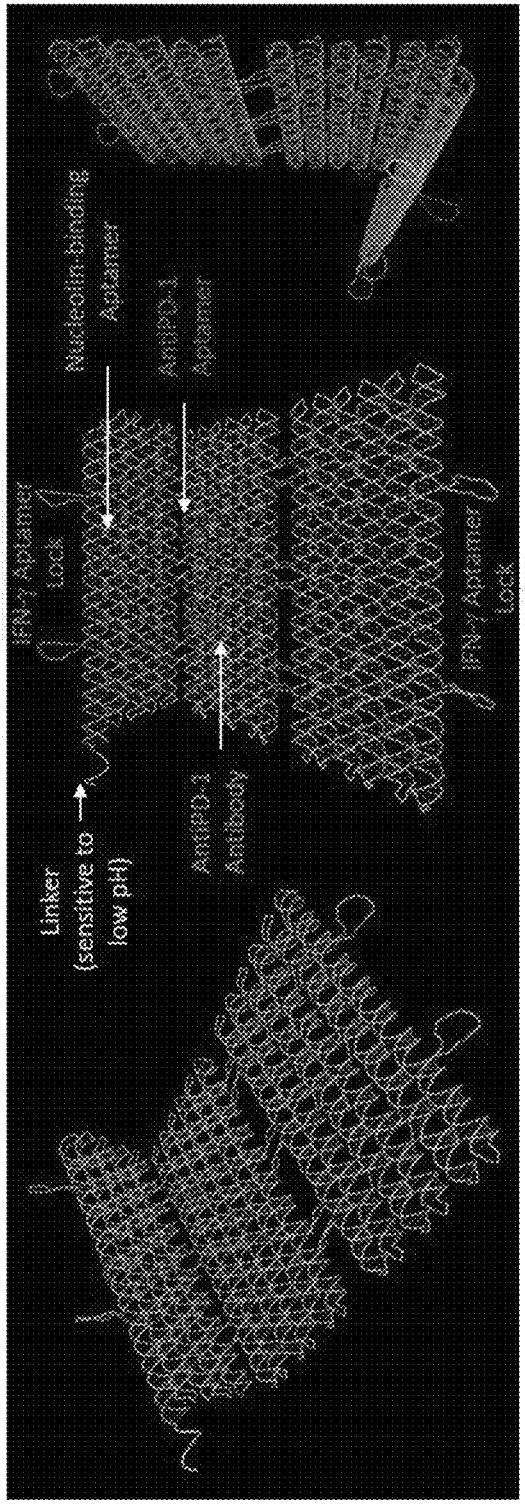
FIG. 38 depicts a molecular model of some embodiments of the ssRNA scaffold ("RNA cage") wherein the scaffold can fold into a tubular shape. The RNA cage can comprise IFN-γ aptamers, pH-sensitive linkers, anti-PD1 aptamers, anti-PD1 antibodies, and/or nucleolin-binding aptamers. The RNA cage can close in the presence of IFN-γ compounds whereby the IFN-γ aptamers located at the periphery of the RNA cage commonly bind to a single IFN-γ compound. In the presence of excess free IFN-γ compounds, the IFN-γ aptamers will each bind to the IFN-γ compounds, opening the cage to expose any moieties internal to the cage.
Figure 38:
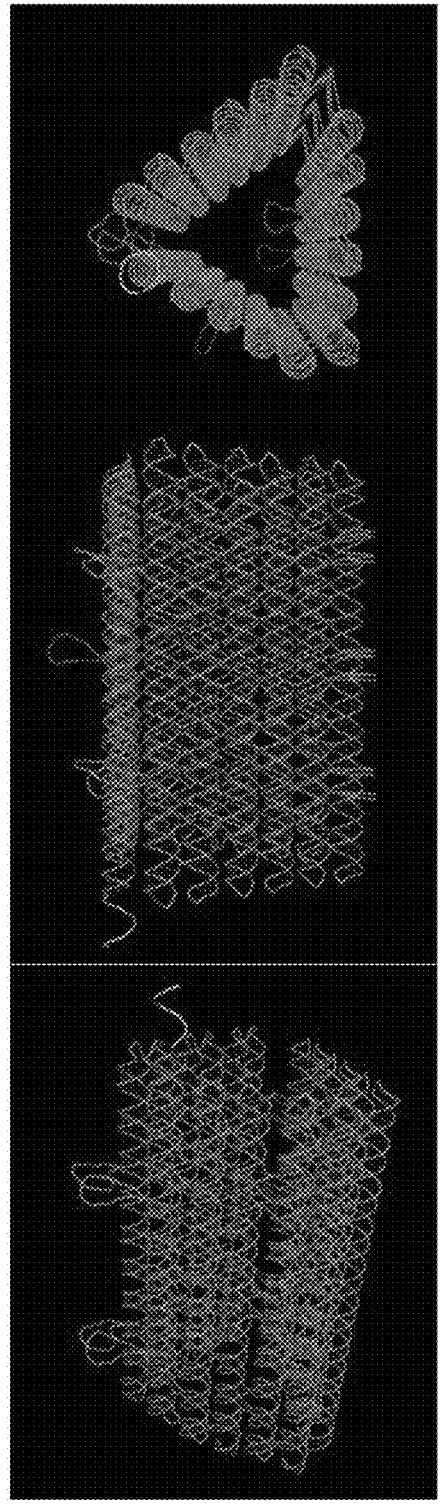

A RNA nanostructure comprising the sequence of SEQ ID NO: 9 is made by the methods described above. As shown in FIG. 38, the RNA nanostructure will exhibit a tube configuration in a closed RNA cage state when the IFN-γ lock is outside of a high-IFN concentration tumor environment. In some embodiments, high-IFN concentrations are greater than 5 μg/mL. The mixture is heated to 37° C., then cooled to 15° C. at a rate of 10 min/° C. to promote assembly. The RNA nanostructure further comprises an anti-PD1 antibody as a moiety internal to the enclosed RNA cage. The RNA nanostructure is linked with an IFN-γ-binding DNA aptamer with high binding affinity.

A 34-mer IFN-γ-binding aptamer sequence is used for the studies (IDT Technologies, San Diego, Calif.): 5'-NH2-C6GGGGTTGGTTGTGTTGGGTGTTGTGTCCAACCCC-C3-SH-3' (SEQ ID NO: 123). The aptamer is modified at the 5'-terminus with a C6-disulfide [HO(CH2)6-S-S-(CH2)6-] linker to bind the 5' terminus to a portion of the RNA nanostructure. In some embodiments, the unmodified aptamer sequence is extended with additional sequences to allow its assembly into the RNA nanostructure and lock the two ends of the RNA sheet.

The effector molecules entrapped within the RNA nanocage is an anti-PD1 antibody, anti-PDL-1 antibody, PD1-binding aptamers or PDL1-binding aptamers. The selected antibody will be conjugated to the amine-modified UTP designed to be positioned within the nanocage. Alternatively, the anchor sequences that are incorporated into the RNA-nanostructures are used to attach selected aptamers.

The RNA-nanocage is opened upon interaction with IFN-γ. For that, the assembled RNA-nanocage is incubated with various concentrations of IFN-γ and nonspecific protein control (IgG, BSA, etc.) and concentration dependent RNA nanocage opening is observed. The concentration of IFN-γ that opens the RNA nanocage is assessed by both gel electrophoresis and/or AFM. To further determine whether the enclosed effector molecules are accessible and function to bind their targets, a sandwich ELISA assay is used to detect the access of these molecules to the PD1 or PDL-1 coated to the ELISA plate and the molecules are detected by fluorescence-labeled PD1 or PDL1. For this test, the original RNA-nanocage in the absence of IFN-γ is included as a negative control since the antibodies or aptamers are kept inside the cage and not exposed. Once the cage is opened, effector molecules such as checkpoint inhibitor antagonists do not have to be released from RNA-nanostructures to antagonize checkpoint protein inhibitory pathways, because they can still function to bind and block the checkpoint molecules that are expressed on the cell surface of PD1+ or PDL-1+ cells.

Example 9

The Efficacy of RNA Double Robot Nanostructure

The RNA nanostructure of Examples 1 and 8 will be separately prepared and linked by cross-hybridization. The RNA-nanostructure of Example 1 ($NR_1$) stimulates splenocytes as demonstrated in Example 1, and the RNA-nanostructure of Example 8 ($NR_2$) is further linked with a anti-PD-1 antibody checkpoint inhibitor antagonist to demonstrate the blocking checkpoint effect. The PD1/PDL-1 bioassay kit (Promega, protocol attached) is used to assess the functional activity of the effector molecules (checkpoint inhibitor antagonists) that become accessible to the cells. The results demonstrate that upon presentation to a tumor cell, the RNA nanostructure of Example 8 in a closed cage open in the presence of localized high concentrations of IFN-γ to unlock the cage, thereby releasing active anti-PD1 antibody which blocks the checkpoint pathway.

Example 10

In Vivo Efficacy of RNA Double Robot Nanostructure

Additional experiments demonstrate this method works in vivo in the peritoneal tumor environment. To assess the in vivo efficacy of the nanorobots, nude mice bearing 100 mm$^3$ MDA-MB-231 tumors are randomly divided into six groups of eight mice per treatment group and are treated with saline, free thrombin, empty double nanorobot, nontargeted RNA nanostructure double robot comprising thrombin (free of target strands) made by the methods described herein, targeted RNA nanostructure comprising thrombin (comprising target strands), (1.5 U accumulated thrombin/mouse), by tail vein injection every 3 d for a total of six treatments. The day of the first injection is designated day 0. Tumors are measured with calipers in three dimensions.

The following formula is used to calculate tumor volume: Volume=(length×width$^2$)/2.

To confirm antitumor efficacy, a syngeneic B16-F10 melanoma tumor model is established by subcutaneous injection of 5×10$^6$ murine B16-F10 cells into the right posterior flank of C57BL/6J mice. When the tumors reach a size of 150 mm$^3$, the mice (ten mice per group) are treated intravenously with the cohort treatments as described above, every other day for 14 d. Tumor volume is determined as described above. The animals are euthanized after the last treatment, and the livers are excised and weighed. Liver sections are stained with H&E for metastasis analysis.

Two other tumor models, an ovarian cancer SK-OV3 xenograft model and an inducible KrasG12D lung tumor model are used to investigate the versatility of the thrombin-comprising RNA nanostructure double robot. For the SK-OV3 model, nude mice bearing 100 mm$^3$ SKOV3 xenografts (eight mice per group) are treated intravenously with the cohort treatments as described above, with an additional cohort treated with a scrambled aptamer control, periodically for a total of 6 treatments (~1.5 U accumulated thrombin/mouse). The inducible KrasG12D mice are fed with doxycycline diet since the 6$^{th}$ week after birth to induce primary lung adenomas. After being induced for 2 weeks, mice with tumors are randomly divided into four groups (three animals per group) and treated with the cohort treatments as described above by intravenous injection periodically. The progress of lung tumors is monitored by MR imaging 1 week and 2 weeks after treatment started. The results demonstrate the efficacy of the RNA nanostructure double robot comprising thrombin over the controls.

In Vivo MR Imaging.

TetO-KrasG12D transgenic mice are imaged using a 7.0 T Bruker Biospec animal MRI instrument (Germany). The imaging parameters are set as follows: FOV (field of view)= 3×3 cm$^2$, MTX (matrix size)=256×256, slice thickness=1 mm, TE=61.2 ms, TR=2320 ms, and NEX=4. The mice are anesthetized with 1.5% isoflurane delivered via nose cone before and during the imaging sessions.

Cell Viability Assay.

The cytotoxicity of the RNA nanorobot structure is assessed in murine endothelial bEnd3 cells. Cells (2,000 cells/well) are added to the wells of a 96-well plate (Corning, Woburn, Mass., USA). After culturing at 37° C. for 4 h, the cells are incubated with RNA nanorobot structure at either 3.3 nM or 6.6 nM (in PBS) for a further 24, 48 or 72 h. The proportion of viable cells is evaluated using a CCK-8 kit (Sigma-Aldrich, St. Louis, Mo., catalog No. 96992). Blank wells only with culture media and PBS-treated wells are used to define 0 and 100% viability, respectively.

Determination of Platelet Surface P-Selectin, Plasma Fibrin and Thrombin Levels and Platelet Counts.

Nude mice bearing MDA-MB-231 tumors are injected intravenously with the cohort treatments as described above periodically for a total of six injections. Mouse whole blood is then collected retro-orbitally into a 3.8% sodium citrate solution in blood collection tubes at the indicated time points. For platelet activity studies, the blood is mixed with an equal volume of 2% paraformaldehyde for 30 min at RT and centrifuged to obtain platelet-rich plasma (PRP). The PRP is incubated with FITC-conjugated P-selectin-specific monoclonal antibodies and analyzed by flow cytometry. Fibrin or thrombin levels in the PRP are quantified by enzyme-linked immunosorbent assay (ELISA) kits (Abcam, ab108844 and ab157527, respectively). Platelet numbers are counted manually with a hemocytometer using optical microscopy. The results demonstrate the efficacy of the RNA nanostructure double robot comprising thrombin over the controls.

Example 11

DNA Cage

Methods

The design and characterization of DNA half-cages and full-cages.

DNA origami half-cage and structures were designed with caDNAno, each used one M13mp18 ssDNA as the scaffold. Detailed design schemes are shown in FIGS. 7-9. One or both of the half-cages contained single-stranded probe strands (4 in each half-cage) extended toward the inside of the cage for binding with the DNA conjugated enzymes. Two of the half-cages can be linked together to form a fully enclosed full-cage though 24 linker strands. To form each of the half-cages, the M13mp18 ssDNA was mixed with the corresponding staples at a 1:10 molar ratio in 1×TAE-Mg2+ buffer (40 mM Tris, 20 mM acetic acid, 2 mM EDTA and 12.5 mM magnesium acetate, pH 8.0), annealed from 80° C. to 4° C. for 37 h. The excess staple strands were removed by the filtration of the DNA cages solution using 100-kD Amicon filter with 1×TAE-Mg2+ buffer for three times. To form a full-cage, 24 single-stranded DNA linkers were incubated with the two purified half-cages at a molar ratio of 5:1 for three hours at room temperature, in order to connect the two half-cages together.

Enzyme-DNA Cage Assembly.

A 15-fold molar excess of oligonucleotide-conjugated enzyme was incubated with the DNA half-cage containing capture strands. Protein assembly was performed using an annealing protocol in which the temperature was gradually decreased from 37° C. to 4° C. over 2 h and then held constant at 4° C. using an established procedure. Two Enzyme-attached half cages were then assembled into a full cage by adding DNA linkers as described above. The DNA caged-enzymes were further purified by agarose gel electrophoresis to remove excess free enzymes.

Preparation, Purification, and Characterization of Protein-DNA Conjugates.

Protein-DNA conjugation-SPDP conjugation chemistry was used to couple enzymes to oligonucleotides as reported previously. Enzymes (GOx, HRP, G6pDH, LDH, MDH and β-Gal) were first conjugated with SPDP at enzyme-to-SPDP ratios of 1:5, 1:20, 1:3, 1:5, 1:5, and 1:5, respectively, in HEPES buffer (50 mM HEPES, pH 8.5) for 1 h at room temperature. Different values of SPDP-to-Protein ratio were used due to the varied number of accessible surface lysine residues for each protein. Excess SPDP was removed by washing with 50 mM HEPES buffer using Amicon centrifugal filters (30 kD cutoff). The SPDP coupling efficiency was evaluated by monitoring the increase in absorbance at 343 nm due to the release of pyridine-2-thione (extinction coefficient: 8080 $M^{-1}$ $cm^{-1}$).

TCEP-treated thiolated DNA (/5ThioC6-/-TTTTTCCCTCCCTCC (SEQ ID NO: 126) (P), or/5ThioC6-D/-TTTTTGGCTGGCTGG (SEQ ID NO: 127) (P2) was incubated with the SPDP-modified enzymes at an enzyme-to-DNA ratio of 1:10 in 50 mM HEPES buffer (pH 7.4) for 1 h in the dark. Excess unreacted oligonucleotide was removed by ultrafiltration using Amicon 30 kD cutoff filters: washing one time with 50 mM HEPES (pH 7.4) containing 1 M NaCl and three times with 50 mM HEPES (pH 7.4). The high salt concentration in the first washing buffer helps remove DNA nonspecifically bound to the surface of the protein due to electrostatic interactions.

The absorbance values at 260 nm and 280 nm ($A_{260}$ and $A_{280}$) were recorded to quantify the enzyme-DNA complex concentrations and the labeling ratios using a Nanodrop spectrophotometer (Thermo Scientific). Extinction coefficients of DNA oligonucleotides were received from IDT-DNA, and extinction coefficients of enzymes were obtained from published data.

Enzyme-DNA Cage Assembly, Purification, and Characterization

The purified DNA half-cage containing capture strands was mixed with one of several enzyme-DNA conjugates at a 1:15 cage:enzyme ratio and annealed from 37° C. to 4° C. over 2 h in 1×TAE-$Mg^{2+}$ buffer (containing 12.5 mM Mg(OAc)2). Twenty-four single-stranded DNA linkers were mixed with the two purified half-cages at a 5:1 linker: cage ratio to connect the two half-cages together by incubating at room temperature for 3 h. Agarose gel electrophoresis (2%, 1×TAE-Mg21 was employed to remove excess free enzymes (70V, 2 h). The band of the DNA cage containing the enzyme was cut from the gel and extracted using a Freeze 'N Squeeze column (Bio-Rad). The DNA origami concentration was quantified by measuring the absorbance at 260 nm ($A_{260}$) using an extinction coefficient of 0.109 $nM^{-1}$ $cm^{-1}$.

The DNA cage sequences are those listed in U.S. patent application Ser. No. 15/649,351, herein incorporated by reference in its entirety.

Single-Molecule Fluorescence Microscopy.

All single-molecule measurements were performed at room temperature using a total internal reflection fluorescence (TIRF) microscope on PEGylated fused silica microscope slides. To passivate the microscope slides and functionalize the surface with biotin for selective immobilization of nanocages, a biotin- and PEG-coated surface was prepared by silylation with APTES, followed by incubation with a 1:10 mixture of biotin-PEG-SVA 5k:mPEG-SVA 5 k as described previously. A flow channel was constructed as described elsewhere. To prepare the surface for enzyme or nanocage binding, a solution of 0.2 mg/mL streptavidin in T50 buffer (50 mM Tris-HCl, pH 8.0, 50 mM NaCl, 1 mM EDTA) was injected in to the flow channel, incubated for 10 min, and the excess streptavidin was flushed out thoroughly first with T50, then with 1×TAE-Mg2+.

Yield estimation by TIRF colocalization: All single-molecule measurements were performed at room temperature using a total internal reflection fluorescence (TIRF) microscope on PEGylated fused silica microscope slides. To passivate the microscope slides and functionalize the surface with biotin for selective immobilization of nanocages, a biotin- and PEG-coated surface was prepared by silylation with APTES, followed by incubation with a 1:10 mixture of biotin-PEG-SVA 5k:mPEG-SVA 5k as described previously 3. A flow channel was constructed as described elsewhere 3. To prepare the surface for enzyme or nanocage binding, a solution of 0.2 mg/mL streptavidin in TSO buffer (50 mM Tris-HCl, pH 8.0, 50 mM NaCl, 1 mM EDTA) was injected in to the flow channel, incubated for 10 min, and the excess streptavidin was flushed out thoroughly first with TSO, then with 1×TAE-Mg.

The right half of the DNA origami cage was labeled with Cy5 dye inside the cavity, via hybridization of Cy5-labeled DNA to complementary handles incorporated into the structure. Each of the ssDNA conjugated enzymes (HRP, GOx, G6pD, LDH, MDH and β-Gal) was covalently labeled with Cy3 as described in section 3 (Cy3-Enzyme-5'-TTTTTCCCTCCCTCC, SEQ ID NO: 128), and then linked to the left half of the DNA origami cage via hybridization with complementary handles. Because Cy3 was directly labeled onto the enzyme surface, any observed Cy3 signal of the immobilized DNA nanocages came from the encapsulated enzymes. Linker strands were added to a 1:1 mixture of the two half-cages to encapsulate the enzymes in a full-cage. To capture DNA-modified enzymes in the absence of nanocage (as control) the microscope slide was incubated with 10-20 nM biotin-modified complementary DNA oligonucleotide (5'-biotin-TTTTTGGAGGGAGGG, SEQ ID NO: 129) for 3 min, followed by 10 min incubation with 20-50 μM enzyme sample in 1×TAE-Mg buffer. Excess enzyme was flushed out with 400 uL buffer (channel volume 30 μL). For the nanocage experiments, the samples were diluted to 20-50 μM in 1×TAE-Mg and immobilized on the streptavidin-coated PEG surface for 1 min, and the excess sample was flushed out with 400 μL of 1×TAE-Mg. The DNA-modified enzymes were imaged with illumination at 532 nm (15 W/cm2), and the nanocage-encapsulated enzymes were imaged with simultaneous illumination at both 532 nm (15 W/cm2) and 640 nm (40 W/cm2) as described. Particle-finding and colocalization analysis were performed using custom-written scripts in IDL and MAT-LAB, using a threshold of 150 counts per frame for particle identification (typical particles showed 500-1,000 counts per frame in each detection channel). The enzyme encapsulation yield, defined as the fraction of assembled nanocages containing enzyme(s), was estimated by dividing Ncaloc by the total number of particles containing a right half-cage, Nright.

Estimation of enzyme copy number per nanocage: The number of enzyme copies per nanocage (Nenz) was determined by single-molecule photobleaching (SMPB). First, the number of Cy3 photobleaching steps was determined separately for unencapsulated as well as half-cage and full-cage-encapsulated enzymes. For this, the donor channel data of all single molecules were idealized in QuB (http://www.qub.buffalo.edu) using a six-state model. The histogram of the photobleaching steps was then acquired using a custom-written MATLAB script. Finally, the number of enzyme molecules per cage was estimated by dividing the mean number of Cy3 photobleaching steps of the full-cage ($\mu cy3\_Encap$) by the mean number of Cy3 photobleaching steps for the unencapsulated enzyme ($\mu cy3\_Unencap$). Results are summarized in Table 4.

Single-Molecule Enzymology

Single-molecule enzyme activity assay: Prior to single-molecule activity measurement, streptavidin-modified slides were incubated for 2 min with neutravidin-coated fluorescent beads (Invitrogen, 0.04 μm diameter, excitation/emission; 550/605 nm) at 106-fold dilution and the excess flushed out with 1×TBS buffer. These beads (5-8 per field of view) were used as fiducial markers to correct for drift of the microscope stage and/or slide. Following complete photobleaching of Cy3 in a field of view, the activity of single unencapsulated or nanocage-encapsulated enzyme molecules was imaged on the same field of view. During analysis of the movies, the coordinates of the initial photobleaching movie were registered with those of subsequent movies using the fiducial markers (visible throughout all sequential movies) in a custom-written MATLAB script. This approach allowed us to infer the locations (x- and y-coordinates) of all individual enzymes/nanocages in the field of view even after bleaching Cy3, and to monitor enzyme turnovers (resorufin formation) at these specific coordinates.

To image enzyme activity, 300 μL of substrate solution in 1×TBS buffer (pH 7.5, 1 mM Mg2+, and 10% (w/v) PEG8000) was injected into the flow channel. Movies were recorded for 5 min (9,091 frames) at 35 ms frame exposure time immediately after injecting the substrate solution. In case of G6pDH, the activity was measured in the same field of view under identical laser illumination and microscope settings, with or without glucose-6-phosphate (G6p). Enzyme activity for β-Gal was measured similarly using a 500 nM solution of resorufin β-D-galactopyranoside (RBG) as substrate, which is hydrolyzed by β-Gal into fluorescent resorufin. Fluorescence fluctuations over time were measured for unencapsulated enzyme as well as half- and full-cage-encapsulated enzyme, and the fluorescence time traces were analyzed for intensity spikes using custom-written MATLAB script. The script allowed us to measure the background intensity of single-molecule traces and set a threshold (mean+8 standard deviations) to subtract from the raw intensity. Since we often observed one or two spikes above this intensity threshold in the control experiments, only those molecules with 2:4 spikes were counted as active molecules and considered for burst analysis. Due to the low concentration of resazurin, the criteria we used to determine the fraction of active molecules might have excluded some molecules that are not highly active.

Burst analysis: Burst analysis was carried out using a modified Rank Surprise (RS) method6 recently utilized to analyze the binding of fluorescent DNA probes to a riboswitch. Briefly, Interspike Intervals (ISIs) were determined by calculating the time in between individual fluorescent spikes for each molecule. The RS method was used to demarcate the start and end points of bursts after collecting ISIs for all molecules. Only intensity spikes characterized by an ISIs of greater than 3 seconds were considered part of a burst; any other intensity spikes are counted as non-bursts.

Comparing bulk and single-molecule enzyme activity: Unlike our single-molecule assay, the bulk measurement of enzyme activity cannot explicitly determine the fraction of active enzyme molecules present in the solution (it is well known that a fraction of enzyme molecules loses their activity during oligonucleotide conjugation, buffer exchange and the purification process). However, the observed bulk activity is contributed not only by enzyme turnover rate but also by the fraction of enzyme molecules that are still active. Both of these contributing factors need to be accounted for to directly compare the single-molecule enzyme activity with the bulk measurements. Therefore, in the single-molecule experiment, the overall activity of free, half-cage and full-cage enzymes were calculated by multiplying the turnover rate with the fraction of active molecules for the given sample.

Bulk Solution Enzyme Assay.

A 96-well-plate reader was used to monitor enzyme activity through absorbance changes of the samples. The enzyme samples and substrates were loaded in the wells of the 96-well plate with a final concentration of caged enzymes 0.5 nM in 1×TBS (Tris buffered saline with 1 mM MgCl2, pH 7.5) for most assays.

Enzymes and Substrates:

Glucose-6-phosphate dehydrogenase (G6pDH, *Leuconostoc mesenteroides*), malic dehydrogenase (MDH, porcine heart), lactate dehydrogenase (LDH, rabbit muscle), glucose oxidase (GOx, *Aspergillus niger*), horseradish peroxidase (HRP) and P-galactosidase (β-Gal, *E. coli*) were purchased from Sigma (St. Louis, Mo.). Pyruvate, oxaloacetate (OAA), glucose 6-phosphate (G6P), glucose, resorufin 3-D-glucopyranoside (RBG), β-nicotinamide adenine dinucleotide (NAD), resazurin (RESA) and phenazine methosulfate (PMS) were obtained from Sigma-Aldrich. ABTS (2,2'-Azino-bis[3-ethylbenzothiazoline-6-sulfonic acid] diammonium salt) was purchased from Pierce (Rockford, Ill.), polyphosphate (100) is ordered from Kerafast.

DNA Strands:

Single-stranded MI3mp18 DNA was purchased from New England Biolabs. Staple strand oligonucleotides were obtained from Integrated DNA Technologies (IDT) on 96-well plates and used without further purification. Thiol-modified DNA oligonucleotides were also purchased from IDT, and were purified by denaturing PAGE before use.

Reagents:

N-Succinimidyl 3-(2-pyridyldithio)propionate (SPDP) and tris(2-carboxyethyl)phosphine (TCEP) were obtained from Pierce. Dimethyl sulfoxide (DMSO) was purchased from Sigma.

Buffers:

Phosphate buffered saline (PBS), HEPES sodium salt, Tris buffered saline (TBS), Tris base, acetic acid, EDTA, and magnesium acetate were purchased from Sigma. 1×TAE/Mg2+ buffer (pH 8.0) is prepared by 40 mM Tris, 20 mM acetic acid, 2 mM EDTA and 12.5 mM magnesium acetate.

Dye-Labeling Reagents:

NHS-Cy3, Cy5 amine reactive dyes were purchased from GE Healthcare Life Sciences. NHS-AlexaFluor®555 and AlexaFluor®647 amine reactive dyes were obtained from Life Technologies.

Amicon centrifugal filters were purchased from Millipore. PEG 8000 was purchased from Promega.

Surface PEGylating Reagents:

APTES (3-Aminopropyl)triethoxysilane was purchased from Sigma-Aldrich. mPEG-SVA 5 k and biotin-PEG-SYA 5 k were obtained from Laysan Bio, Inc.

Tem Imaging:

TEM grids (400 mesh, copper grid coated with ultrathin carbon, Ted Pella) were glow discharged (Emitech Kl OOX). 2 μl concentrated samples were deposited onto the grids for 1 min, washed with 10 μl DI water for 5 sec, stained with 10 μl 1% uranyl formate twice (2 sec for the first time and 15 sec for the second time), and imaged using Philips CMI2 transmission electron microscope.

Enzyme Activity Assay:

A 96-well-plate reader was used to monitor enzyme activity through absorbance changes of the samples. The enzyme samples and substrates were loaded in the wells of the 96-well plate with a final concentration of caged enzymes of 0.5 nM in 1×TBS (Tris buffered saline with 1 mM MgCl2, pH 7.5) for most assays. The DNA cage concentration was determined by the A260 value as described above. For a typical GOx and HRP assay, 1 mM Glucose and 2 mM ABTS was used as substrate and enzyme activity was measured by monitoring the increase in absorbance at 410 nm (ABTs-1). For a typical G6pDH assay, 1 mM G6P and 1 mM NAD+ were used as substrates, and enzyme activity was measured by monitoring the increased absorbance at 340 nm due to the reduction of NAD+ to NADH. For a typical LDH assay, 2 mM pyruvate and 1 mM NADH were used as substrates, and enzyme activity was measured by monitoring the decreased absorbance at 340 nm due to the oxidation of NADH to NAD+. For a typical MDH assay, 2 mM OAA and 1 mM NADH were used as substrates, and enzyme activity was measured by monitoring the decrease in absorbance at 340 nm. For a typical 3-Gal assay, 100 μM RBG was used as substrate and enzyme activity was measured by monitoring fluorescence intensity, with excitation at 532 nm and emission at 590 nm.

Trypsin Assay:

Enzyme activity was measured after incubation with or without trypsin (1 μM) at 37° C. for 24 h in 1×TAE-10 mM Mg buffer (pH 8.0). Activity assay conditions: 1 mM Glucose, 1 mM ABTS, 1 nM of free GOx and HRP in pH 7.5, 1×TBS buffer containing 1 mM MgCl2, and monitoring absorbance at 410 nm. In the DNA cage experiment, all conditions were the same except for incubating 1 nM DNA cage-encapsulated GOx and HRP with trypsin.

Results

Enzyme Encapsulation Strategy.

The current embodiment of the approach for enzyme encapsulation within DNA nanocages involves two steps: 1) the attachment of an individual enzyme into an open half-cage and 2) the assembly of two half-cages into a full (closed) nanocage. DNA half-cages were constructed by folding a full-length M13 viral DNA29 into the indicated shape based on a honeycomb lattice using the DNA origami technique; a shape with two open sides was chosen to improve accessibility of the internal cavity to large proteins. Two half-cages were then linked into a full-cage by adding 24 short bridge DNA strands that hybridize with the complementary ssDNA sequences extending from the edges of either half-cage. The DNA full-cage is 54 nm×27 nm×26 nm with designed inner cavity dimensions of 20 nm×20 nm×17 nm. By design, 42 small nanopores (each 2.5 nm in diameter) were introduced on each of the top and bottom surfaces of the DNA nanocage to permit the diffusion of small molecules (e.g., enzyme substrates) across the DNA walls.

The formation of half and full DNA nanocages was first characterized using transmission electron microscopy (TEM) and gel electrophoresis, which indicate a nearly 100% yield for half-cages and a more than 90% yield for full-cages. To capture target enzymes into a half-cage, a previously reported succinimidyl 3-(2-pyridyldithio) propionate (SPDP) chemistry was used to crosslink a lysine residue on the protein surface to a thiol-modified oligonucleotide. Two anchor probes of complementary sequence were displayed on the bottom of the half-cage cavity to capture a DNA-modified enzyme via sequence-specific DNA hybridization.

As a demonstration of an enzyme cascade, a glucose oxidase (GOx)-attached half-cage was incubated with a horseradish peroxidase (HRP)-attached half-cage at a stoichiometric ratio of 1:1, followed by the addition of bridge strands into solution to assemble a full DNA nanocage containing a GOx/HRP pair. The inner cavity of a full nanocage is of sufficient size to encapsulate this enzyme pair (GOx is 10 nm32 and HRP 5 nm in diameter33). Unencapsulated enzyme and excess short DNA strands were removed using agarose gel electrophoresis (AGE). Details of the enzyme-DNA conjugation and optimization of the assembly.

Characterization of Enzyme Encapsulation.

To verify the presence of both enzymes within a DNA nanocage, the co-localization of a Cy3-labeled GOx (green emission) and a Cy5-labeled HRP (red emission) was quantified by dual-color fluorescence gel electrophoresis where a gel band with overlapped green and red color was identified. By comparison, the GOx-containing half-cage (Half[GOx]) shows the presence of only Cy3 (green), whereas a HRP-half-cage (Half[HRP]) shows the presence of only Cy5 (red). In addition, negatively-stained TEM images were used to visualize DNA cages upon stoichiometrically controlled encapsulation of a single GOx or a single GOx/HRP pair, where GOx and HRP were visible as brighter spots within the cage. To quantitatively analyze the yield of DNA nanocage encapsulation, two-color total internal reflection fluorescence (TIRF) microscopy34 was used to characterize the fluorescence co-localization of a Cy3-labeled enzyme and a Cy5-labeled nanocage. Six different enzymes were tested and characterized for encapsulation, ranging from the smallest HRP (44 kD)35, malic dehydrogenase (MDH, 70 kD)36, glucose-6-phosphate dehydrogenase (G6pDH, 100 kD)37, lactic dehydrogenase (LDH, 140 kD)38 and GOx (160 kD)39 to the largest P-galactosidase (β-Gal, 450 kD)40. All six enzymes were successfully encapsulated within full DNA nanocages with high yields, ranging from 64-98%. The relatively low yield of β-Gal (64%) may be due to its large size (16 nm in diameter), which is comparable to the inner diameter of the nanocage (20 nm), likely resulting in steric hindrance for encapsulation. To evaluate how many copies of the same enzyme were encapsulated per DNA nanocage, single-molecule fluorescence photobleaching (SMPB) was used to count the number of photobleaching of Cy3 fluorophores per cage. The number of copies of each enzyme per cage was estimated by normalizing the number of Cy3 fluorophores per DNA nanocage with the average number of Cy3 labels per free enzyme. A majority of nanocage-encapsulated enzymes showed only one- or two-step photobleaching of Cy3, similar to the photobleaching of single free enzymes. These results suggest that most nanocages (90%) contain exactly one enzyme per cage, as expected (Table 3).

TABLE 3

Calculation of enzyme copies per DNA nanocage. The percentage of molecules exhibiting a given number Cy3 photobleaching steps "Cy3 Steps" for both the encapsulated and unencapsulated enzymes are provided. The mean number of enzymes per cage ($N_{enz}$) was calculated by taking the ratio of $\mu_{Cy3\_Encap}$ to $\mu_{Cy3\_Unencap}$. N is the total number of particles analyzed.

|  | N | Cy3 Steps (% molecules) | | | $\mu_{Cy3\_Encap}$ | Cy3 Steps (% molecules) | | | $\mu_{Cy3\_Unencap}$ | $N_{enz}$ |
|---|---|---|---|---|---|---|---|---|---|---|
|  |  | One | Two | Three |  | One | Two | Three |  |  |
| HRP | 176 | 86 | 13 | 1 | 1.15 | 92 | 8 | 0 | 1.08 | 1.0 |
| G6pDH | 218 | 87 | 10 | 3 | 1.16 | 93 | 7 | 0 | 1.07 | 1.1 |
| β-Gal | 284 | 93 | 6 | 1 | 1.08 | 88 | 9 | 3 | 1.15 | 0.9 |

Conditions for the single-molecule enzyme activity assay were as follows:

| Solution | Concentration |
|---|---|
| 10X TBS, pH 7.5 | 1X |
| Resazurin Glucose-6-phosphate (G6p) | 50 nM |
|  | 1 nM |
| Phenazine Methosulfate (PMS) | 12.5 μM |
| $Mg^{2+}$ ($MgCl_2$) | 1 mM |
| $NAD^+$ | 1 mM |
| PEG 8000 | 10% (w/v) |

Activity Characterization of Nano-Caged Enzymes.

To evaluate the effect of DNA nanocages on enzyme activity, an encapsulated GOx/HRP pair was tested. This pair of enzymes catalyzes a reaction cascade beginning with the oxidation of glucose by GOx to generate hydrogen peroxide ($H_2O_2$). $H_2O_2$ is subsequently used by HRP to oxidize ABTS, producing a strong colorimetric signal. The overall activity of a co-assembled GOx/HRP cage (Full [GOx/HRP]) is 8-fold higher than that of a control enzyme pair incubated with the same cage but without encapsulation. Two plausible effects are hypothesized which could contribute to such a significant activity enhancement: 1) The proximity effect that brings the two enzymes close together and facilitates their substrate transfer, as described previously; and/or 2) the unique environment provided by the high charge density of DNA helices within a nanocage.

To separate the proximity effect from the charge density effect, control experiments of DNA nanocages encapsulating only a single GOx or HRP enzyme are designed, which clearly do not allow for substrate channeling between two proximal enzymes. For example, an equimolar mixture of two separate nanocages encapsulating either a single GOx or a single HRP (Full[GOx]+Full[HRP]) exhibited an 4-fold increase in overall activity compared to the unencapsulated control enzymes. Similarly, an equimolar mixture of two half-cages encapsulating either a single GOx or a single HRP already showed an increase in overall activity by 3-fold. Since there was no proximity effect in the case of two enzymes encapsulated into two different nanocages, the local environment modified by a DNA nanocage appears to be more important for the observed activity enhancement. Similarly, a half-cage was almost as effective in activity enhancement (3-fold) as a full-cage, suggesting that enzyme access to substrate does not play a role in this enhancement. Interestingly, a similar enhancement was reported previously upon conjugation of enzymes to a giant multi-branched DNA scaffold, without further explanation.

To test the generality of nanocage activity observations, the activity of six different enzymes upon encapsulation within DNA nanocages are evaluated. As shown in Table 4, five of them (GOx, HRP, G6pDH, MDH, and LDH) exhibited higher activity in nanocages than the free enzyme, with enhancements ranging from 3- to 10-fold.

TABLE 4

Enzyme kinetic data (values of $K_M$ and $k_{cat}$) for each individual enzyme encapsulated inside a DNA full-cage in comparison with the values for the free enzymes in solution.

| Enzyme | pI | Molecular weight | Substrate | Free enzyme | | Encapsulated enzyme | |
|---|---|---|---|---|---|---|---|
|  |  |  |  | $K_M$ (μM) | $k_{cat}$ (s-1) | $K_M$ (μM) | $k_{cat}$ (s-1) |
| GOx | 4.2 | 160 kDa | Glucose | 6,200 ± 900 | 240 ± 10 | 3,000 ± 600 | 1,300 ± 50 |
| HRP | 8.8 | 44 kDa | $H_2O_2$ | 2.3 ± 0.5 | 32 ± 1 | 4.3 ± 0.6 | 290 ± 5 |
|  |  |  | ABTS | 2,600 ± 400 | 59 ± 5 | 2,500 ± 200 | 560 ± 20 |
| G6pDH | 4.3 | 100 kDa | Glucose-6-phosphate | 220 ± 20 | 130 ± 3 | 310 ± 30 | 460 ± 10 |
|  |  |  | NAD+ | 510 ± 50 | 100 ± 3 | 590 ± 40 | 480 ± 10 |
| MDH | 10.0 | 70 kDa | NADH | 180 ± 50 | 51 ± 5 | 270 ± 50 | 460 ± 30 |
| LDH | 5.0 | 140 kDa | NADH | 7.2 ± 1.3 | 46 ± 2 | 17.0 ± 1.5 | 190 ± 5 |
| β-Gal | 4.1 | 465 kDa | RBG | 58.7 ± 16.0 | 8.5 ± 0.6* | 95.5 ± 18.9 | 1.6 ± 0.1* |

ABTS, 2,2'-azino-bis(3-ethylbenzothiazoline-6-sulphonic acid);
GOx, glucose oxidase;
HRP, horseradish peroxidase;
LDH, lactic acid dehydrogenase;
MDH, malic dehydrogenase;
pI isoelectric point. The pI values of the enzymes were obtained from brenda-enzymes.org
*$k_{cat}$ values for β-Gal groups were not calibrated Detailed kinetic analyses show that the KM (the Michaelis-Menten constant) varies little between encapsulated and free enzyme for most substrates (ranging from 0.5 to 2.4-fold of the free enzyme), suggesting that the porous DNA cages do not substantially hinder diffusion of small-molecule substrates. In contrast, a large increase in turnover number (kcat) was observed for these five enzymes (ranging from 3.5- to 9.6-fold of the free enzyme), suggesting an inherently higher catalytic activity of the proteins. An inverse correlation was observed between enhanced turnover and size of the encapsulated enzyme. That is, the smaller HRP (44 kD) and MDH (70 kD) exhibited relatively large increases in turnover number of 9.6±0.4 and 9.0±0.7 fold, respectively, whereas the larger enzymes G6pDH, LDH, and GOx exhibited smaller enhancements of 4.7±0.1 fold, 4.1±0.1 fold, and 5.4±0.2 fold, respectively. No correlation was observed between enhancement and isoelectric point (pI), despite the wide range of pI values for these enzymes (ranging from 4.2 to 10.0).

In contrast to these five enzymes, 3-Gal is strongly inhibited upon encapsulation, possibly due to its large size (16 nm in diameter) that is comparable to the inner cavity diameter (20 nm) of the DNA nanocage. Alternatively, the 3-Gal orientation may be unfavorable and block binding of substrate to the active site. Notably, in a control experiment polyphosphate inhibited the activity of β-Gal, suggesting that the local high density of backbone phosphates of the DNA nanocage might be responsible for the decrease in activity of 3-Gal. The DNA cages retained their structural integrity during the enzymatic reactions.

To gain more detailed mechanistic insight into the enhancement of catalytic turnover, a novel single-molecule fluorescence assay to characterize the activity of individual enzymes with and without encapsulation was applied. TIRF microscopy is used to record the repetitive turnover of substrates by individual G6pDH enzymes over time; coupling with a PMS/resazurin reaction allowed us to detect stochastic fluctuations of enzyme turnover rates via transient spikes in intensity from the generation of the fluorescent product resorufin. Such fluctuations have been observed for various enzymes before and are thought to be induced by the conformational switching between more and less active sub-states.

Compared to a control without substrate, more frequent fluorescent spikes were observed with the addition of glucose-6-phosphate substrate. The average spike frequency was increased from 0.016±0.001 s−1 for unencapsulated enzymes, to 0.019±0.001 s−1 for the half-cage and 0.026±0.002 s−1 for the full-cage. Further analysis suggested that the fraction of active enzyme molecules was increased from 20.3% for unencapsulated enzymes to 26.6% for the half-cage and 30.5% for the full-cage. Taken together, the 1.6-fold higher spike frequency and the 1.5-fold increase in the fraction of active enzymes yield a 2.5-fold increase in G6pDH activity for the encapsulated compared to the unencapsulated enzyme, comparable to the 4-fold enhancement observed in the bulk assay. Conversely, a similar analysis of β-Gal activity showed a 3-fold lower activity of the full-cage enzyme (2.3±0.5 fold lower in spike frequency compared to free enzyme whereas the fractions of active enzymes (65%) were similar) compared to unencapsulated enzyme, also consistent with the bulk measurement.

The activity enhancement for DNA cage-encapsulated enzymes is consistent with recent reports of enhanced enzyme activity upon attachment to a long double-stranded DNA molecule (DNA), a 2D rectangular DNA origami, or a DNA scaffold that bound to enzyme substrates, and further suggests that it may be a widespread effect of enzyme-DNA interactions. Several mechanisms have been previously proposed to explain these observed enhancements, including micro-environment composed of giant and ordered DNA molecules, molecular crowding and the substrates affinity to DNA scaffolds. We further suggested that the negatively charged phosphate backbones of DNA might also contribute to the activity enhancement. DNA is a negatively charged biopolymer due to its closely spaced backbone phosphates (leading to a linear negative charge density of 0.6 e/A). Thus, upon encapsulation within a DNA nanocage, an enzyme is exposed to an environment full of negative charges that may resemble the relative abundance of polyanionic molecules and surfaces (including RNA and phospholipid membranes) within the cell. Phosphate is a known kosmotropic anion that increases the extent of hydrogen-bonded water structures (termed high-density or structured water). A DNA nanocage is thus expected to attract a strongly bound hydration layer of hydrogen-bonded water molecules inside its cavity. Multiple studies have described that proteins are more stable and active in a highly ordered, hydrogen-bonded water environment, possibly due to stabilization of the hydrophobic interactions of a folded protein through an increase in the solvent entropy penalty upon unfolding.

Consistent with this model, polyphosphate has been shown to act as a generic chaperone stabilizing a variety of enzymes. To further test whether this mechanism is at work in our nanocages, we titrated the concentration of NaCl (known to consist of chaotropic ions) for the purpose of interrupting hydrogen-bonded water molecules. Consistent with our hypothesis, the activity of encapsulated enzymes significantly decreased with increasing NaCl concentration (reduced to 25% activity with 1 M NaCl. A high concentration of Na+ can shield the negative charge on the DNA surface, thus disrupting the surface-bound hydration layer. As a control, we observed that the bulky kosmotropic cation, triethylammonium, had a much less pronounced effect on enzymatic activity. This model also allowed us to rationalize why we observed smaller enzymes to be more activated than larger enzymes: namely, because their higher surface-to-volume ratio predicts a stronger impact of the hydration layer.

To further test this model, we investigated the effect of DNA helix density on the encapsulated enzyme activity. Three nanocages were designed with walls that systematically increase the density of DNA helices, including: 1) a single-layer honeycomb pattern (SH) with 2-3 nm pores between helices; 2) a single-layer square pattern (SS) with smaller 0.5-1 nm pores between helices, and 3) a double-layer square pattern (DS). The helix density at the top and bottom surfaces thus increased from 0.12 helices per nm2 for SH to 0.16 helices per nm2 for the SS and DS designs. The kcat of G6pDH encapsulated in the SH-cage was 4.7-fold higher than that of the free enzyme. As the density of DNA helices was increased, the kcat of encapsulated G6pDH raised to 6-fold for the SS-cage and 8-fold for the DS-cage compared to the free enzyme control. A slight increase in KM values was also observed from the SH-cage to the SS- and DS-cages, possibly due to a decrease in substrate diffusion through the DNA walls of these more tightly packed structures. For example, the KM value of G6pDH increased from 411 M in the SH-cage to 436 M in the SS-cage and 527 M in the DS-cage. Additional studies showed that activities of attached enzymes were enhanced by increasing the helix packing density for various 1D, 2D and 3D DNA scaffolds. These observations suggest that encapsulated enzymes exhibit higher activity within densely packed DNA cages, consistent with our model that the highly ordered, hydrogen-bonded water environment near closely spaced phosphate groups are responsible for this effect.

Nanocaged enzymes are protected from proteolysis. Self-assembled DNA nanostructures previously were found to be more resistant against nuclease degradation than single- or double-stranded DNA molecules. Similarly, DNA nanocages protect encapsulated enzymes from deactivation and aggregation under challenging biological conditions. Encapsulated GOx/HRP was highly resistant to digestion by trypsin, and retained more than 95% of its initial activity after incubation with trypsin for 24 h. A time-course experiment was also performed to demonstrate the stability of caged enzymes against Trypsin digestion. In contrast, free GOx/HRP only retained 50% of its initial activity after a similar incubation with trypsin. This result demonstrated the potential utility of DNA nanocages for protecting encapsulated proteins from biological degradation.

Example 12

Activity of Double Nanostructure Comprising DNA Cage and RNA Nanorobot.

The experiments in Example 11 are performed using a nanostructure comprising a DNA nanocage linked to an RNA nanorobot structure as disclosed herein. The results from DNA cage activity test in the double nanostructure demonstrate that encapsulated protein, in the DNA cage comprising the double nanostructure exhibits activity as when it is in single DNA cage structure, as shown in Example 11, above.

In some embodiments the protein in any DNA cage moiety of this invention is a metabolic enzyme, protease and/or a therapeutic agent as described herein.

The experiments also show that localized protein activity of the DNA caged protein is increased by the protective, and activity enhancing effects of the DNA cage and by the cell-specific, localizing activity of the RNA robot moiety.

All DNA and RNA sequences presented herein are oriented 5'->3', unless noted otherwise.

Although the foregoing specification and examples fully disclose and enable certain embodiments, they are not intended to limit the scope, which is defined by the claims appended hereto.

All publications, patents and patent applications are incorporated herein by reference. While in the foregoing specification certain embodiments have been described, and many details have been set forth for purposes of illustration, it will be apparent to those skilled in the art that additional embodiments and certain details described herein may be varied considerably without departing from basic principles.

The use of the terms "a" and "an" and "the" and similar referents are to be construed to cover both the singular and the plural, unless otherwise indicated herein or clearly contradicted by context.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the technology and does not pose a limitation on the scope of the technology unless otherwise claimed. No language in the specification should be construed as indicating any non-claimed element as essential to the practice of the technology.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the embodiment.

Embodiments are described herein, including the best mode known to the inventors. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this technology includes all modifications and equivalents of the subject matter recited in the claims appended hereto as permitted by applicable law. Moreover, any combination of the above-described elements in all possible variations thereof is encompassed by embodiments unless otherwise indicated herein or otherwise clearly contradicted by context.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. An RNA nanostructure robot having the sequence of $(R_3)_n$—$NR_1$-L-$NR_2$—$(R_4)_m$, wherein:
   $NR_1$ and $NR_2$ independently represent an RNA nanostructure each comprising a nucleic acid sequence having at least about 90% sequence identity to SEQ ID NO:1 or SEQ ID NO: 9 that self-assembles into respective first and second scaffolds;
   L is a linker which operably links $NR_1$ to $NR_2$;
   wherein $R_3$ and $R_4$ are independently selected from a pair of fastener strands, an aptamer, a cargo molecule, a capture strand, a targeting strand, and H;
   n is an integer from 1 to 20; and
   m is an integer from 0 to 20.

2. An RNA nanostructure robot having the sequence of $(R_3)_n$—$NR_1$-L-$NR_2$—$(R_4)_m$, wherein:
   $NR_1$ and $NR_2$ independently represent an RNA nanostructure each comprising a nucleic acid sequence having at least about 90% sequence identity to SEQ ID NO:1 or SEQ ID NO: 9 that self-assembles into respective first and second scaffolds;
   L is a linker which operably links $NR_1$ to $NR_2$;
   wherein $R_3$ is selected from a pair of fastener strands, an aptamer, a cargo molecule, a capture strand, a targeting strand, and H;
   n is an integer from 1 to 20; and
   m is an integer from 0 to 20,
   wherein $R_4$ is a targeting strand operably linked to a targeting moiety and to $NR_2$,
   wherein the targeting moiety is an aptamer that specifically binds nucleolin.

3. The RNA nanostructure robot of claim 2, wherein the aptamer that specifically binds nucleolin is the F50 AS1411 aptamer having the sequence: 5'-GGTGGTGGTGGTTGTGGTGG TGGTGG-3' (SEQ ID NO: 38).

4. The RNA nanostructure robot of claim 1, wherein the RNA nanostructure comprises a nucleic acid sequence wherein the nucleic acid sequence has at least about 95% sequence identity to SEQ ID NO:1 or SEQ ID NO: 9.

5. The RNA nanostructure robot of claim 1, wherein the RNA nanostructure comprises a nucleic acid sequence wherein the nucleic acid sequence comprises SEQ ID NO:1 or SEQ ID NO: 9.

6. An RNA nanostructure robot having the sequence of $(R_3)_n$—$NR_1$-L-$NR_2$—$(R_4)_m$, wherein:
   $NR_1$ and $NR_2$ independently represent an RNA nanostructure each comprising a nucleic acid sequence having at least about 90% sequence identity to SEQ ID NO:1 or SEQ ID NO: 9 that self-assembles into respective first and second scaffolds;
   L is a linker which operably links $NR_1$ to $NR_2$;
   wherein $R_3$ and $R_4$ are independently selected from a pair of fastener strands, an aptamer, a cargo molecule, a capture strand, a targeting strand, and H;
   n is an integer from 1 to 20;
   m is an integer from 0 to 20,
   wherein $NR_1$ or $NR_2$ further comprises at least one operably linked therapeutic agent, and wherein the therapeutic agent is a peptide or a polypeptide.

7. The RNA nanostructure robot of claim 6, wherein the polypeptide therapeutic agent is a positively-charged moiety comprising 10 lysine residues.

8. The RNA nanostructure robot of claim 6, wherein the peptide therapeutic agent is a tumor targeting peptide (TTP) or a human cancer peptide.

9. The RNA nanostructure robot of claim 6, wherein the polypeptide therapeutic agent is calreticulin.

10. The RNA nanostructure robot of claim 9, wherein the calreticulin protein engages interactions between tumor cells and macrophages or dendritic cells for enhanced antigen presentation and stimulation of antigen-specific T cells.

11. The RNA nanostructure robot of claim 8, wherein the human cancer peptide is a human NY-ESO-1 or Muc1 peptide.

12. The RNA nanostructure robot of claim 8, wherein the TTP is CTKD-K10 having the sequence: CTKDNNLLGR-FELSGGGSKKKKKKKKKK (SEQ ID NO: 3).

13. The RNA nanostructure robot of any of claim 1, 2, or 6, wherein the RNA nanostructure robot is a TLR3 agonist.

14. The RNA nanostructure robot of claim 1, wherein $R_3$ is a pair of DNA fastener strands configured to fasten the first or second scaffold into an origami structure.

15. The RNA nanostructure robot of claim 1, wherein $R_4$ is a pair of DNA fastener strands selected from the following DNA oligonucleotide pairs:
   5'-FITC-labeled F50 and 3'-BHQ1-labeled Comp15;
   FITC-F50-48 and Comp15-48-Q;
   FITC-F50-73 and Comp15-73-Q;
   FITC-F50-97 and Comp15-97-Q;
   FITC-F50-120 and Comp15-120-Q;
   FITC-F50-144 and, Comp15-144-Q; and
   FITC-F50-169 and Comp15-169-Q;
   wherein the aforementioned oligonucleotides have the following sequences:

```
5'-FITC-labeled F50:
                                                  (SEQ ID NO: 10)
5'-FITC-GGTGGTGGTGGTTGTGGTGGTGGTGGTCTAAAGTTTTGTCG

TGAATTGCG-3';

3'-BHQ1-labeled Comp15:
                                                  (SEQ ID NO: 11)
5'-GTAAAGCTTTTTTTTTTTACAACCACCACCACC-3';

FITC-F50-48:
                                                  (SEQ ID NO: 12)
5'-FITC-GGTGGTGGTGGTTGTGGTGGTGGTGGTCTAAAGTTTTGTCG

TGAATTGCG-3';
```

-continued

Comp15-48-Q:
(SEQ ID NO: 13)
5'-GTAAAGCTTTTTTTTTTTACAACCACCACCACC-BHQ1-3';

FITC-F50-73
(SEQ ID NO: 14)
5'-FITC-GGTGGTGGTGGTTGTGGTGGTGGTGGTAGAGCTTGACGGGG AAATCAAAA-3';

Comp15-73-Q:
(SEQ ID NO: 15)
5'-TGTAGCATTTTTTTTTTTACAACCACCACCACC-BHQ1-3';

FITC-F50-97:
(SEQ ID NO: 16)
5'-FITC-GGTGGTGGTGGTTGTGGTGGTGGTGGCGAGAAAGGAAGGGA ACAAACTAT-3';

Comp15-97-Q:
(SEQ ID NO: 17)
5'-TGAGTTTCTTTTTTTTTTTACAACCACCACCACC-BHQ1-3';

FITC-F50-120:
(SEQ ID NO: 18)
5'-FITC-GGTGGTGGTGGTTGTGGTGGTGGTGGATAGGAACCCATGTA CAAACAGTT-3';

Comp15-120-Q:
(SEQ ID NO: 19)
5'-CAAGCCCATTTTTTTTTTTACAACCACCACCACC-BHQ1-3';

FITC-F50-144:
(SEQ ID NO: 20)
5'-FITC-GGTGGTGGTGGTTGTGGTGGTGGTGGCACCACCCTCATTTT CCTATTATT-3';;

Comp15-144-Q:
(SEQ ID NO: 21)
5'-CCGCCAGCTTTTTTTTTTTACAACCACCACCACC-BHQ1'-3';

FITC-F50-169:
(SEQ ID NO: 22)
5'FITC-GGTGGTGGTGGTTGTGGTGGTGGTGGCTACATTTTGACGCTC ACCTGAAA-3';

Comp15-169-Q:
(SEQ ID NO: 23)
5'-CCCTCAGTTTTTTTTTTTACAACCACCACCACC-BHQ1-3'[[.]];

F50 and Comp15;
F50-48 and Comp15-48;
F50-73 and Comp15-73;
F50-97 and Comp15-97;
F50-120 and Comp15-120;
F50-144 and, Comp15-144; and
F50-169 and Comp15-169;
wherein the aforementioned oligonucleotides have the following sequences:

F50:
(SEQ ID NO: 24)
GGTGGTGGTGGTTGTGGTGGTGGTGGTCTAAAGTTTTGTCGTGAATTGC G-3';

Comp15:
(SEQ ID NO: 25)
5'-GTAAAGCTTTTTTTTTTTACAACCACCACCACC-3';

F50-48:
(SEQ ID NO: 26)
5'-GGTGGTGGTGGTTGTGGTGGTGGTGGTCTAAAGTTTTGTCGTGAA TTGCG-3';

Comp15-48:
(SEQ ID NO: 27)
5'-GTAAAGCTTTTTTTTTTTACAACCACCACCACC-3';

FF50-73
(SEQ ID NO: 28)
5'-GGTGGTGGTGGTTGTGGTGGTGGTGGTAGAGCTTGACGGGGAAAT CAAAA-3';

Comp15-73:
(SEQ ID NO: 29)
5'-TGTAGCATTTTTTTTTTTACAACCACCACCACC-3';

F50-97:
(SEQ ID NO: 30)
5'-GGTGGTGGTGGTTGTGGTGGTGGTGGCGAGAAAGGAAGGGAACAA ACTAT-3';

Comp15-97:
(SEQ ID NO: 31)
5'-TGAGTTTCTTTTTTTTTTTACAACCACCACCACC-3';

F50-120:
(SEQ ID NO: 32)
5'-GGTGGTGGTGGTTGTGGTGGTGGTGGATAGGAACCCATGTACAAA CAGTT-3';

Comp15-120:
(SEQ ID NO: 33)
5'-CAAGCCCATTTTTTTTTTTACAACCACCACCACC-3';

F50-144:
(SEQ ID NO: 34)
5'-GGTGGTGGTGGTTGTGGTGGTGGTGGCACCACCCTCATTTTCCTA TTATT-3';;

Comp15-144:
(SEQ ID NO: 35)
5'-CCGCCAGCTTTTTTTTTTTACAACCACCACCACC-3';

F50-169:
(SEQ ID NO: 36)
5'-GGTGGTGGTGGTTGTGGTGGTGGTGGCTACATTTTGACGCTCACC TGAAA-3';

Comp15-169:
(SEQ ID NO: 37)
5'-CCCTCAGTTTTTTTTTTTACAACCACCACCACC-3'.

* * * * *

SEQUENCE LISTING

```
<160> NUMBER OF SEQ ID NOS: 132

<210> SEQ ID NO 1
<211> LENGTH: 2002
<212> TYPE: RNA
<213> ORGANISM: Artificial Sequence
<220> FEATURE:
```

<223> OTHER INFORMATION: Description of Artificial Sequence: Synthetic
      polynucleotide

<400> SEQUENCE: 1

| | | | | | |
|---|---|---|---|---|---|
| gggagagagc | ucgagcgaac | acuagccacu | ugaucacgcu | gagcgcucgu | acaaugaaac | 60 |
| acaggugugu | cagugcuaug | cacguucgaa | gagcuguauc | agcguucgug | ugaaugaguu | 120 |
| caacggagug | uugacuaagc | cgguugcuac | auuucuguag | cacacauagu | caagauuugc | 180 |
| accagacgau | acucucccuc | aguccuguuu | augcaagucg | ucuagucccu | gacguacuuc | 240 |
| cuaagcucgu | cacuguacug | augauuccac | ugaucaagau | gcacguaucu | ucaguuuccu | 300 |
| gaagaucgga | guaggcacua | uaaucgacaa | guaacgcuua | cgauuccauc | acgagugacu | 360 |
| uaccugaacc | auaacugaca | agggaccacg | cagaggucau | acucacagga | cuucaaaucu | 420 |
| ugagucgggu | ucgaucauuu | cugaucgaga | caccagugug | agguaaucgu | acgucacuug | 480 |
| auaggagcuc | uaaguagagu | ugagagccug | uuaacuagac | acgaguaacg | agguuagccu | 540 |
| gucgagauua | ucgggcuaua | gugcggacac | gauugcacca | uuucggugc | aacgaaggug | 600 |
| agcauguaug | gacaggucag | ugugacucaa | gucgauaguc | caaguagguu | aucgacucgc | 660 |
| auagcucaau | gacugucauc | gccagaguau | cuagguguca | accucacgaa | ucgcgucguu | 720 |
| acauuucugu | aacgcucaua | ccgugcugau | cuaugggaca | cgucgcuuau | ucuuggguca | 780 |
| ugacaguugc | cacaaacaag | gcacgaccuc | acaccgcga | acuucaagcg | uuaggcugac | 840 |
| guuacaugcu | ugcgugcacu | gauucguuuc | cgaaucagag | accuacgaag | ccagaguucg | 900 |
| uucacuauca | uaagcacu | gaugcauuug | ugccaacauu | gaaggcaucg | agauaaacag | 960 |
| ccgucuuaau | caagugagca | ccugagauca | gcaugauucg | ucuauuucua | gacgaaucaa | 1020 |
| cuuccauuca | ggugccuugc | uacuuaagac | gggauuaacu | cucgaugcaa | cgugcauugg | 1080 |
| cacaacucgu | gaugugcacu | uucacacugg | aacgaacucu | ggcuucguag | gucuguuugu | 1140 |
| cauuucugac | aaacugcacg | cacuguuagu | acgucagcca | cuuaaccgaa | guucgucaua | 1200 |
| aguaggucgu | gcgacuacga | uggcaacuuc | uacuuaccaa | gaauaagcga | cgugucccau | 1260 |
| aauggaaguc | gguaugaggu | augacuuucg | ucauacacgc | gauuccacaa | ugugacaccu | 1320 |
| aacguuugag | gcgaugaccu | gauacaagcu | augcauggu | caaaccuacu | uggacuaucg | 1380 |
| acuugagaug | auaguaccug | uccaacuaac | agcaccuucg | auaccucguu | uccgagguau | 1440 |
| ucguguccug | ugucaggccc | gauauuaaug | uguggcuaac | ccuuaggaac | gugcuaguu | 1500 |
| aacaggcucu | caacgucaug | acgagcuccu | aguagcaagc | guacgauaca | uugugacugg | 1560 |
| ugucuacugg | auuucuccag | uaacccgacu | ccgacuacaa | agccugacu | cauucacccuc | 1620 |
| ugcgugguccc | cuugucaguu | gagucgaugg | uaagcaaug | caucaggaau | cgugguuaag | 1680 |
| ucuugucgau | cugacacacu | acuccgcugu | ccuguuccca | ggacagacgu | gcauuagcag | 1740 |
| uugugggaauc | aucaguacag | ugacgagucg | uuacuguacg | ucagcuuguu | ugcgacuugc | 1800 |
| aguuaaucga | cugaggguca | aacgucucug | uguguagu | ggacuauguu | acguucauuu | 1860 |
| cugaacguac | cggcuuagcu | aacacuccgu | ugaugaguau | gacacgaacg | agucauuggc | 1920 |
| ucuucgcuuc | aauguagcac | ugaacuuaug | auguuucaua | cacauuacgc | ucagcgaacu | 1980 |
| gcuauggcua | guguucggau | cc | | | | 2002 |

<210> SEQ ID NO 2
<211> LENGTH: 2002
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 2

```
gggagagagc tcgagcgaac actagccact tgatcacgct gagcgctcgt acaatgaaac      60
acaggtgtgt cagtgctatg cacgttcgaa gagctgtatc agcgttcgtg tgaatgagtt     120
caacggagtg ttgactaagc cggttgctac atttctgtag cacacatagt caagatttgc     180
accagacgat actctccctc agtcctgttt atgcaagtcg tcgtagtcct gacgtacttc     240
ctaagctcgt cactgtactg atgattccac tgatcaagat gcacgtatct tcagtttcct     300
gaagatcgga gtaggcacta taatcgacaa gtaacgctta cgattccatc acgagtgact     360
tacctgaacc ataactgaca agggaccacg cagaggtcat actcacagga cttcaaatct     420
tgagtcgggt tcgatcattt ctgatcgaga caccagtgtg aggtaatcgt acgtcacttg     480
ataggagctc taagtagagt tgagagcctg ttaactagac acgagtaacg aggttagcct     540
gtacgagata tcgggctata gtgcggacac gattgcacca tttctggtgc aacgaaggtg     600
agcatgtatg gacaggtcag tgtgactcaa gtcgatagtc caagtaggtt atcgactcgc     660
atagctcaat gactgtcatc gccagagtat ctaggtgtct acctcacgaa tcgcgtcgtt     720
acatttctgt aacgctcata ccgtgctgat ctatgggaca cgtcgcttat tcttgggtca     780
tgacagttgc cacaaacaag gcacgacctc acacctgcga acttcaagcg ttaggctgac     840
gttacatgct tgcgtgcact gattcgtttc cgaatcagag acctacgaag ccagagttcg     900
ttcactatca taagtgcact gatgcatttg tgccaacatt gaaggcatcg agataaacag     960
ccgtcttaat caagtgagca cctgagatca gcatgattcg tctatttcta gacgaatcaa    1020
cttccattca ggtgccttgc tacttaagac gggattaact ctcgatgcaa cgtgcattgg    1080
cacaactcgt gatgtgcact ttcacactgg aacgaactct ggcttcgtag gtctgtttgt    1140
catttctgac aaactgcacg cactgttagt acgtcagcca cttaaccgaa gttcgtcata    1200
agtaggtcgt gcgactacga tggcaacttc tacttaccaa gaataagcga cgtgtcccat    1260
aatggaagtc ggtatgaggt atgactttcg tcatacacgc gattccacaa tgtgacacct    1320
aacgtttgag gcgatgacct gatacaagct atgcatggtt caaacctact tggactatcg    1380
acttgagatg atagtacctg tccaactaac agcaccttcg atacctcgtt tccgaggtat    1440
tcgtgtcctg tgtcaggccc gatattaatg tgtggctaac ccttaggaac gtgtctagtt    1500
aacaggctct caacgtcatg acgagctcct agtagcaagc gtacgataca ttgtgactgg    1560
tgtctactgg atttctccag taacccgact ccgactacaa agtcctgact cattcacctc    1620
tgcgtggtcc cttgtcagtt gagtcgatgg taagtcaatg catcaggaat cgtggttaag    1680
tcttgtcgat ctgacacact actccgctgt cctgtttcca ggacagacgt gcattagcag    1740
ttgtggaatc atcagtacag tgacgagtcg ttactgtacg tcagcttgtt tgcgacttgc    1800
agttaatcga ctgagggtca aacgtgtctg gtgtgtagtc ggactatgtg acgttcatt    1860
ctgaacgtac cggcttagtc aacactccgt tgatgagtat gacacgaacg agtcattggc    1920
tcttcgcttc aatgtagcac tgaacttatg atgtttcata cacattacgc tcagcgaact    1980
gctatggcta gtgttcggat cc                                             2002
```

<210> SEQ ID NO 3
<211> LENGTH: 28
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 3

Cys Thr Lys Asp Asn Asn Leu Leu Gly Arg Phe Glu Leu Ser Gly Gly
1               5                   10                  15

Gly Ser Lys Lys Lys Lys Lys Lys Lys Lys
            20                  25

<210> SEQ ID NO 4
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4 uuuc                                                                    4

<210> SEQ ID NO 5
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5 gggaggg                                                                 7

<210> SEQ ID NO 6
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6 cccuccc                                                                 7

<210> SEQ ID NO 7
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7 aaagaaa                                                                 7

<210> SEQ ID NO 8
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8 uuucuuu                                                                 7

<210> SEQ ID NO 9
<211> LENGTH: 3909
```

<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9

```
cacgaacuca uccucacgcc gccggucgcg ugcggcgccg gcagaaggac cugaugcauc      60
gagcggugac agcgccaccg gaguagcuca guuauucgau ucaguauauu acguaauaua     120
cggcgagaag uugcagcagu gcgcuguauu uuagcauguc gcgcuaacua cgaugauugg     180
caauaagauu acgaccgcua ucucauggcu uaucaaagug ggcaaggucu ugcccacggc     240
guugacgucc gacccgucgu uaagugucag agucggugua cccuuagauc uggccacgca     300
cgagguccac caugguacu cgcgucagga caguaaccuu acugucgccg cuccgagcgc      360
auauuucgcc ucaggcgggc gguuacccgu uaaucuuuag gcaaacuacg cacgggcuug     420
uuuugugucu ccacucucgg gguacuuugg aguaccccgg uagaagaaug uuccgguucg     480
cgugcgggcg gccguuacac ugggcgacug cauagggccc cccgcccgcc ucgcccuaaa     540
uuucacccau uaagcgagaa agcauucucg caacuggqua uggacuuggg guguccugga    600
uucgaucacg caccggucgc cgaagugggcg ggaagagcac cccuacgucg ggucuuacag     660
gacacgcgac ccuacuucgg cguacccccc gguacgcccg cgcccgcaga gcggucgauu     720
ggucacacgg uggaagugag ucuguugucg ccguuucuac aauccgucug cugcaacggg     780
ccagguuggu uauuaauaac caaagugccg gagcuccggc ccgucauagg ugauccacag     840
cgguaauau cuuaccugcu ccuucagagg gcggggcaag ggcgucggac gaguguauuu      900
guuacgucau aacguaacac ucggcaucg ggugcuagcg ccagaccgcg cgcacuggcg      960
gcgagagagu cuuauacgcc aggucuagc caauaugcgc ucacuuaagg uguucaugua    1020
caugaacaaa agcuacauga ggacggcugc uugauuucca acaggcuacg uguuucugg    1080
cuggccaaau aagucgagga ggcgggaaca uuugacgacu cucugguauc cuuaccagag    1140
gggugaacua accaaauucc uggaagaauu gguccuauag cccuaugagc uaggaacggu    1200
cuguuuuucc gagaccguca aguccaguug gcggauggu ggcgucccca ccauguaggc     1260
uaccuugucg ugaccgaauu ccggcccaga gaauugggqc aacggcgcac uccuucugc    1320
cgccucuccc gcucugcagg cgccacagcu cgcgcacgag cugucccuac gccagaaggg    1380
cuccucaugc gaaguacacc gucaguaagu cuggcccucu aaaauaaaua ccuugccgga    1440
gcgaggcacu gggaacguag ggacguuccu cuaaguaugc acaauccaca uaagccgacg    1500
aaugcgccgc acugacguga aacuggacuu ggcugacacu caaaaggccg cacccgaggc    1560
ccccgaugu ggcuacgacc acaucucgcg ccguuguaag gucgagcccu ucaacuaaua    1620
guuuuaaacc cacucgguag gguucccuau aacccaaaac cccgccuguu ugggcgcguc    1680
cucauaggug ccuaggcaag gccgcuugcc uugguugcgg ggcagauuuu ccuaacuaau    1740
cguccaccgc gaaggcuccc ugaaaagcac ccgcccgcac acguguauuu gguuaugguc    1800
uucuacgauu ggacgcaauc guauccuacc ccgucgggggc cggcccgcga caacaggusa    1860
acgaccuugg cuugggcaug ucaucggacg gauagcaagc accgaaucca caaccugucg    1920
acaaggcuga uccucccucc ggggaggauc aguggcaau acagguuguu aguccggugc    1980
uugcucgcuc gauaaggucg uaccgugugu gucgcgggcc cuucggccgg gguaggauc    2040
agcaccaaau ggcugagaga agaccauuaa agggguacacg ugcaacaua gauagggauu    2100
uacgccgggu gcuuuuguag uuagcuucgc ggugaucac caguuaggag ucguggauug    2160
```

```
gcaaccacau uaacgacggu uaaugaggca ccuaaaucau uucgcccaaa ucuaccaagu      2220
uuuggguuaa ggguacccu  acccgcgcgg uuuaaaacga ccuuacaacg gcgcgaacgc      2280
cauguacgca uggcguggg  ggccgaccga auggccuuuu gggguaugcc caaguccaga      2340
uuaacgucag ugcguuggaa augucggcuu auagcaaauc ugcauacuua gagugacgcu      2400
agagcgucac cagugccucu gauuccuaag guauuccuca gccucccucu aacuaugcac      2460
agggccagau cgcccagcgg uguacaccaa uucaggagcc ggccccgagu agggugcaga      2520 uguggcauc  ugcaggcgcc uggucggcu  ggagggcggg ugucgaaagu gcgccggcga      2580
ccgaauucuc uggccggaa  uuaacgguuu cccgaguggc ggucaauugc ccauagccua      2640
cagcgacacg caggugucgc uccgccaacg aauuaguacg gucucuccgg uggagaccgu      2700
uccuacagac ucgggcuaua gguucgcaug uuccaggaac ccuuuaaguu caccccugca      2760
ccgaggccgg ugcagagucg ucagacgggc gcgccuccuc cuuauugcug gccagcuccg      2820
guaagauuag ccuggcgcau uccaagcagc aaaugauuug uagcuuuaau uaaggcaccu      2880
uaauuccuua agugaucguc ucuuggcuag ucgugcgugu auaagacucu cucgccgcca      2940
guggaguggg ucuggcgcua auucggucug ccguagguuc cuaccuuugu aggaacaaua      3000
cacucuaacu aggcccuugc cugcguaguu gaaggagcag uucagaaaca cccgcugug       3060 gacgauuuau gacggaggaa ucauccggca cuugcuuuau cgauaaagca ccuggccgu       3120 uacgcaggac ggauucgggc ggcggcgaca agcucauaac uuccucaccu guaccaaucg      3180
aagccgaccc gggcgcguca gcggggguac ccgcugagaa guagggaugg gcguccuggg      3240
ugcucuuccc gccacuucgu ugccccguc  gugaucggac uaaggacacc cacuaauucu      3300
acccaguucg uaacgauauc guuacguuaa ugggugaaau aacuggcgag gcggggugaa      3360
aacccuaugc agcuuacuga uguaacggcc ggcgugacgc gaacccgccc guccuucuac      3420
cgugauuggu gucccaauca cgagaguggc aucaugagau aagccgccg  cccucuugcc      3480 uaaaguuuca cggguaaccg uugguagaag gcgaaagaga cgaucggagc ggccccgu       3540 gccugacggg gcugacgcga guacccaugg ucgcaugccc gugcagaugg acccaccugg      3600
cggccagauc uauagggaca ccgacugcau acccuaacga cggcuaguua gucaacgccg      3660
gggccgcaca cgcggcccu  uugauaagcg acagacacaa ggucguaaug acuuauucaa      3720
ucauccaggg agccgcgaca uggugcaagg cagcgcaccu gcuaacuuc  ucgcccgagg      3780 auacucaucc ucgugaaucg aauuuaggag cuacgaaaaa accgcuguca cauccggccg      3840
caucagguuc gacacccggc gccgcgccca uccggcggcg ugaggaugag uucgugucc       3900 cgggccacc                                                              3909
```

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggtggtggtg gttgtggtgg tggtggtcta aagttttgtc gtgaattgcg               50

<210> SEQ ID NO 11
<211> LENGTH: 34
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 11
gtaaagcttt tttttttta caaccaccac cacc                              34

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggtggtggtg gttgtggtgg tggtggtcta aagttttgtc gtgaattgcg            50

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtaaagcttt tttttttta caaccaccac cacc                              34

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtggtggtg gttgtggtgg tggtggtaga gcttgacggg gaaatcaaaa            50

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgtagcattt tttttttta caaccaccac cacc                              34

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggtggtggtg gttgtggtgg tggtggcgag aaaggaaggg aacaaactat            50

<210> SEQ ID NO 17
<211> LENGTH: 34
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 17
tgagtttctt ttttttttta caaccaccac cacc                                    34

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggtggtggtg gttgtggtgg tggtggatag gaacccatgt acaaacagtt                   50

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caagcccatt tttttttttt acaaccacca ccacc                                   35

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggtggtggtg gttgtggtgg tggtggcacc accctcattt tcctattatt                   50

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccgccagctt ttttttttta caaccaccac cacc                                    34

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtggtggtg gttgtggtgg tggtggctac attttgacgc tcacctgaaa                   50

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 23
ccctcagttt tttttttta caaccaccac cacc                               34

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggtggtggtg gttgtggtgg tggtggtcta aagttttgtc gtgaattgcg             50

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtaaagcttt tttttttta caaccaccac cacc                               34

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggtggtggtg gttgtggtgg tggtggtcta aagttttgtc gtgaattgcg             50

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtaaagcttt tttttttta caaccaccac cacc                               34

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggtggtggtg gttgtggtgg tggtggtaga gcttgacggg gaaatcaaaa             50

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgtagcattt tttttttta caaccaccac cacc                34

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtggtggtg gttgtggtgg tggtggcgag aaaggaaggg aacaaactat                50

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgagtttctt tttttttta caaccaccac cacc                34

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtggtggtg gttgtggtgg tggtggatag gaacccatgt acaaacagtt                50

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caagcccatt ttttttttt acaaccacca ccacc                35

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggtggtggtg gttgtggtgg tggtggcacc accctcattt tcctattatt                50

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccgccagctt tttttttta caaccaccac cacc                                34

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggtggtggtg gttgtggtgg tggtggctac attttgacgc tcacctgaaa              50

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ccctcagttt tttttttta caaccaccac cacc                                34

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggtggtggtg gttgtggtgg tggtgg                                        26

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aaaaaaaaaa aaaatttgc cagatcagtt gagatttagt ggtttaa                  47

<210> SEQ ID NO 40
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaaaaaaaaa aaaaagcaaa tatcgcgtct ggccttcctg gcctcag                 47

<210> SEQ ID NO 41
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aaaaaaaaaa aaaaatatat tttagctgat aaattaatgt tgtataa        47

<210> SEQ ID NO 42
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaaaaaaaaa aaaaaccgt tctaaatgca atgcctgaga ggtggca        47

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aaaaaaaaaa aaaaattat ttaacccagc tacaattttc aagaacg        47

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaaaaaaaaa aaagaagga aataagagc aagaaacaac agccat        46

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aaaaaaaaaa aaaagccca ataccgagga aacgcaatag gtttacc        47

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aaaaaaaaaa aaaataacc tccatatgtg agtgaataaa caaaatc        47

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaaaaaaaaa aaaaacatat ttagaaatac cgaccgtgtt acctttt                                47

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaaaaaaaaa aaaaaatgg tttacaacgc caacatgtag ttcagct                                 47

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggtggtggtg gttgtggtgg tggtggtttt cgatggccca ctacgtaaac cgtc                        54

<210> SEQ ID NO 50
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggtggtggtg gttgtggtgg tggtggtttt cggtttgcgt attgggaacg cgcg               54

<210> SEQ ID NO 51
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggtggtggtg gttgtggtgg tggtggtttt gacagcatcg gaacgaaccc tcag               54

<210> SEQ ID NO 52
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggtggtggtg gttgtggtgg tggtggattt tactttcaac agtttctggg attt               54

<210> SEQ ID NO 53
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggtggtggtg gttgtggtgg tggtggtttt accagtaata aaagggattc acca               54

```
<210> SEQ ID NO 54
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggtggtggtg gttgtggtgg tggtggtttt aatcaatatc tggtcacaaa tatc        54

<210> SEQ ID NO 55
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtggtggtg gttgtggtgg tggtggtttt ataaatcctc attaaatgat attc        54

<210> SEQ ID NO 56
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggtggtggtg gttgtggtgg tggtggtttt tataagtata gcccggccgt cgag        54

<210> SEQ ID NO 57
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
cggaaucagu gaaugcuuau acauccg                                      27

<210> SEQ ID NO 58
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gccuuaguaa cgugcuuuga ugucgauucg acaggaggc                         39

<210> SEQ ID NO 59
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ugccgcuaua augcacggau uuaaucgccg uagaaaagca gucaaagcc g             51
```

<210> SEQ ID NO 60
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ccccggguuc uguaugaucc gaccggucag auaagaccac                              40

<210> SEQ ID NO 61
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
cgcaucguuu gcguggcgug uccgggcgcc gauucguaaa                              40

<210> SEQ ID NO 62
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
cuaggcggau uguuucgauu cuuugccuug ucccuagugc                              40

<210> SEQ ID NO 63
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cguauauacg gauuagguug uagcucagac caguaauguc                              40

<210> SEQ ID NO 64
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cgugcuagau gcuacgagug gucuccucac guagaagggg                              40

<210> SEQ ID NO 65
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ggucccacau agguuggucu uguuguaugg gcuguuugca                              40

```
<210> SEQ ID NO 66
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
guguuuuggg agagaaaagg gggagccuuu acuuuguugg                              40

<210> SEQ ID NO 67
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gacgauguua ucagggaguu gggaucauau agucuuacau                              40

<210> SEQ ID NO 68
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
cgcaagagcc gcccuaaugg uucaauggua acuguauaug                              40

<210> SEQ ID NO 69
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gacuucuugu gccauuauga auuauugcua auccucuuga                              40

<210> SEQ ID NO 70
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
aggacguacu uggaaaagag gcgcgaagaa ccugguaugu                              40

<210> SEQ ID NO 71
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uaggacguac uuggaaaaga ggcgcgaaga accugguaug                              40

<210> SEQ ID NO 72
```

<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
uggccaccuu gccacucuuc cuugcauauu uuacucccgc					40

<210> SEQ ID NO 73
<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
caagccgagg gggaguaucu gaugacaauu cggagcucca					40

<210> SEQ ID NO 74
<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
ucauggugug ugaguuagcu cacgugccgu uucgaaggcg					40

<210> SEQ ID NO 75
<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
caugggcuag accggcauaa aacugcugua guugcacgcc					40

<210> SEQ ID NO 76
<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
uggccaccuu gccacucuuc cuugcauauu uuacucccgc					40

<210> SEQ ID NO 77
<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
cguuguagua guggcuuggg cauaacucag uuaaacacua					40

<210> SEQ ID NO 78
<211> LENGTH: 40

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gaccgcggaa aaggaaggaa uuagauacaa cggagaagug                                40

<210> SEQ ID NO 79
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gaccgcggaa aaggaaggaa uuagauacaa cggagaagug                                40

<210> SEQ ID NO 80
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cgcaucguuu gcguggcgug uccgggcgcc gauucguaaa                                40

<210> SEQ ID NO 81
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ucauggugug ugaguuagcu cacgugccgu uucgaaggcg                                40

<210> SEQ ID NO 82
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
caagccgagg gggaguaucu gaugacaauu cggagcucca                                40

<210> SEQ ID NO 83
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cguauauacg gauuagguug uagcucagac caguaauguc                                40

<210> SEQ ID NO 84
<211> LENGTH: 64
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 84
tacgactcac tagggatc ctgtatatat tttgcaacta attgaattcc ctttagtgag    60
ggtt    64

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 85
gcccaagctg gcatccgtca    20

<210> SEQ ID NO 86
<211> LENGTH: 11
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 86
cccaggctac g    11

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 87
caattgggcc cgtccgtatg gtgggt    26

<210> SEQ ID NO 88
<211> LENGTH: 25
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 88
tgtgggggtg gacgggccgg gtaga    25

<210> SEQ ID NO 89
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 89
ggtggtggtg gttgtggtgg tggtgg    26

<210> SEQ ID NO 90
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: 2'-deoxyinosine

<400> SEQUENCE: 90
ggtggtggtg gttgtggtgg tggngg                                          26

<210> SEQ ID NO 91
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
acgagyygyc gcaygygcgg yycagycygg yccyycagca ccgyacaaca a              51

<210> SEQ ID NO 92
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctcctctgac tgtaaccacg cctgggacag ccacacagaa gtgtagacct cgcggaatcg     60
gcataggtag tccagaagcc                                                 80

<210> SEQ ID NO 93
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
gcggaagcgu gcugggcuag aauaauaaua agaaaaccag uacuuucgu                 49

<210> SEQ ID NO 94
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cgaaaccaga ccaccccacc aaggccactc ggtcgaaccg ccaacactca cccca          55

<210> SEQ ID NO 95
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gatcttgaaa ctgttttaag gttggccgat c                                      31

<210> SEQ ID NO 96
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
cggccacaga augaaaaacc ucaucgaugu ugcauaguug                              40

<210> SEQ ID NO 97
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
cgacccggca caaacccaga accatataca cgatcattag tctcctgggc cg                52

<210> SEQ ID NO 98
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gggaccgaaa aagacctgac ttctatacta agtctacgtt ccc                         43

<210> SEQ ID NO 99
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cgctcggatc gataagcttc gatcccactc tcccgttcac ttctcctcac gtcacggatc        60
ctctagagca ctg                                                          73

<210> SEQ ID NO 100
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gggagagagg aagagggaug ggcgaccgaa cgugcccuuc aaagccguuc acuaaccagu        60
ggcauaaccc agaggucgau aguacuggau cccccc                                 96

<210> SEQ ID NO 101
<211> LENGTH: 40
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 101
cagucugcau cguaggaauc gccaccguau acuuucccac                              40

<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cagagacttc caaaataaaa gactc                                             25

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ctgaaagttg caaaataaaa aactc                                             25

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cacttaccac aataacaaac gggtg                                             25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cctgcaccac agggagacgg gggcc                                             25

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gattagacca taggctccca acccc                                             25

<210> SEQ ID NO 107
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 107
tctgaggtgc tcctgctttg gaact                                           25

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
caagaccgtt atgtcgtgtg tactt                                           25

<210> SEQ ID NO 109
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ccgacgtgcc gcaacttcaa ccctgcacaa ccaatccgcc                           40

<210> SEQ ID NO 110
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gggaggacga ugcggaucag ccauguuuac gucacuccuu gucaauccuc aucggcagac     60
gacucgcccg a                                                          71

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gtacagttcc cgtccctgca ctaca                                           25

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gtacagttcc cgtcctgcac taca                                            24

<210> SEQ ID NO 113
<211> LENGTH: 45
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 113
acgggccaca tcaactcatt gatagacaat gcgtccactg cccgt          45

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctgtaattgg cgtatgtaac ccaggcacca acaccccag                 40

<210> SEQ ID NO 115
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aaaaagcaac agggtgctcc atgcgcatcg aacctgcgcg                40

<210> SEQ ID NO 116
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gggatggatc caagcttact ggcatctgga tttgcgcgtg ccagaataaa gagtataacg    60
tgtgaatggg aagcttcgat aggaattcgg                                    90

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gcgactggtt acccggtcgt aa                                   22

<210> SEQ ID NO 118
<211> LENGTH: 309
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 118
gggagaggac caugaguca cuauggucuu ggagcuagcg gcagagcguc gcgguccuc     60 ccgggagagg accauguacu gguaguucuc ugugcgacuc cuacagagag ucgcgguccc  120
ucccgggaga ggaccaugua cuggguugua gggggcucc uuaggcagag cgucgcgguc   180
```

```
ccucccggga gaggaccaug uaccccgcaa ugcggcccca gacuucaaca gagcgucggg      240
ucccucccgg gagaggacca uguaccgcau gugcgcgaga gguagcgaca gagcgucgcg      300
gucccuccc                                                              309

<210> SEQ ID NO 119
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tccctacggc gctaacgatg gtgaaaatgg gcctagggtg gacggtgcca ccgtgctaca      60
ac                                                                     62

<210> SEQ ID NO 120
<211> LENGTH: 3909
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
catgaactca tcctcacgcc gccggtcgcg tgcggcgccg gcagaaggac ctgatgcatc      60
gagcggtgac agcgccaccg gagtagctca gttattcgat tcagtatatt acgtaatata     120
cggcgagaag ttgcagcagt gcgctgtatt ttagcatgtc gcgctaacta cgatgattgg     180
caataagatt acgaccgcta tctcatggct tatcaaagtg ggcaaggtct tgcccacggc     240
gttgacgtcc gacccgtcgt taagtgtcag agtcggtgta cccttagatc tggccacgca     300
cgaggtccac catgggtact cgcgtcagga cagtaacctt actgtcgccg ctccgagcgc     360
atatttcgcc tcaggcgggc ggttacccgt taatctttag gcaaactacg cacgggcttg     420
ttttgtgtct ccactctcgg ggtactttgg agtaccccgg tagaagaatg ttccggttcg     480
cgtgcgggcg gccgttacac tgggcgactg catagggccg cccgcccgcc tcgccctaaa     540
tttcacccat taagcgagaa agcattctcg caactgggta tggacttggg gtgtcctgga     600
ttcgatcacg caccggtcgc cgaagtggcg ggaagagcac ccctacgtcg ggtcttacag     660
gacacgcgac cctacttcgg cgtacccccc ggtacgcccg cgcccgcaga gcggtcgatt     720
ggtcacacgg tggaagtgag tctgttgtcg ccgtttctac aatccgtctg ctgcaacggg     780
ccaggttggt tattaataac caaagtgccg gagctccggc ccgtcatagg tgatccacag     840
cgggtaatat cttacctgct ccttcagagg gcggggcaag ggcgtcggac gagtgtattt     900
gttacgtcat aacgtaacac tacggcatcg ggtgctagcg ccagaccgcg cgcactggcg     960
gcgagagagt cttatacgcc aggtgctagc caatatgcgc tcacttaagg tgttcatgta    1020
catgaacaaa agctacatga ggacggctgc ttgatttcca acaggctacg gtgtttctgg    1080
ctggccaaat aagtcgagga ggcgggaaca tttgacgact ctctggtatc cttaccagag    1140
gggtgaacta accaaattcc tggaagaatt ggtcctatag ccctatgagc taggaacggt    1200 ctgttttttcc gagaccgtca agtccagttg gcggatggtg ggcgtcccca ccatgtaggc    1260
taccttgtcg tgaccgaatt ccggcccaga gaattggggc aacggcgcac ttccttctgc    1320
cgccctcccc gctctgcagg cgccacagct cgcgcacgag ctgtccctac gccagaaggg    1380
ctcctcatgc gaagtacacc gtcagtaagt ctggccctct aaaataaata ccttgccgga    1440
```

```
gcgaggcact gggaacgtag ggacgttcct ctaagtatgc acaatccaca taagccgacg    1500
aatgcgccgc actgacgtga aactggactt ggctgacact caaaaggccg cacccgaggc    1560
cccccgatgt ggtcacgacc acatctcgcg ccgttgtaag gtcgagccct tcaactaata    1620
gttttaaacc cactcggtag ggttccctat aacccaaaac cccgcctgtt tgggcgcgtc    1680
ctcataggtg cctaggcaag gccgcttgcc ttggttgcgg ggcagatttt cctaactaat    1740
cgtccaccgc gaaggctccc tgaaaagcac ccgcccgcac acgtgtattt ggttatggtc    1800
ttctacgatt ggacgcaatc gtatcctacc ccgtcgggc cggcccgcga caacaggtga    1860
acgaccttgg cttgggcatg tcatcggacg gatagcaagc accgaatcca caacctgtcg    1920
acaaggctga tcctccctcc ggggaggatc agtgggcaat acaggttgtt agtccggtgc    1980
ttgctcgctc gataaggtcg taccgtgtgt gtcgcgggcc cttctggccg gggtaggatc    2040
agcaccaaat ggtgctgaga agaccattaa agggtacacg tgtcaacata gataggattt    2100
tacgcccggg gcttttgtag ttagcttcgc ggtggatcac cagttaggag tcgtggattg    2160
gcaaccacat taacgacggt taatgaggca cctaaatcat ttcgcccaaa tctaccaagt    2220
tttgggttaa gggtaaccct acccgcgcgg tttaaaacga ccttacaacg gcgcgaacgc    2280
catgtacgca tggcgtgggg ggccgaccga atggcctttt ggggtatgcc caagtccaga    2340
ttaacgtcag tgcgttggaa atgtcggctt atagcaaatc tgcatactta gagtgacgct    2400
agagcgtcac cagtgcctct gattcctaag gtattcctca gcctccctct aactatgcac    2460
agggccagat cgcccagcgg tgtacaccaa ttcaggagcc ggccccgagt agggtgcaga    2520
tgtgggcatc tgcaggcgcc tgggtcggct ggagggcggg tgtcgaaagt gcgccggcga    2580
ccgaattctc tgggccggaa ttaacggttt cccgagtggc ggtcaattgc ccatagccta    2640
cagcgacacg caggtgtcgc tccgccaacg aattagtacg gtctctccgg tggagaccgt    2700
tcctacagac tcgggctata ggttcgcatg ttccaggaac cctttaagtt caccctgca    2760 ccgaggccgg tgcagagtcg tcagacgggc gcgcctcctc cttattgctg gccagctccg    2820
gtaagattag cctggcgcat tccaagcagc aaatgatttg tagctttaat taaggcacct    2880
taattcctta agtgatcgtc tcttggctag tcgtgcgtgt ataagactct ctcgccgcca    2940
gtggagtggg tctggcgcta attcggtctg ccgtaggttc ctacctttgt aggaacaata    3000
cactctaact aggcccttgc ctgcgtagtt gaaggagcag ttcagaaaca acccgctgtg    3060
gacgatttat gacggaggaa tcatccggca cttgctttat cgataaagca cctggcccgt    3120
tacgcaggac ggattcgggc ggcggcgaca agctcataac ttcctcacct gtaccaatcg    3180
aagccgaccc gggcgcgtca gcggggtac ccgctgagaa gtagggatgg gcgtcctggg    3240
tgctcttccc gccacttcgt tgccccgtgc gtgatcggac taaggacacc cactaattct    3300
acccagttcg taacgatatc gttacgttaa tgggtgaaat aactggcgag gcggggtaga    3360
aaccctatgc agcttactga tgtaacggcc ggcgtgacgc gaaccccgccc gtccttctac    3420 cgtgattggt gtcccaatca cgagagtggc atcatgagat aagcccgccg ccctcttgcc    3480
taaagtttca cgggtaaccg ttggtagaag gcgaaagaga cgatcggagc ggcccccgtc    3540
gcctgacggg gctgacgcga gtaccatgg tcgcatgccc gtgcagatgg acccacctgg    3600
cggccagatc tatagggaca ccgactgcat accctaacga cggctagtta gtcaacgccg    3660
gggccgcaca cgcggcccct ttgataagcg acagacacaa ggtcgtaatg acttattcaa    3720
tcatccaggg agccgcgaca tggtgcaagg cagcgcacct gcgtaacttc tcgcccgagg    3780
```

```
atactcatcc tcgtgaatcg aatttaggag ctacggaaaa accgctgtca catccggccg    3840
catcaggttc gacacccggc gccgcgccca tccggcggcg tgaggatgag ttcgtgtccg    3900
cgggccacc                                                            3909
```

<210> SEQ ID NO 121
<211> LENGTH: 14
<212> TYPE: PRT
<213> ORGANISM: Homo sapiens

<400> SEQUENCE: 121

```
Thr Lys Asp Asn Asn Leu Leu Gly Arg Phe Glu Leu Ser Gly
1               5                   10
```

<210> SEQ ID NO 122
<211> LENGTH: 14
<212> TYPE: PRT
<213> ORGANISM: Mus sp.

<400> SEQUENCE: 122

```
Thr Arg Asp Asn Asn Leu Leu Gly Arg Phe Glu Leu Ser Gly
1               5                   10
```

<210> SEQ ID NO 123
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123

```
ggggttggtt gtgttgggtg ttgtgtccaa cccc                                 34
```

<210> SEQ ID NO 124
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

```
aaaaaaaaaa aaaacaaaa atcattgctc cttttgataa gtttcat                    47
```

<210> SEQ ID NO 125
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125

```
aaaaaaaaaa aaaaaaaga ttcaggggggt aatagtaaac cataaat                   47
```

<210> SEQ ID NO 126
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126

```
tttttccctc cctcc                                                      15
```

<210> SEQ ID NO 127
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tttttggctg gctgg                                                    15

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tttttccctc cctcc                                                    15

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tttttggagg gaggg                                                    15

<210> SEQ ID NO 130
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
cgtagagcau ca                                                       12

<210> SEQ ID NO 131
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
tgatcctggg t                                                        11

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic

```
oligonucleotide
<220> FEATURE:
<223> OTHER INFORMATION: Description of Combined DNA/RNA Molecule:
      Synthetic oligonucleotide

<400> SEQUENCE: 132
cggaaucagu gaaugcuuau acauccgt                                          28
```